United States Patent

Ryder et al.

[11] Patent Number: 5,962,451
[45] Date of Patent: Oct. 5, 1999

[54] BENZODIAZEPIN DERIVATIVES USEFUL AS CCK-RECEPTOR ANTAGONISTS

[75] Inventors: Hamish Ryder; Graeme Semple, both of Southampton; David Alan Kendrick, Eastleigh; Michael Szelke, Romsey, all of United Kingdom; Masato Satoh, Ibakaki, Japan; Mitsuaki Ohta, Ibaraki, Japan; Keiji Miyata, Ibaraki, Japan; Akito Nishida, Ibaraki, Japan

[73] Assignees: Ferring BV, Netherlands; Yamanouchi Pharmaceutical Co. Ltd., Tokyo, Japan

[21] Appl. No.: 08/867,422

[22] Filed: Jun. 6, 1997

Related U.S. Application Data

[62] Division of application No. 08/284,462, filed as application No. PCT/GB93/00404, Feb. 26, 1993, Pat. No. 5,688,943.

[30] Foreign Application Priority Data

Feb. 27, 1992 [GB] United Kingdom .................... 9204221
Jun. 16, 1992 [GB] United Kingdom .................... 9212740

[51] Int. Cl.⁶ ......................... A61K 31/55; C07D 243/10
[52] U.S. Cl. ............................. 514/221; 540/509
[58] Field of Search ............... 540/509; 514/221

[56] References Cited

U.S. PATENT DOCUMENTS

| | | | |
|---|---|---|---|
| 4,820,834 | 4/1989 | Evans et al. | 540/504 |
| 5,206,234 | 4/1993 | Bock et al. | 514/213 |

FOREIGN PATENT DOCUMENTS

| | | |
|---|---|---|
| 0 284 256 A1 | 9/1988 | European Pat. Off. |
| 0 421 802 A2 | 4/1991 | European Pat. Off. |
| 0 434 360 A1 | 6/1991 | European Pat. Off. |
| 0 434 364 A2 | 6/1991 | European Pat. Off. |
| 0 434 369 A1 | 6/1991 | European Pat. Off. |
| 0 445 976 A1 | 9/1991 | European Pat. Off. |
| 0 508 797 A1 | 10/1992 | European Pat. Off. |
| 0 508 799 A1 | 10/1992 | European Pat. Off. |

OTHER PUBLICATIONS

Lotti et al., "A new potent and selective non–peptide gastrin antagonist and brain cholecystokinin . . .", *European Jnl. of Pharm.*, 162:273–280, 1989.

Bock, et al., "Development of 1,4–Benzodiazepine Cholecystokinin Type B Antagonists", *Jnl. Med. Chem.*, 36:4276–4292, 1993.

Bock, et al., "Benzodiazepine Gastrin and Brain Cholecystokinin Receptor Ligands: L–356,260", *Jnl. Med. Chem.*, 32:13–16, 1989.

*Primary Examiner*—Mukund J. Shah
*Assistant Examiner*—Brenda Coleman
*Attorney, Agent, or Firm*—Foley & Lardner

[57] ABSTRACT

A benzodiazepine derivative of formula (I), or a pharmaceutically acceptable salt thereof, wherein (a) $R^1$ is —$CH_2CHOH(CH_2)_aR^4$ or a ketone group —$CH_2CO(CH_2)_aR^5$ in which a is 0 or 1 and $R^4$ and $R^5$ are selected from alkyl and cycloalkyl groups and saturated heterocyclic groups optionally substituted at a hetero-atom; (b) $R^2$ and $R^3$ are independently selected from aromatic carbocyclic and heterocylic residues; and (c) W and X are selected independently from halogen and hydrogen atoms and alkyl and alkoxy groups. These compounds are gastrin and/or CCK-B receptor antagonists.

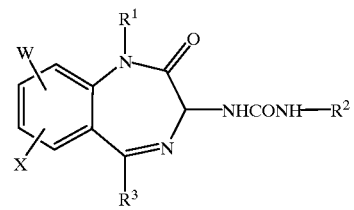

(I)

20 Claims, No Drawings

BENZODIAZEPIN DERIVATIVES USEFUL AS CCK-RECEPTOR ANTAGONISTS

This application is a division of application Ser. No. 08/284,462, filed Sep. 14, 1994, now U.S. Pat. No. 5,688,943 which is the national stage of application PCT/GB93/00404, filed Feb. 26, 1993.

This invention relates to benzodiazepine derivatives which are useful as drugs exhibiting antagonism at the gastrin and/or CCK-B receptor, and to their production.

Many benzodiazepine derivatives have been described in the course of development of psychotropic drugs which act as agonists at the "benzodiazepine receptor" in the central nervous system. More recently benzodiazepine derivatives have been described which act as antagonists at the CCK-A (cholecystokinin-A) and CCK-B receptors. It was further reported that those compounds which were selective antagonists for the CCK-B receptor were able to reduce the secretion of gastric acid in response to the administration of pentagastrin (V. J. Lotti & R. S. L. Chang, *Eur.J.Pharmacol.* 162, 273–280, 1989). Examples of benzodiazepine derivatives which act as antagonists at the CCK-B receptor are disclosed in, for example, U.S. Pat. No. 4,820,834.

The compounds of the present invention are novel. They differ from the compounds described in U.S. Pat. No. 4,820,834, particularly in the nature of the substituent at position 1 of the benzodiazepine nucleus. The present invention includes compounds of better pharmacological characteristics than those described in U.S. Pat. No. 4,820,834; preferred compounds of the invention have a higher affinity for the CCK-B receptor and/or discriminate more selectively between the CCK-B and CCK-A receptors than the previously described compounds.

The present invention provides a benzodiazepine derivate of formula I, or a pharmaceutically acceptable salt thereof

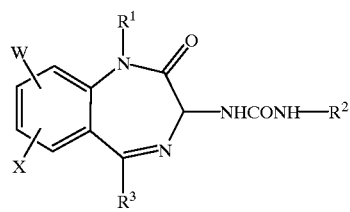

wherein
(a) $R^1$ is —$CH_2CHOH(CH_2)_aR^4$ or a ketone group —$CH_2CO(CH_2)_aR^5$ in which a is 0 or 1 and $R^4$ and $R^5$ are selected from alkyl and cycloalkyl groups and saturated heterocyclic groups optionally substituted at a hetero-atom;
(b) $R^2$ and $R^3$ are independently selected from aromatic carbocylic and heterocyclic residues; and
(c) W and X are selected independently from alkyl and alkoxy groups and halogen and hydrogen atoms.

Herein all "alkyl", "cycloalkyl", "acyl" and "alkoxy" groups are preferably of up to 8 carbon atoms, and "halogen" may for example be fluorine, chlorine, bromine or iodine. The aromatic residues herein ($R^2$, $R^3$) may be substituted; they are preferably monocyclic, usually of 5 or 6 ring atoms; when heterocyclic they may for example have 1, 2 or 3 hetero ring atoms. Preferably at least one of $R^2$ and $R^3$ is unsubstituted, monosubstituted or disubstituted phenyl or unsubstituted, monosubstituted or disubstituted 2-, 3-, or 4-pyridyl. Preferably one (most preferably each) of W and X is a hydrogen atom.

Preferably $R^4$ is alkyl (e.g. $C_4$–$C_7$, linear or branched); or is cyclo- or polycycloalkyl (which may be unsubstituted or substituted with one or more alkyl groups) and contains e.g. from 3 to 8 carbon atoms; or is of formula II or III:

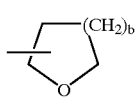

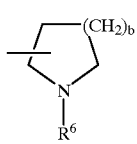

in which $R^6$ is H, alkyl (e.g. $C_1$–$C_3$) or —CO-alkyl (where the alkyl is e.g. $C_1$–$C_3$) and b is 1 or 2. Preferably $R^5$ is alkyl (e.g. $C_1$–$C_3$) or as defined for $R^4$.

Examples of alkyl and cycloalkyl groups include tert-butyl, cyclopentyl and cyclohexanemethyl.

Examples of saturated heterocyclic groups include pyrrolidyl and tetrahydropyranyl. Examples of substituents at the heteroatom include simple alkyl and acyl groups (e.g. of up to 3,4,5 or 6 carbon atoms, such as formyl, acetyl, etc).

Examples of substituents on the aromatic residues ($R^2$, $R^3$) include halogen atoms (e.g. fluorine, chlorine, etc); hydroxy amino, nitro, carboxylic acid and cyano groups; and alkyl, alkoxy, alkylamino and dialkylamino groups in which the or each alkyl component is preferably of up to 6 (e.g. up to 3) carbon atoms (methyl; ethyl etc.); for substituted $R^2$, meta-substitution is preferred.

Most preferably $R^2$ is unsubstituted phenyl; phenyl having a meta substituent chosen from F, Cl, Br, OH, $OCH_3$, $NH_2$, $NMe_2$, $NO_2$, Me, —$(CH_2)_c$—$CO_2H$, CN, NHMe, NMeEt, $NEt_2$, $CH_2NMe_2$, NHCHO and —$(CH_2)_c$—$SO_3H$ where c is 0–2; or 2-, 3- or 4-pyridyl optionally with a substituent selected from F, Cl, $CH_3$ and $CO_2H$.

Most preferably $R^3$ is phenyl or 2-, 3- or 4-pyridyl.

W xnd X are preferably both H, but when either is alkyl or alkoxy it is preferably of 1 to 3 carbon atoms.

The compounds of this invention all have at least one stereogenic centre and so can exist as optical isomers. It should be understood that these isomers, either separately or as mixtures, are included within the scope of this invention. In addition, the compounds of this invention can form salts with inorganic or organic acids or, in some cases, bases. Examples of such salts would include chlorides, sulphates and acetates, or sodium and potassium salts. These salts should also be understood to be included within the scope of this invention. In preferred compounds according to the invention, the absolute configuration at the 3-position of the benzodiazepine ring is R (as shown in IV).

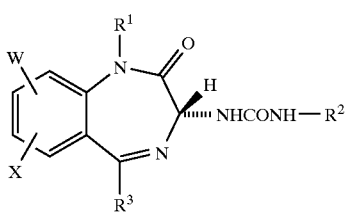

Compounds according the invention act as CCK-B and gastrin receptor antagonists. They may be used as drugs for the treatment of diseases induced by the failure of a physiological function controlled by gastrin, such as gastric and duodenal ulcers, gastritis, reflux esophagitis, gastric and colon cancers, and Zollinger-Ellison syndrome; there may be no side effects arising from CCK-A receptor interaction. They may be used as drugs for the treatment of diseases induced by the failure of physiological function controlled by the central CCK-B receptor (e.g. for the reduction of anxiety or for appetite regulation).

Amongst preferred compounds according to the invention are those listed below and salts thereof. Some of the compounds are exemplified hereinafter as indicated against the individual compounds concerned.

1. N-((3RS)-1-tert-Butylcarbonylmethyl-2,3-dihydro-2-oxo-5-phenyl-1H-1,4-benzodiazepin-3-yl)-N'-(3-methylphenyl) urea (Example 2);
2. N-((3RS)-1-Diethylmethylcarbonylmethyl-2,3-dihydro-2-oxo-5-phenyl-1H-1,4-benzodiazepin-3-yl)-N'-(3-methylphenyl) urea (Example 3);
3. N-((3RS)-1-Cyclobutylcarbonylmethyl-2,3-dihydro-2-oxo-5-phenyl-1H-1,4-benzodiazepin-3-yl)-N'-(3-methylphenyl) urea (Example 1);
4. N-((3RS)-1-Cyclopentylcarbonylmethyl-2,3-dihydro-2-oxo-5-phenyl-1H-1,4-benzodiazepin-3-yl)-N'-(3-methylphenyl) urea (Example 4);
5. N-((3RS)-1-Cyclohexylcarbonylmethyl-2,3-dihydro-2-oxo-5-phenyl-1H-1,4-benzodiazepin-3-yl)-N'-(3-methylphenyl) urea (Example 7);
6. N-((3RS)-1-Cycloheptylcarbonylmethyl-2,3-dihydro-2-oxo-5-phenyl-1H-1,4-benzodiazepin-3-yl)-N'-(3-methylphenyl) urea (Example 5);
7. N-((3RS)-Cycloheptylcarbonylmethyl-2,3-dihydro-2-oxo-5-phenyl-1H-1,4-benzodiazepin-3-yl)-N'-(3-chlorophenyl) urea (Example 6);
8. N-((3RS)-1-Cyclopentylcarbonylmethyl-2,3-dihydro-2-oxo-5-(2-pyridyl)-1H-1,4-benzodiazepin-3-yl-N'-(3-methylphenyl) urea (Example 14);
9. N-((3RS)-1-Cyclopentylcarbonylmethyl-2,3-dihydro-2-oxo-5-(3-pyridyl)-1H-1,4-benzodiazepin-3-yl)-N'-(3-methylphenyl) urea (Example 21);
10. N-((3RS)-1-Cyclopentylcarbonylmethyl-2,3-dihydro-2-oxo-5-(4-pyridyl)-1H-1,4-benzodiazepin-3-yl)-N'-(3-methylphenyl) urea (Example 15);
11. N-((3RS)-1-Cyclopentylcarbonylmethyl-2,3-dihydro-2-oxo-5-phenyl-1H-1,4-benzodiazepin-3-yl)-N'-(3-carboxyphenyl) urea (Example 16);
12. N-((3R)-1-Cyclopentylcarbonylmethyl-2, 3-dihydro-2-oxo-5-phenyl-1H-1,4-benzodiazepin-3-yl)-N'-(3-methylphenyl) urea (Example 17);
13. N-((3S)-1-Cyclopentylcarbonylmethyl-2,3-dihydro-2-oxo-5-phenyl-1H-1,4-benzodiazepin-3-yl)-N'-(3-methylphenyl) urea (Example 18);
14. N-((3RS)-2,3-Dihydro-2-oxo-5-phenyl-1-((2R)-2-pyrrolidylcarbonylmethyl)-1H-1,4-benzodiazepin-3-yl)-N'-(3-methylphenyl) urea (Example 10);
15. N-((3RS)-2,3-Dihydro-2-oxo-5-phenyl-1-((2S)-2-pyrrolidylcarbonylmethyl)-1H-1,4-benzodiazepin-3-yl)-N'-(3-methylphenyl) urea (Example 8);
16. N-((3RS)-1-((2R)-1-Acetyl-2-pyrrolidylcarbonylmethyl)-2,3-dihydro-2-oxo-5-phenyl-1H-1,4-benzodiazepin-3-yl)-N'-(3-methylphenyl)urea (Example 11);
17. N-((3RS)-1-((2S)-1-Acetyl-2-pyrrolidylcarbonylmethyl)-2,3-dihydro-2-oxo-5-phenyl-1H-1,4-benzodiazepin-3-yl)-N'-(3-methylphenyl)urea (Example 9);
18. N-((3RS)-1-((2RS)-2-Cyclopentyl-2-hydroxyethyl)-2,3-dihydro-2-oxo-5-phenyl-1H-1,4-benzodiazepin-3-yl)-N'-(3-methylphenyl) urea (Example 12);
19. N-((3RS)-1-((2SR)-2-Cyclopentyl-2-hydroxyethyl)-2,3-dihydro-2-oxo-5-phenyl-1H-1,4-benzodiazepin-3-yl)-N'-(3-methylphenyl) urea (Example 13);
20. N-((3R)-1-((2R)-2-Cyclopentyl-2-hydroxyethyl)-2,3-dihydro-2-oxo-5-phenyl-1H-1,4-benzodiazepin-3-yl)-N'-(3-methylphenyl) urea (Example 19);
21. N-((3R)-1-((2S)-2-Cyclopentyl-2-hydroxyethyl)-2,3-dihydro-2-oxo-5-phenyl-1H-1,4-benzodiazepin-3-yl)-N'-(3-methylphenyl) urea (Example 20);
22. N-((3RS)-1-Cyclopentylcarbonylmethyl-2,3-dihydro-2-oxo-5-phenyl-1H-1,4-benzodiazepin-3-yl)-N'-(3-cyanophenyl) urea (Example 49);
23. N-((3RS)-1-tert-Butylcarbonylmethyl-2,3-dihydro-2-oxo-5-phenyl-1H-1,4-benzodiazepin-3-yl)-N'-(3-cyanophenyl) urea (Example 50);
24. N-((3RS)-1-Cyclopentylcarbonylmethyl-2,3-dihydro-2-oxo-5-phenyl-1H-1,4-benzodiazepin-3yl)-N'-(3-carboxymethylphenyl) urea (Example 31);
25. N-((3RS)-1-(1-Adamantyl)carbonylmethyl-2,3-dihydro-2-oxo-5-phenyl-1H-1,4-benzodiazepin-3-yl)-N'-(3-methylphenyl) urea (Example 51);
26. N-((3RS)-1-Cyclopentylcarbonylmethyl-2,3-dihydro-2-oxo-5-phenyl-1H-1,4-benzodiazepin-3-yl)-N'-(3-pyridyl) urea (Example 30);
27. N-((3RS)-1-cyclopentylcarbonylmethyl-2,3-dihydro-2-oxo-5-phenyl-1H-1,4-benzodiazepin-3-yl)-N'-(6-methyl-2-pyridyl) urea (Example 29);
28. N-((3RS)-1-(3-Cyclohexyl-3-methyl-2-oxcobutyl)-2,3-dihydro-2-oxo-5-phenyl-1H-1,4-benzodiazepin-3-yl)-N'-(3-methylphenyl) urea (Example 52);
29. N-((3RS)-1-Cyclohexylmethylcarbonylmethyl-2,3-dihydro-2-oxo-5-phenyl-1H-1,4-benzodiazepin-3-yl)-N'-(3-methylphenyl) urea (Example 32);
30. N-((3RS)-1-Cyclopentylmethylcarbonylmethyl-2,3-dihydro-2-oxo-5-phenyl-1H-1,4-benzodiazepin-3-yl)-N'-(3-methylphenyl) urea (Example 33);
31. N-((3RS)-1-((1-Methylcyclohexyl)carbonylmethyl)-2,3-dihydro-2-oxo-5-phenyl-1H-1,4-benzodiazepin-3-yl)-N'-(3-methylphenyl) urea (Example 34);
32. N-((3RS)-1-((1-Methylcyclopentyl)carbonylmethyl)-2,3-dihydro-2-oxo-5-phenyl-1H-1,4-benzodiazepin-3-yl)-N'-(3-methylphenyl) urea (Example 46);
33. N-((3R)-1-Cyclopentylcarbonylmethyl-2,3-dihydro-2-oxo-5-phenyl-1H-1,4-benzodiazepin-3-yl)-N'-(3-carboxyphenyl) urea (Example 23);
34. N-((3RS)-1-Cyclopentylcarbonylmethyl-2,3-dihydro-2-oxo-5-(2-pyridyl)-1H-1,4-benzodiazepin-3-yl)-N'-(3-carboxyphenyl) urea (Example 22);
35. N-((3R)-1-((2RS)-2-Cyclopentyl-2-hydroxyethyl)-2,3-dihydro-2-oxo-5-phenyl-1H-1,4-benzodiazepin-3-yl)-N'-(3-carboxyphenyl) urea (Example 24);
36. N-((3R)-1-((2R)-2-Cyclopentyl-2-hydroxyethyl)-2,3-dihydro-2-oxo-5-phenyl-1H-1,4-benzodiazepin-3-yl)-N'-(3-carboxyphenyl) urea (Example 25);

37. N-((3RS)-1-Cyclopentylcarbonylmethyl-2,3-dihydro-2-oxo-5-phenyl-1H-1,4-benzodiazepin-3-yl)-N'-(3-carboxamidophenyl) urea (Example 35);
38. N-((3R)-1-tert-Butylcarbonylmethyl-2,3-dihydro-2-oxo-5-phenyl-1H-1,4-benzodiazepin-3-yl)-N'-(3-methylphenyl) urea (Example 26);
39. N-((3RS)-1-tert-Butylcarbonylmethyl-2,3-dihydro-2-oxo-5-(2-pyridyl)-1H-1,4-benzodiazepin-3-yl)-N'-(3-methylphenyl) urea (Example 27);
40. N-((3RS)-1-tert-Butylcarbonylmethyl-2,3-dihydro-2-oxo-5-phenyl-1H-1,4-benzodiazepin-3-yl)-N'-(3-carboxyphenyl) urea (Example 28);
41. N-((3RS)-1-tert-Amylcarbonylmethyl-2,3-dihydro-2-oxo-5-phenyl-1H-1,4-benzodiazepin-3-yl)-N'-(3-methylphenyl) urea (Example 36);
42. N-((3RS)-1-tert-Amylcarbonylmethyl-2,3-dihydro-2-oxo-5-phenyl-1H-1,4-benzodiazepin-3-yl)-N'-(3-carboxyphenyl) urea (Example 37);
43. N-((3RS)-1-tert-Butylcarbonylmethyl-2,3-dihydro-2-oxo-5-(2-pyridyl)-1H-1,4-benzodiazepin-3-yl)-N'-(3-dimethylaminophenyl) urea (Example 38);
44. N-((3RS)-1-tert-Butylcarbonylmethyl-2,3-dihydro-2-oxo-5-(2-pyridyl)-1H-1,4-benzodiazepin-3-yl)-N'-(3-carboxyphenyl) urea (Example 39);
45. N-((3RS)-1-Cyclopentylcarbonylmethyl-2,3-dihydro-2-oxo-5-phenyl-1H-1,4-benzodiazepin-3-yl)-N'-(3-dimethylaminophenyl) urea (Example 40);
46. N-((3RS)-1-tert-Butylcarbonylmethyl-2,3-dihydro-2-oxo-5-phenyl-1H-1,4-benzodiazepin-3-yl)-N'-(3-dimethylaminophenyl) urea (Example 41);
47. N-((3RS)-1-Cyclopentylcarbonylmethyl-2,3-dihydro-2-oxo-5-phenyl-1H-1,4-benzodiazepin-3-yl)-N'-(3-methoxyphenyl) urea (Example 42);
48. N-((3RS)-1-tert-Butylcarbonylmethyl-2,3-dihydro-2-oxo-5-phenyl-1H-1,4-benzodiazepin-3-yl)-N'-(3-methoxyphenyl) urea (Example 43);
49. N-((3RS)-1-Cyclopentylcarbonylmethyl-2,3-dihydro-2-oxo-5-phenyl-1H-1,4-benzodiazepin-3-yl)-N'-(3-nitrophenyl) urea (Example 44);
50. N-((3RS)-1-tert-Butylcarbonylmethyl-2,3-dihydro-2-oxo-5-phenyl-1H-1,4-benzodiazepin-3-yl)-N'-(3-nitrophenyl) urea (Example 45);
51. N-((3RS)-1-tert-Butylcarbonylmethyl-2,3-dihydro-2-oxo-5-phenyl-1H-1,4-benzodiazepin-3-yl)-N'-(3-formylaminophenyl) urea (Example 47);
52. N-((3R)-1-((2R)-2-Hydroxy-3,3-dimethylbutyl)-2,3-dihydro-2-oxo-5-phenyl-1H-1,4-benzodiazepin-3-yl)-N'-(3-methylphenyl) urea (Example 48);
53. N-((3R)-1-((2S)-2-Hydroxy-3,3-dimethylbutyl)-2,3-dihydro-2-oxo-5-phenyl-1H-1,4-benzodiazepin-3-yl)-N'-(3-methylphenyl)urea;
54. N-((3RS)-1-(1-Methylcyclopropyl)carbonylmethyl-2,3-dihydro-2-oxo-5-phenyl-1H-1,4-benzodiazepin-3-yl)-N'-(3-methylphenyl) urea (Example 53);
55. N-((3RS)-1-tert-Butylcarbonylmethyl-2,3-dihydro-2-oxo-5-(2-chlorophenyl)-1H-1,4-benzodiazepin-3-yl)-N'-(3-methylphenyl) urea (Example 54);
56. N-((3RS)-1-Isopropylcarbonylmethyl-2,3-dihydro-2-oxo-5-phenyl-1H-1,4-benzodiazepin-3-yl)-N'-(3-methylphenyl) urea (Example 55);
57. N-((3R)-1-tert-Butylcarbonylmethyl-2,3-dihydro-2-oxo-5-phenyl-1H-1,4-benzodiazepin-3-yl)-N'-(3-methylaminophenyl) urea (Example 56);
58. N-((3RS)-1-tert-Butylcarbonylmethyl-2,3-dihydro-2-oxo-5-(2-pyridyl)-1H-1,4-benzodiazepin-3-yl)-N'-(3-methylaminophenyl) urea (Example 57);
59. N-((3R)-1-tert-Butylcarbonylmethyl-2,3-dihydro-2-oxo-5-phenyl-1H-1,4-benzodiazepin-3-yl)-N'-(3-(N-ethyl-N-methylamino)phenyl) urea (Example 58);
60. N-((3R)-1-tert-Butylcarbonylmethyl-2,3-dihydro-2-oxo-5-phenyl-1H-1,4-benzodiazepin-3-yl)-N'-(3-diethylaminophenyl) urea (Example 59);
61. N-((3R)-1-tert-Butylcarbonylmethyl-2,3-dihydro-2-oxo-5-phenyl-1H-1,4-benzodiazepin-3-yl)-N'-(3-dimethylaminomethylphenyl) urea (Example 60);
62. N-((3RS)-1-tert-Butylcarbonylmethyl-2,3-dihydro-2-oxo-5-(2-pyridyl)-1H-1,4-benzodiazepin-3-yl)-N'-(3-(N-ethyl-N-methylamino)phenyl) urea (Example 61);
63. N-((3RS)-1-tert-Butylcarbonylmethyl-2,3-dihydro-2-oxo-5-(2-pyridyl)-1H-1,4-benzodiazepin-3-yl)-N'-(3-dimethylaminomethylphenyl) urea (Example 62);
64. N-((3RS)-1-tert-Butylcarbonylmethyl-2,3-dihydro-2-oxo-5-(2-pyridyl)-1H-1,4-benzodiazepin-3-yl-N'-(3-diethylaminophenyl urea (Example 63);
65. N-((3R)-1-tert-Butylcarbonylmethyl-2,3-dihydro-2-oxo-5-phenyl-1H-1,4-benzodiazepin-3-yl)-N'-(3-dimethylaminophenyl) urea (Example 64);
66. N-((3RS)-1-tert-Butylcarbonylmethyl-2,3-dihydro-2-oxo-5-(4-methylphenyl)-1H-1,4-benzodiazepin-3-yl)-N'-(3-methylphenyl) urea (Example 65);
67. N-((3R)-1-tert-Butylcarbonylmethyl-2,3-dihydro-2-oxo-5-phenyl-1H-1,4-benzodiazepin-3-yl)-N'-(3-aminophenyl) urea (Example 66);
68. N-((3R)-1-tert-Butylcarbonylmethyl-2,3-dihydro-2-oxo-5-(2-pyridyl)-1H-1,4-benzodiazepin-3-yl)-N'-(3-methylphenyl) urea;
69. N-((3R)-1-tert-Butylcarbonylmethyl-2,3-dihydro-2-oxo-5-(2-pyridyl)-1H-1,4-benzodiazepin-3-yl)-N'-(3-aminophenyl) urea;
70. N-((3R)-1-tert-Butylcarbonylmethyl-2,3-dihydro-2-oxo-5-(2-pyridyl)-1H-1,4-benzodiazepin-3-yl)-N'-(3-methylaminophenyl) urea;
71. N-((3R)-1-tert-Butylcarbonylmethyl-2,3-dihydro-2-oxo-5-(2-pyridyl)-1H-1,4-benzodiazepin-3-yl)-N'-(3-dimethylaminophenyl) urea;
72. N-((3RS)-1-tert-Butylcarbonylmethyl-2,3-dihydro-2-oxo-5-phenyl-1H-1,4-benzodiazepin-3-yl)-N'-(3-aminophenyl) urea;
73. N-((3RS)-1-tert-Butylcarbonylmethyl-2,3-dihydro-2-oxo-5-phenyl-1H-1,4-benzodiazepin-3-yl)-N'-(3-methylaminophenyl) urea;
74. N-((3RS)-1-tert-Butylcarbonylmethyl-7-chloro-2,3-dihydro-2-oxo-5-phenyl-1H-1,4-benzodiazepin-3-yl)-N'-(3-methylphenyl) urea (Example 67);
75. N-((3RS)-1-tert-Butylcarbonylmethyl-7-chloro-2,3-dihydro-2-oxo-5-phenyl-1H-1,4-benzodiazepin-3-yl)-N'-(3-dimethylaminophenyl) urea (Example 68);
76. N-((3RS)-1-tert-Butylcarbonylmethyl)-7-chloro-2,3-dihydro-2-oxo-5-(2-chlorophenyl)-1H-1,4-benzodiazepin-3-yl)-N'-(3-methylphenyl) urea (Example 69);
77. N-((3RS)-1-tert-Butylcarbonylmethyl-2,3-dihydro-8-methyl-2-oxo-5-phenyl-1H-1,4-benzodiazepin-3-yl)-N'-(3-methylphenyl) urea (Example 70);
78. N-((3RS)-1-tert-Butylcarbonylmethyl-2,3-dihydro-2-oxo-5-phenyl-1H-1,4-benzodiazepin-3-yl)-N'-(3-(N-ethyl-N-methylaminophenyl) urea;
79. N-((3RS)-1-tert-Butylcarbonylmethyl-2,3-dihydro-2-oxo-5-phenyl-1H-1,4-benzodiazepin-3-yl)-N'-(3-diethylaminophenyl) urea.

The compounds of the invention can be prepared according to the route outlined in Scheme I below.

Scheme 1

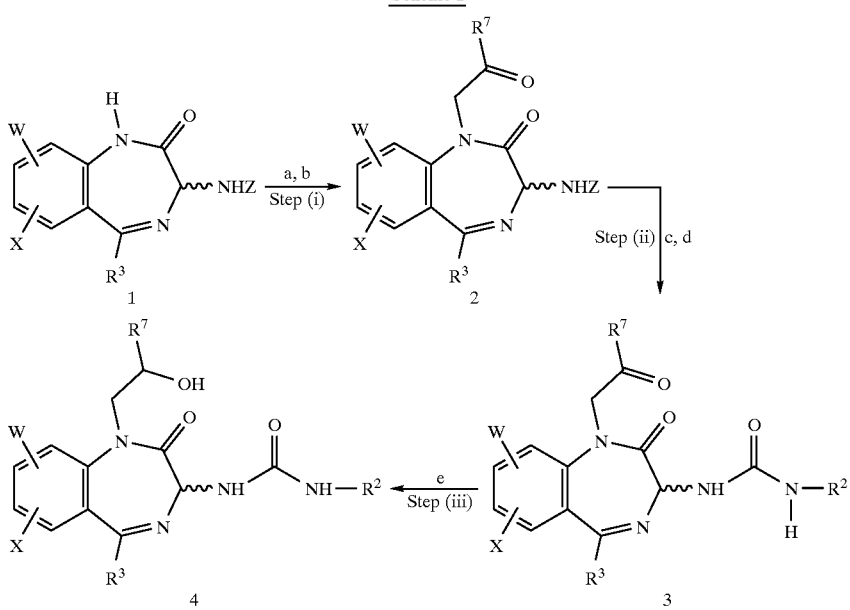

Reagents: (a) NaH, DMF; (b) $R^7COCH_2Br$; (c) $H_2$, Pd—C or HBr; (d) $R^2NCO$; (e) $NABH_4$ ($R^7$ represents $R^4(CH_2)_a$, or $R^5(CH_2)_a$)

When $R^3$=Ph, the starting material 1 is a known compound [M. G. Bock et al. *J. Org. Chem.* 52, 3232–3239, 1987]. For other examples of $R^3$, such as pyridyl, the starting material 1 can be prepared in a manner analogous to that described by Bock et al. For simplicity, in the specific examples which follow, the compound 1 ($R^3$=Ph) is referred to as the Bock benzodiazepine.

In step (i) the compound 1 is deprotonated with a strong base (typically sodium hydride) and then reacted with a bromomethyl ketone $R^7COCH_2Br$. In general, these ketones are not commercially available, but can be prepared from commercially available carboxylic acids or carboxylic acid chlorides by the route outlined in Scheme 2.

Scheme 2

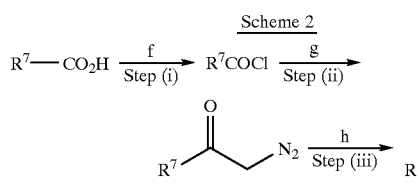

Reagents: (f) $SOCl_2$; (g) $CH_2N_2$; (h) HBr

The alkylated benzodiazepines 2 (Scheme 1) are then deprotected. Scheme 1 illustrates the case when the amino-group is protected by a Z group (Z=benzyloxycarbonyl) which can be removed by catalytic hydrogenolysis or acidic hydrolysis.

When a protecting group other than Z is used the deprotection step may need to be changed appropriately. The deprotected benzodiazepine is then treated with an aryl isocyanate ($R^2NCO$). When $R^2$=3-methylphenyl for example, this leads directly to compounds 3 which are listed above (e.g. compounds 1–10, etc). When $R^2$ contains a protected functional group (e.g. a carboxylic acid protected as an ester) this group must be unmasked to give the listed compound. The ketone 3 can be reduced by, for example, sodium borohydride to give the corresponding alcohol 4 (e.g. compounds 18–21, etc).

In some cases it is preferable to prepare the urea by an altenate route. This is outlined in Scheme 3.

Scheme 3

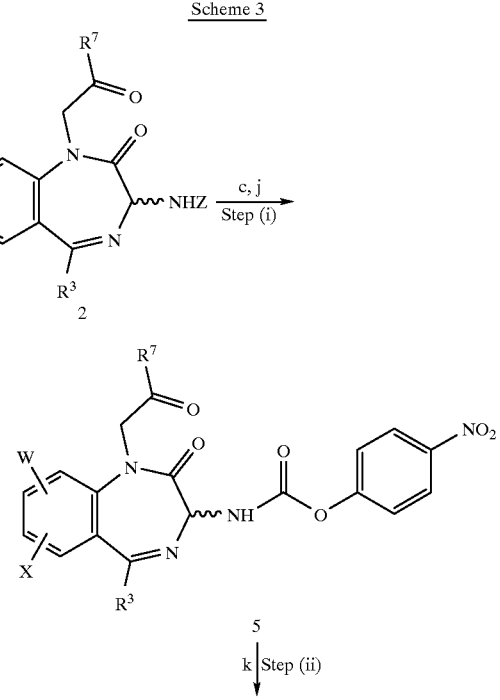

-continued

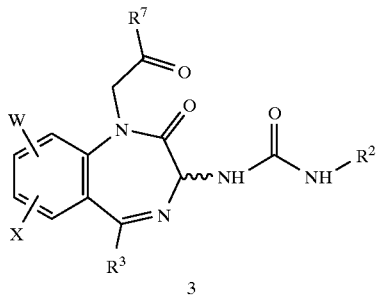

Reagents: (j) p-O$_2$NC$_6$OCOCl; (k) R$^2$NH$_2$

The protected benzodiazapine derivative 2 is protected as before {Scheme 1, step (ii)} but is then treated with p-nitrophenyl chloroformate to give the p-nitrophenyl carbamate 5. In step (ii) this is reacted with an amine R$^2$NH$_2$ to give the urea 3. This route is particularly useful when the isocyanate R$^2$NCO is not commercially available but the amine R$^2$NH$_2$ is.

These general methods will now be further illustrated with specific, non-limiting examples.

EXAMPLE 1

N-((3RS)-1-Cyclobutylcarbonylmethyl-2,3-dihydro-2-oxo-5-phenyl-1H-1,4-benzodiazepin-3-yl)-N'(3-methylphenyl)urea. Compound 3

1A Bromomethyl Cyclobutyl Ketone (Scheme 2. Steps (i)–(iii))

To an ice-cold solution of cyclobutanecarboxylic acid (1.5 g, 15 mmol) in Et$_2$O (10 ml) was added N,N-diisopropylethylamine (2.9 ml, 16 mmol) followed by thionyl chloride, (1.24 ml, 17 mmol). The mixture was stirred at 0° C. for 45 min. then poured into an ice-cold solution of CH$_2$N$_2$ (prepared from Diazald®, 14.1 g, 66 mmol) in Et$_2$O, and the resulting mixture was allowed to warm to room temperature over 2 hrs. A saturated solution of HBr in Et$_2$O was added dropwise until no more nitrogen was evolved. The resulting ethereal solution of bromomethyl ketone was washed successively with satd. KHCO$_3$, water and brine, filtered (Whatman® 1 PS phase separator), and concentrated in vacuo. The crude product was purified by bulb-to-bulb distillation (100° C., 5 mm Hg), to give the title ketone as a colourless, mobile oil (1.13 g, 44%).

NMR (CDCl$_3$) δ3.86 (2H, s); 3.57 (1H, quintet, J=8.5 Hz); 2.5–2.2 (6H, m); 2.2–1.8(2H, m).

1B (3RS)-3-Benzyloxycarbonylamino-1-cyclobutylcarbonylmethyl-2,3-dihydro-5-phenyl-1H-1,4-benzodiazepin-2-one {Scheme 1, Step (i)}

To a stirred solution of (3RS)-3-benzyloxycarbonylamino-2,3-dihydro-5-phenyl-1H-1,4-benzodiazepin-2-one [M. G. Bock et al. *J. Org. Chem.* 52, 3232–3239, 1987] (578 mg, from 605 mg of monohydrate azeotroped with DMF×3, 1.5 mmol) in DMF (5ml), cooled to −10° C. under N$_2$, was added sodium hydride (63 mg of 80% dispersion in oil, 2.1 mmol). The mixture was stirred at −10° C. for 30 min, when a solution of the bromomethyl ketone of Example 1A (398 mg, 2.25 mmol) in DMF (2 ml) was added. The resulting mixture was allowed to warm to room temperature with stirring over 1 hr, then poured into dilute aq. HCl (100 ml). The mixture was extracted once with EtOAc, and the organic layer was washed with water and brine, filtered (Whatman® 1 PS phase separator), and concentrated in vacuo. The crude product was purified by flash chromatography on silica gel (eluant EtOAc: 60–80 pet. ether 40:60 v/v) to give the title benzodiazepine as a glassy solid (490 mg, 68%).

R$_f$ (EtOAc: 60–80 pet. ether 50:50) 0.54.

NMR (CDCl$_3$) δ7.8–7.2 (14H, m); 6.70 (1H, d, J=8 Hz); 5.47 (1H, d, J=8 Hz); 5.18 (2H, s); 4.69 (H. d, J=7.5 Hz); 4.60 (1H, d, J=7.5 Hz); 3.36 (1H, quintet, J=8 Hz); 2.5–1.8 (6H, m).

1C N-((3RS)-1-Cyclobutylcarbonylmethyl-2,3-dihydro-2-oxo-5-phenyl-1H-1,4-benzodiazepin-3-yl)-N'-(3-methylphenyl) urea. (Scheme 1, Step (ii))

To a deoxygenated solution of the benzodiazepine of Example 1B (490 mg, 1.02 mmol) in glacial acetic acid (25 ml) was added 5% palladium-on-carbon catalyst (ca. 200 mg). Hydrogen gas was bubbled through the suspension for 4 hrs, and the reaction was terminated by nitrogen degassing. The mixture was filtered, and the catalyst residue was washed with methanol. The combined filtrates were evaporated in vacuo, and traces of solvent were finally removed by co-evaporation with toluene. The residue was taken up in CH$_2$Cl$_2$ (25 ml) and stirred at room temperature. To this solution was added m-tolyl isocyanate (0.13 ml, 1.02 mmol), and stirring was continued for 2 hrs. The solvent was evaporated in vacuo, and the crude product was purified by flash chromatography on silica gel (eluant EtOAc: 60–80 pet. ether 40:60 v/v). Finally the product was taken up in acetic acid and lyophilised to give the title benzodiazepine as a white powder (203 mg, 41%, >95% pure by HPLC).

R$_f$ (EtOAc: 60–80 pet. ether 35:65) 0.12.

NMR (CDCl$_3$) δ7.82 (2H, d, J=7 Hz); 7.8–7.2 (11H, m); 7.09 (1H, d, J=8 Hz); 6.99 (1H, d, J=7 Hz); 5.83 (1H, d, J=8 Hz); 4.78 (2H, s); 3.44 (1H, quintet, J=8.5 Hz); 2.43 (3H, s); 2.4–1.9 (6H, m).

M.S. (FAB, +ve ion) m/e 481.8 (M+H).

EXAMPLE 2

N-((3RS)-1-tert-Butylcarbonylmethyl-2,3-hydro-2-oxo-5-phenyl-1H-1,4-benzodiazepin-3-yl)-N'-(3-methylphenyl)urea. Compound 1

2A tert-Butyl Bromomethyl Ketone (Scheme 2, Steps (ii)–(iii))

To an ice-cold solution of CH$_2$N$_2$ (prepared from Diazald®, 10.4 g, 49 mmol) in Et$_2$O was added pivaloyl chloride (2 ml, 16 mmol). The solution was allowed to warm to room temperature with stirring over 3 hrs, when a saturated solution of HBr in EtOAc was added until no more nitrogen was evolved. The solution was washed with brine, filtered (Whatman® 1 PS phase separator), and concentrated in vacuo to give the title ketone as a mobile, pale brown oil (3.47 g, 82% pure by NMR, remainder EtOAc, 99%).

NMR (CDCl$_3$) δ4.15 (2H, s); 1.20 (9H, s).

2B (3RS)-3-Benzyloxycarbonylamino-1-tert-butylcarbonylmethyl-2,3-dihydro-5-phenyl-1H-1,4-benzodiazepin-2-one. (Scheme 1. Step (i))

This was prepared following the method of Example 1B using the Bock benzodiazepine (578 mg, 1.5 mmol), sodium hydride (63 mg of 80% dispersion in oil, 2.1 mmol) and the bromomethyl ketone of Example 2A (491 mg, 82% pure 2.25 mmol). The crude product was purified by flash chromatography on silica gel (eluant EtOAc: 60–80 pet. ether 50:50 v/v) to give the title benzodiazepine as a glassy, solid (700 mg, 97%).

R$_f$ (EtOAc: 60–80 pet. ether 50:50) 0.56.

NMR (CDCl$_3$) δ7.8–7.2 (14H, m); 6.74 (1H, d, J=8 Hz); 5.53 (1H, d, J=8 Hz); 5.23 (2H, s); 5.05 (1H, d, J=18 Hz; 4.77 (1H, d, J=18 Hz); 1.33 (9H, s).

2C N-((3RS)-1-tert-Butylcarbonylmethyl-2,3,-dihydro-2-oxo-5-phenyl-1H-1,4-benzodiazepin-3-yl)-N'-(3-methylphenyl) urea. (Scheme 1, Step (ii))

This was prepared following the method of Example 1C using the benzodiazepine of Example 2B (700 mg, 1.45 mmol), 5% palladium-on-carbon (ca. 300 mg), and m-tolyl isocyanate (0.19 ml, 1.5 mmol). The crude product was purified by flash chromatography on silica gel (eluant EtOAc: 60–80 pet. ether 40:60 v/v), taken up in acetic acid, and lyophilised to give the title benzodiazepine as a white powder (233 mg, 33%, >97%, pure by HPLC).

$R_f$ (EtOAc: 60–80 pet. ether 40:60) 0.31.

NMR (CDCl$_3$) δ7.72 (2H, d, J=8 Hz); 7.7–7.0 (12H, m); 6.87 (1H, d, J=7 Hz); 5.73 (1H, d, J=8 Hz); 4.92 (1H, d, J=18 Hz); 4.82 (1H, d, J=18 Hz); 2.32 (3H, s); 1.26 (9H, s).

M.S. (FAB, +ve ion) m/e 483.2 (M+H).

EXAMPLE 3

N-((3RS)-1-Diethylmethylcarbonylmethyl-2,3-dihydro-2-oxo-5-phenyl-1H-1,4-benzodiazepin-3-yl)-N'(3-methylphenyl)urea. Compound 2

3A Bromomethyl Diethylmethyl Ketone (Scheme 2, Steps (i)–(iii))

To 2-ethylbutyric acid (2.09 g, 18 mmol) at 0° C. was added thionyl chloride (5.2 ml, 71.5 mmol) and the resulting mixture was allowed to warm to room temperature and stirred for 25 min. The mixture was diluted with dry THF then concentrated in vacuo at ambient temperature, azeotroping with further dry THF to remove last traces of SOCl$_2$. The residual oil was taken up in dry THF (10 ml) poured onto an ice-cold solution of CH$_2$N$_2$ (prepared from Diazald®, 9 g, 42 mmol) in Et$_2$O and the resulting mixture allowed to warm to room temperature and stirred for 90 min. The reaction was quenched with AcOH (×5), basified (5% KHCO$_3$) and extracted with EtOAc (×3). The combined organic phases were washed with water, then sat. brine, filtered (Whatman® 1 PS phase separator) and concentrated in vacuo. The crude oil was purified by flash chromatography on silica gel (eluant EtOAc: 40–60 pet. ether, 5:95 v/v) to give diazomethyl diethylmethyl ketone as a pale yellow liquid (261 mg, 1.86 mmol). To a solution of this diazoketone in EtOAc (10 ml) at room temperature was added a saturated solution of HBr in EtOAc portionwise until no more nitrogen was evolved. The reaction was basified (5% KHCO$_3$) and extracted with EtOAc (×2). The combined organic phases were washed with water, sat. brine, filtered (Whatman® 1 PS phase separator) and concentrated in vacuo. The crude material was purified by flash chromatography on silica gel (eluant gradient of EtOAc: 40–60 pet. ether, 4:96 to 10:90 v/v) to give the title ketone as a pale brown mobile oil (268 mg, 7.7%).

NMR (CDCl$_3$) (for the major rotamer 88.8%). δ3.95 (2H, s); 1.56–1.46 (4H, m); 2.75–2.65 (1H, m); 0.91–0.85 (6H, m).

3B (3RS)-3-Benzyloxycarbonylamino-1-diethylmethylcarbonylmethyl-2,3-dihydro-5-phenyl-1H-1,4-benzodiazepin-2-one (Scheme 1, Step (i))

This was prepared following the method of Example IB using the Bock benzodiazepine (3.56 mg, 0.925 mmol), sodium hydride (39 mg of 80% dispersion in oil, 1.3 mmol) and the bromomethylketone of Example 3A (268 mg, 1.4 mmol). The crude product was purified by flash chromatography on silica gel (eluant EtOAc: 40–60 pet. ether 25:85 v/v) to give the title benzodiazepine as a colourless oil (351 mg).

$R_f$ (EtOAc: 40–60 pet. ether 40:60) 0.35.

NMR (CDCl$_3$) δ7.64–7.13 (14H, m); 6.67 (1H, d, J=8.25 Hz); 5.43 (1H, d, J=8.25 Hz); 5.27 (2H, s); 5.15 (1H, d, J=18 Hz); 4.78 (1H, d, J=18 Hz); 2.45–2.35 (1H, m); 1.76–1.42 (4H, m) 0.90–0.85 (6H, m).

3C N-((3RS)-1-Diethylmethylcarbonylmethyl-2,3-dihydro-2-oxo-5-phenyl-1H-1,4-benzodiazepin-3-yl)-N'-(3-methylphenyl)urea. (Scheme 1, Step (ii))

This was prepared following the method of Example 1C using the benzodiazepine of Example 3B (351 mg, 0.68 mmol), 5% palladium-on-carbon (350 mg) and m-tolyl isocyanate (87 μl 0.71 mmol). The crude product was purified by flash chromatography on silica gel (eluant EtOAc: 40–60 pet. ether 35:65 v/v) to give the title compound as a white solid (229 mg, 68%, >99% pure by HPLC).

$R_f$ (EtOAc: 40–60 pet. ether 40:60) 0.24.

NMR (CDCl$_3$) δ7.66–6.80 (15H, m); 5.66 (1H, d, J=8 Hz); 4.73 (1H, d, J=18 Hz); 4.64 (1H, d, J=18 Hz); 2.49–2.31 (1H, m); 2.26 (3H, s); 1.71–1.39 (4H, m); 0.86–0.81 (6H, m).

M.S. (FAB, +ve ion) m/e 497.3 (M+H).

EXAMPLE 4

N-((3RS)-1-Cyclopentylcarbonylmethyl-2,3-dihydro-2-oxo-5-phenyl-1H-1,4-benzodiazepin-3-yl)-N'-(3-methylphenyl)urea. Compound 4

4A Bromomethyl Cyclopentyl Ketone (Scheme 2, Steps (i)–(iii))

This was prepared following the method of Example 3A. The intermediate diazoketone was prepared from cyclopentanecarboxylic acid (2.05 g, 18 mmol), thionyl chloride (5.2 ml, 72 mmol) and CH$_2$N$_2$ (generated from Diazald® 9g, 42 mmol) and purified by flash chromatography on silica gel (eluant EtOAc: 40–60 pet. ether 15:85 v/v). The diazoketone was subsequently treated with a saturated solution of HBr in EtOAc. Flash chromatography on silica gel (eluant gradient EtOAc: 40–60 pet. ether 4:96 to 10:90 v/v) afforded the title ketone as a pale brown mobile oil (1.29 g, 37%).

NMR (CDCl$_3$) δ3.99 (2H, s), 3.18 (1H, g, J=8 Hz), 1.93–1.56 (8H, m).

4B (3RS)-3-Benzyloxycarbonylamino-1-cyclopentylcarbonylmethyl-2,3-dihydro-5-phenyl-1H-1,4-benzodiazepin-2-one. (Scheme 1, Step (i))

This was prepared following the method of Example 1B, using the Bock benzodiazepine (578 mg, 1.5 mmol), sodium hydride (63 mg of an 80% dispersion in oil, 2.1 mmol) and the bromomethylketone of Example 4A (431 mg, 2.25 mmol). The crude product was purified by flash chromatography on silica gel (eluant EtOAc: 40–60 pet. ether 30:70 v/v) to afford the title compound as a colourless crystalline solid (682 mg, 88.5%).

$R_f$ (EtOAc: 40–60 pet. ether, 40:60) 0.25.

NMR (CDCl$_3$) δ7.64–7.17 (14H, m); 6.60 (1H, d, J=8.25 Hz); 5.42 (1H, d, J=8.25 Hz); 5.14 (2H, s); 4.78 (1H, d, J=17.8 Hz); 4.63 (1H, d, J=17.8 Hz); 2.92 (1H, q, J=8 Hz); 1.85–1.55 (8H, m).

4C N-((3RS)-1-Cyclopentylcarbonylmethyl-2,3-dihydro-2-oxo-5-phenyl-1H-1,4-benzodiazepin-3-yl)-N'-(3-methylphenyl)urea. (Scheme 2, Step (ii))

This was prepared following the method of Example 1C using the benzodiazepine of Example 4B (680 mg, 1.32 mmol), 5% palladium-on-carbon (600 mg) and m-tolyl isocyanate (169 μl, 1.39 mmol). The crude product was purified by flash chromatography on silica gel (eluant EtOAc: 40–60 pet. ether 35:65 v/v) to give the title compound (463 mg, 71%).

The title compound was re-crystallised from hot methanol to give 161.8 mg of crystalline solid (>99% pure by HPLC).

$R_f$ (EtOAc: 40–60 pet. ether, 40:60) 0.16.

NMR (CDCl$_3$) δ7.66–6.80 (15H, m); 5.65 (1H, d, J=8 Hz); 4.74 (1H, d, J=18 Hz); 4.67 (1H, d, J=18 Hz); 2.95–2.83 (1H, m); 2.28 (3H, s); 1.90–1.53 (6H, m).

M.S. (FAB +ve ion) m/e 495.2 (M+H).

EXAMPLE 5

N-((3RS)-1-Cycloheptylcarbonylmethyl-2,3-dihydro-2-oxo-5-phenyl-1H-1,4-benzodiazepine-3-yl)-N'-(3-methylphenyl)urea. Compound 6

5A Bromomethyl Cycloheptyl Ketone (Scheme 2, Steps (i)–(iii))

This was prepared following the method of Example 3A. The intermediate diazoketone was prepared from cycloheptanecarboxylic acid (3 g, 21 mmol), thionyl chloride (6.24 ml, 84 mmol) and CH$_2$N$_2$ (generated from Diazald® 12 g, 56 mmol) and purified by flash chromatography on silica gel (eluant EtOAc: 40–60 pet. ether, 10:90 v/v). The diazoketone was subsequently treated with a saturated solution of HBr in EtOAc. Flash chromatography on silica gel (eluant gradient EtOAc: 40–60 pet. ether, 5.95 to 10:90 v/v) gave the title ketone as a brown oil (1.8 g, 8.22 mmol, 39%).

NMR (CDCl$_3$) δ3.98 (2H, s); 2.95–2.85 (1H, m); 1.93–1.50) (12H, m).

5B (3RS)-3-Benzyloxycarbonylamino-1-cycloheptylcarbonylmethyl-2,3-dihydro-5-phenyl-1H-1,4-benzodiazepin-2-one. (Scheme 1, Step (i))

This was prepared following the method of Example 1B, using the Bock benzodiazepine (578 mg, 1.5 mmol), sodium hydride (63 mg of an 80% dispersion in oil, 2.1 mmol) and the bromomethylketone of Example 5A (493 mg, 2.25 mmol). Reaction was complete after 30 min.

The crude product was purified by flash chromatography on silica gel (eluant EtOAc: 40–80 pet. ether, 40:60 v/v) to afford the title compound as a colorless crystalline solid (764 mg, 93%).

R$_f$ (EtOAc: 40–60 pet. ether 40:60) 0.3.

NMR (CDCl$_3$) δ7.64–7.13 (14H, m); 6.64 (1H, d, J=8.25 Hz); 5.42 (1H, d, J=8.25 Hz); 5.14 (2H, s), 4.79 (1H, d, J=17.5 Hz); 4.63 (1H, d, J=17.5 Hz); 165–2.65 (1H, m); 1.93–1.28 (12H, m).

5C N-((3RS)-1-Cycloheptylcarbonylmethyl-2,3-dihydro-2-oxo-5-phenyl-1H-1,4-benzodiazepin-3-yl)-N'-(3-methylphenyl)urea. (Scheme 1, Step (ii))

This was prepared following the method of Example 1C using the benzodiazepine of Example 5B (787 mg, 1.5 mmol), 5% palladium-on-carbon (600 mg), and m-tolyl isocyanate (0.20 ml, 1.58 mmol). The crude product was purified by flash chromatography on silica gel (eluant EtOAc: 40–60 pet. ether 30:70 v/v) to afford the title compound as a white solid (53.6 mg, 10%, >98% pure by HPLC).

R$_f$ (EtOAc: 40–60 pet. ether 40:60) 0.27.
M.S. (FAB, +ve ion) m/e 523.3 (M+H).

EXAMPLE 6

N-((3RS)-1-Cycloheptylcarbonylmethyl-2,3-dihydro-2-oxo-5-phenyl-1H-1,4-benzodiazepin-3-yl)-N'-(3-chlorophenyl)urea. Compound 7 (Scheme 1, Step (ii))

This was prepared following the method of Example 1C using the benzodiazepine of Example 5B (764 mg, 1.41 mmol), 5% palladium-on-carbon (600 mg) and m-chlorophenyl isocyanate (180 μl, 148 mmol). The crude product was purified by re-crystallisation from hot EtOAc to give the title compound as a white crystalline solid (379 mg, 69.83%) (>99% pure by HPLC).

NMR (CDCl$_3$) δ7.68–6.89 (15H, m); 5.64 (1H, d, J=8 Hz); 4.74 (1H, d, J=18 Hz); 4.66 (1H, d, J=18 Hz); 2.60–2.52 (1H, m); 1.92–1.22 (12H, m).

M.S. (FAB +ve ion) m/e 543.1 (M+H).

EXAMPLE 7

N-((3RS)-1-Cyclohexylcarbonylmethyl-2,3-dihydro-2-oxo-5-phenyl-1H-1,4-benzodiazepin-3-yl)-N'-(3-methylphenyl)urea. Compound 5

7A Bromomethyl Cyclohexyl Ketone (Scheme 2, Steps (i)–(iii))

This was prepared according to the method of Example 3A. The diazoketone was prepared from cyclohexane carboxylic acid (1.92 g, 15 mmol), thionyl chloride (4.46 ml, 60 mmol) and diazomethane (generated from Diazald® 7.16 g, 33.4 mmol). Without purification the diazoketone was treated with a saturated solution of HBr in ethyl acetate until nitrogen ceased to be evolved. Chromatography on silica gel (eluant EtOAc:pet. ether 5:95) provided the title compound as a yellow oil (0.91 g, 30%).

NMR (CDCl$_3$) δ5 4.00 (2H, s); 2.75 (1H, m); 1.95–1.20 (10H, m).

7B (3RS)-3-Benzyloxycarbonylamino-1-cyclohexylcarbonylmethyl-2,3-dihydro-5-phenyl-1H-1,4-benzodiazepin-2-one. (Scheme 1, Step (i))

This was prepared following the method of Example 1B using the Bock benzodiazepine (385 mg, 1.0 mmol), sodium hydride (42 mg, 80% dispersion in oil, 1.4 mmol) and the bromomethyl ketone of Example 7A (308 mg, 1.5 mmol). The product was purified by flash chromatography (eluant EtOAc: 40–60 pet. ether, 35:65, v/v) to give the title compound as a colourless solid (490 mg, 96%).

R$_f$ (EtOAc: 40–60 pet. ether 40:60) 0.3.

NMR (CDCl$_3$) δ: 7.8–7.2 (14H, m); 6.65 (1H, d, J=8.2 Hz); 5.42 (1H, d, J=8.2 Hz); 5.18 (2H, s); 4.72 (2H, d, J=7.5 Hz); 4.61 (2H, d, J=7.5 Hz); 2.40 (1H, m); 1.9–1.0 (10H, m).

7C N-((3RS)-1-Cyclohexylcarbonymethyl-2,3-dihydro-2-oxo-5-phenyl-1H-1,4-benzodiazepin-3-yl)-N'-(3-methylphenyl)urea. Scheme 1, Step (ii))

This was prepared following the method of Example 1C using the benzodiazepine of Example 7B (480 mg, 0.945 mmol), 5% palladium-on-carbon (ca. 400 mg) and m-tolyl isocyanate (0.130 ml, 1 mmol). The crude product was purified by flash chromatography (eluant EtOAc: 40–60 petrol, 35:65, v/v) and by crystallisation from ethyl acetate/petrol to provide the title benzodiazepine as a colourless solid (245 mg, 52%, >98% pure by HPLC).

R$_f$ (EtOAc: 40–60 pet. ether 40:60) 0.32.

NMR (CDCl$_3$) δ7.7 (2H, d, J=8 Hz); 7.65–7.00 (12H, m); 6.88 (1H, d, J=7 Hz); 5.62 (1H, d, J=8 Hz); 4.67 (2H, s); 2.39 (1H, m); 2.21 (3H, s); 1.9–0.8 (10H, m).

M.S. (FAB +ve ion) m/e 509 (M+H).

EXAMPLE 8

N-((3RS)-2,3-Dihydro-2-oxo-5-phenyl-1-((2S)-2-pyrrolidylcarbonylmethyl)-1H-1,4-benzodiazepin-3-yl)-N'-(3-methylphenyl)urea Hydrochloride. Compound 15

8A (2S)-1-tert-Butyloxycarbonyl-2-pyrrolidyl Diazomethyl Ketone (Scheme 2, Steps (i)–(ii))

To a solution of Boc-L-proline (5.5 g, 25.6 mmol) and N-methylmorpholine (3.1 ml, 28.2 mmol) in dry THF (80 ml) at −20° C. was added isobutyl chloroformate (3.5 ml, 27.1 mmol). The mixture was stirred at −10° C. for 1 hr and then poured into an ice-cold solution of CH$_2$N$_2$ (prepared from Diazald®, 18 g, 84 mmol) in Et$_2$O, and the resulting mixture was allowed to warm to room temperature over 2 hrs. Excess CH₂N₂ was quenched with glacial AcOH and the resulting solution then basified with 5% aqueous KHCO₃ solution and extracted with EtOAc. The organic phase was separated, washed with water and brine, filtered (Whatman® 1 PS phase separator), and concentrated in vacuo. The crude product was purified by flash chromatography on silica gel (eluant EtOAc: 40–60 pet. ether 35:65 v/v) to give the title compound used immediately in the next stage.

R$_f$ (EtOAc: 40–60 pet. ether 30:70) 0.12.

8B (2S)-1-tert-Butyloxycarbonyl-2-pyrrolidyl Bromomethyl Ketone. (Scheme 2, Step (iii))

To a stirred solution of the diazoketone of Example 8A in EtOAc was added a saturated solution of HBr in EtOAc dropwise until no more nitrogen was evolved. The resulting solution of bromomnethylketone was washed successively with saturated KHCO₃, water and brine, filtered (Whatman® 1 PS phase separator), and concentrated in vacuo. The crude product was purified by flash chromatography on silica gel (eluant EtOAc: 40–60 pet. ether 15:85 v/v) to give the title ketone as a brown oil (1.25 g, 17% for two steps).

R$_f$ (EtOAc: 40–60 pet. ether 20:80) 0.2.

NMR (CDCl₃) δ4.66–4.49 (1H, broad m), 4.1–4.0 (2H, broad m), 3.73–3.50 (2H, broad m), 2.40·1.67 (4H, m), 1.46 and 1.44 (9H, 2 singlets).

8C (3RS)-3-Benzyloxycarbonylamino-1-((2S)-tert-butyloxycarbonyl-2-pyrrolidylcarbonylmethyl)-2,3-dihydro-5-phenyl-1H-1,4-benzodiazepin-2-one. (Scheme 1, Step (i))

This was prepared following the method of Example 1B using the Bock benzodiazepine (1.2 g, 2.97 mmol), sodium hydride (125 mg of an 80% dispersion in oil, 4.2 mmol) and the bromomethylketone of Example 83 (1.25 g, 4.46 mmol).

The product was purified by flash chromatography on silica gel (eluant EtOAc: 40–60 pet. ether 35:65 v/v) to give the title compound (798 mg, 45%).

NMR (CDCl₃) δ7.62–7.18 (14H, m), 6.65 (1H, d, J=8 Hz), 5.42 (1H, d, J=8 Hz), 5.14 (2H, s), 4.95–4.72 (1H, m), 4.64–4.40 (1H, m), 4.38–4.28 (1H, m), 3.60–3.44 (2H, m), 2.23–1.82 (4H, m), 1.44 (9H, s).

8D N-((3RS)-1-((2S)-tert-Butyloxycarbonyl-2-pyrrolidylcarbonylmethyl)-2,3-dihydro-2-oxo-5-phenyl-1H-1,4-benzodiazepin-3-yl)-N'-(3-methylphenyl)urea. (Scheme 1, Step (iii))

This was prepared following the method of Example 1C using the benzodiazepine of Example 8C (798 mg, 1.33 mmol), 5palladium-on-carbon (ca 600 mg) and m-tolyl isocyanate (180 μl, 1,4 mmol). The crude product was purified by flash chromatography on silica gel (eluant EtOAc: 40:60 pet. ether 45:65 v/v) to give the title compound as a colourless oil (559 mg, 71.1%).

NMR (CDCl₃) δ7.65–6.81 (15H, m), 5.66 (1H, d, J=9 Hz), 4.97–4.56 (2H, m), 4.40–4.25 (1H, m), 3.56–3.38 (2H, m), 2.27 (3H, s), 2.21–1.86 (4H, m), 1.44 and 1.42 (9H, 2 singlets).

8E N-((3RS)-2,3-Dihydro-2-oxo-5-phenyl-1-((2S)-2-pyrrolidylcarbonylmethyl-1H-1,4-benzodiazepin-3-yl)-N'-(3-methylphenyl)urea Hydrochloride The Boc-protected compound of Example 8D (559 mg, 0.95 mmol) was dissolved in HCl-dioxan (4M, XS) and stirred at room temperature for 30 min. The solution was concentrated in vacuo, azeotroping twice with dry toluene to remove last traces of dioxan. The residue was as crystallised from chloroform/ether to provide the title salt as a white solid (245 mg, 48.5%, >98% pure by HPLC).

R$_f$ (CHCl₃:MeOH:AcOH, 12:2:1) 0.32.

M.S. (FAB, +ve ion) m/e 495.2 (M+H).

EXAMPLE 9

N-((3RS)-1-((2S)-1-Acetyl-2-pyrrolidylcarbonylmethyl-2,3-dihydro-2-oxo-5-phenyl-1H-1,4-benzodiazepin-3-yl)-N'-(3-methylphenyl)urea. Compound 17

To a solution of the benzodiazepine salt of Example 8E (166 mg, 0.32 mmol) in CH₂Cl₂ at 0° C. under an atmosphere of nitrogen was added DIEA (0.11 ml, 0.63 mmol) followed by acetylchloride (22 μl, 0.32 mmol). Reaction was complete after 10 mins. The mixture was concentrated in vacuo and the residue partitioned between CH₂Cl₂ and 0.3 M KHSO₄. The organic phase was separated, dried (Na₂SO₄), filtered (Whatman® 1 PS phase separator) and evaporated in vacuo. The crude product was purified by flash chromatography on silica gel (eluant EtOAc:AcOH, 100:2 v/v) to give a white solid which was taken up in acetonitrile/water and lyophilised to give the title compound as a white powder (148 mg, 89%, >99% pure by HPLC).

NMR (CDCl₃) δ7.91–6.95 (14H, m), 6.76 (1H, m), 5.68–5.62 (1H, m), 4.94–4.43 (3H, m), 3.48–3.35 (2H, m), 2.35 (1H, s), 2.23 (3H, s), 2.1–1.79 (6H, m).

M.S. (FAB, +ve ion) m/e=538.3 (M+H).

EXAMPLE 10

N-((3RS)-2,3-Dihydro-2-oxo-5-phenyl-1-((2R)-2-pyrrolidylcarbonylmethyl)-1H-1,4-benzodiazepin-3-yl)-N'(3-methyl-phenyl)urea Hydrochloride. Compound 14

10A (2R)-1-tert-Butyloxycarbonyl-2-pyrrolidyldiazomethyl Ketone. (Scheme 2, Steps (i)–(iii))

This was prepared following the method of Example 8A using, Boc-D-proline (4 g, 19.4 mmol), NMM (2.1 ml, 19.4 mmol) and isobutyl chloroformate (2.7 ml, 20.5 mmol). Flash chromatography on silica gel (eluant EtOAc: 40–60 pet. ether 35:65 v/v) afforded the title compound as an oil (1.68 g, 38%).

NMR (CDCl₃) δ5.45 (1H, d, J=23 Hz), 4.24 (1H, d, J=23 Hz), 3.51–3.43 (2H, m), 2.19–1.83 (4H, m), 1.47 and 1.43 (9H, 2 singlets).

10B (2R)-1-tert-Butyloxycarbonyl-2-pyrrolidyl Bromomethyl Ketone. (Scheme 2, Step (iii))

This was prepared following the method of Example 8B using the diazoketone of Example 10A (1.68 g, 7.4 mmol). The crude product was purified by flash chromatography on silica gel (eluant EtOAc: 40–60 pet. ether 20:80 v/v) to give the title ketone as a brown oil (986 mg, 47.5%).

R$_f$ (EtOAc: 40–60 pet. ether 20:80) 0.19.

10C (3RS)-3-Benzyloxycarbonylamino-1-((2R)-1-tert-butyloxycarbonyl-2-pyrrolidylcarbonylmethyl-2,3-dihydro-5-phenyl-1H-1,4-benzodiazepin-2-one. (Scheme 1, Step (i))

This was prepared following the method of Example 1B using the Bock benzodiazepine (950 mg, 2.35 mmol), sodium hydride (99 mg of an 80% dispersion in oil, 3.29 mmol) and the bromomethylketone of Example 10B (986 mg, 3.57 mmol). The product was purified by flash chromatography on silica gel (eluant EtOAc: 40–60 pet. ether 40:60 v/v) to give the title compound (1.3 g, 92%).

NMR (CDCl₃) δ7.62–7.18 (14H, m), 6.68 (1H, d, J=8 Hz), 5.43 (1H, d, J=8 Hz), 5.14 (2H, s), 5.09–4.8 (1H, m), 4.65–4.4 (1H, m), 4.37–4.27 (1H, m), 3.49–3.44 (2H, m), 2.22–1.85 (4H, m), 1.43 (9H, s).

10D N-((3RS)-1-((2R)-1-tert-Butyloxycarbonyl-2-pyrrolidylcarbonylmethyl)-2,3-dihydro-2-oxo-5-phenyl- 1H-1,4-benzodiazepin-3-yl)-N'-(3-methylphenyl)urea. (Scheme 1 Step (ii))

This was prepared following the method of Example 1C using the benzodiazepine of Example 10C (394 mg, 0.65 mmol), 5! palladium-on-carbon (ca 200 mg) and m-tolyl isocyanate (88 μl, 0.68 mmol). The crude product was purified by flash chromatography on silica gel (eluant EtOAc: 40–60 pet. ether 40–60 v/v) to afford the title compound as a crystalline solid (175 mg, 65%).

NMR (CDCl$_3$) δ7.63–7.0 (13H, m), 6.97–6.78 (1H, m), 5.64 (1H, d, J=10 Hz), 4.8–4.7 (2H, m), 4.37–4.08 (1H, m), 3.48–3.37 (2H, m), 2.24 (3H, s), 2.05 (3H, s), 2.2–1.76 (4H, m), 1.49–1.34 (9H, 2 singlets).

10E N-((3RS)-2,3-Dihydro-2-oxo-5-phenyl-1-((2R)-2-pyrrolidylcarbonylmethyl)-1H-1,4-benzodiazepin-3-yl)-N'-(3-methylphenyl)urea Hydrochloride This was prepared following the method of Example 8E using the benzodiazepine of Example 10D (175 mg, 0.3 mmol). The crude product was taken up in AcOH and lyophilised to give the title compound, without purification, as a white powder (125 mg, 78%, >99% pure by HPLC).

M.S. (FAB, +ve ion) m/e=496.2 (M+H).

EXAMPLE 11

(N-((3RS)-1-((2R)-1-Acetyl-2-pyrrolidylcarbonylmethyl)-2,3-dihydro-2-oxo-5-phenyl-1H-1,4-benzodiazepin-3-yl)-N'-(3-methylphenyl)urea. Compound 16

This was prepared following the method of Example 9 using the benzodiazepine salt of Example 10E (244 mg, 0.46 mmol), DIEA (0.16 ml, 0.92 mmol) and acetyl chloride (32.7 μl, 0.46 mmol). The crude product was purified by flash chromatography on silica gel (eluant EtOAc:AcOH, 100:2 v/v) to give the pure product which was then taken up in glacial AcOH and lyophilised to give the title compound as a white powder (173 mg, 70%, >99% pure by HPLC).

M.S. (FAB, +ve ion) m/e=538.3 (M+H).

EXAMPLE 12

N-((3RS)-1-((2RS)-2-Cyclopentyl-2-hydroxyethyl)-2,3-dihydro-2-oxo-5-phenyl-1H-1,4-benzodiazepine-3-yl)-N'-(3-methylphenyl)urea. Compound 18 and

EXAMPLE 13

N-((3RS)-1-(2SR)-2-Cyclopentyl-2-hydroxyethyl)-2,3-dihydro-2-oxo-5-phenyl-1H-1,4-benzodiazepine-3-yl)-N'-(3-methylphenyl)urea. Compound 19

To a solution of the benzodiazepine of Example 4C (240 mg, 0.49 mmol) in ethanol at 0° C. was added sodium borohydride (29 mg, 0.76 mmol). The resulting mixture was stirred at 0° C. for 30 mins and then at room temperature for a further 90 mins. The mixture was concentrated in vacuo and the residue flash chromatographed on silica gel (eluant EtOAc: 40–60 pet. ether 35:65 v/v) to afford two compounds. Each was taken up in acetonitrile/water and lyophilised to give the title compounds.

Less polar product: 66 mg, 26% >98% pure by HPLC

R$_f$ (EtOAc: 40–60 pet. ether 35:65) 0.14

NMR (CDCl$_3$) δ7.74–6.90 (14H, m), 6.78 (1H, d, J=8 Hz), 5.62 (1H, d, J=8 Hz), 4.41–4.34 (1H, m), 3.65–3.55 (2H, m), 2.22 (3H, s), 1.67–1.11 (9H, m).

M.S. (FAB, +ve ion) 497.2 (M+H)

More polar product: 95 mg, 38%, >96% pure by HPLC

R$_f$ (EtOAc: 40–60 pet. ether 35:65) 0.10

NMR (CDCl$_3$) δ7.73–7.0 (14H, m), 6.87–6.78 (1H, m), 5.59–5.56 (1H, d, J=8 Hz), 4.05–3.70 (3H, m), 2.24 (3H, s), 1.76–1.14 (9H, m).

M.S. (FAB, +ve ion) 497.0 (M+H)

EXAMPLE 14

N-((3RS)-1-Cyclopentylcarbonylmethyl-2,3-dihydro-2-oxo-5-(2-pyridyl)-1H-1,4-benzodiazepin-3-yl)-N'-(3-methylphenyl)urea. Compound 8

14A (3RS)-3-Benzyloxycarbonylamino-1-cyclopentylcarbonylmethyl-2,3-dihydro-2-oxo-5-(2-pyridyl)-1H-1,4-benzodiazepin-2-one. (Scheme 1, Step (i))

To a stirred solution of (3RS)-3-benzyloxycarbonylamino-2,3-dihydro-5-(2-pyridyl)-1H-1,4-benzodiazepin-2-one (R. M. Freidinger et al. Eur. Pat. No. 0 434 364 A2) (388 mg, 1 mmol) in DMF (5 ml), cooled to −10° C. under N$_2$, was added sodium hydride (42 mg of 80% dispersion in oil, 1.4 mmol). The mixture was stirred at −10° C. for 30 min, when a solution of the bromomethyl ketone of Example 4A (250 mg, 1.4 mmol) was added. The resulting mixture was allowed to warm to room temperature over 1 hr with stirring, then poured into dilute aqueous HCl (100 ml). The mixture was extracted twice with EtOAc and the organic extracts washed with brine, filtered (Whatman® 1 PS phase separator) and concentrated in vacuo. The crude product was purified by flash chromatography on silica gel (eluant EtOAc/40–60 pet. ether 90:10 v/v) to give the title compound as a colourless solid (426 mg, 86%).

R$_f$ (EtOAc) 0.35

NMR (CDCl$_3$) δ8.62 (1H, d, J=8 Hz), 8.17 (1H, d, J=8 Hz), 7.78 (1H, t, J=8 Hz), 7.50 (1H, t, J=8 Hz), 7.4–7.15 (9H, m), 6.76 (1H, d, J=8.5 Hz), 5.51 (1H, d, J=8.5 Hz), 5.16 (2H, m), 4.80 (1H, d, J=17.5 Hz), 4.42 (1H, d, J=17.5 Hz), 2.92 (1H, m), 1.9–1.5 (8H, m).

14B N-((3RS)-1-Cyclopentylcarbonylmethyl-2,3-dihydro-2-oxo-5-(2-pyridyl)-1H-1,4-benzodiazepin-3-yl)-N'-(3-methylphenyl)urea. (Scheme 1, Step (ii))

The benzodiazepine of Example 14A (426 mg, 0.86 mmol) was treated with 40% HBr in acetic acid (6 ml) and the mixture stirred at room temperature for 2 hrs. The mixture was azeotroped twice with toluene and the residue partitioned between EtOAc and 1 M NaOH. The organic portion was filtered (Whatman® 1 PS phase separator), evaporated, taken up in CH$_2$Cl$_2$ (5 ml) and treated with m-tolyl isocyanate (130 μl, 0.95 mmol) at room temperature with stirring for 2 hrs. The mixture was evaporated and chromatographed (eluant EtOAc/40–60 pet. ether 70:30 v/v) to provide a yellow solid which was recrystallised from acetonitrile to give the colourless product (73 mg, 17%)

R$_f$ (EtOAc/Hexane, 60:40 v/v) 0.38

NMR (CDCl$_3$) δ8.6 (1H, d, J=6 Hz), 7.95 (1H, d, J=6 Hz), 7.6–7.0 (10H, m), 6.80(1H, d, J=8.5 Hz), 5.78 (1H, d, J=8.5 Hz), 5.10 (1H, d, J=14 Hz), 5.00 (1H, d, J=14 Hz), 2.82 (1H, m), 2.14 (3H, s), 1.90–1.50 (8H, m).

M.S. (FAB, +ve ion) m/e. 496.3 (M+H)

EXAMPLE 15

N-((3-RS)-1-Cyclopentylcarbonylmethyl-2,3-dihydro-2-oxo-5-(4-pyridyl)-1H-1,4-benzodiazepin-3-yl)-N'-(3-methylphenyl)urea. Compound 10

15A (3RS)-3-Benzyloxycarbonylamino-1-cyclopentylcarbonylmethyl-2,3-dihydro-2-oxo-5-(4-pyridyl)-1H-1,4-benzodiazepin-2-one (Scheme 1, Step (i))

A solution of (3RS)-3-benzyloxycarbonylamino-2,3-dihydro-5-(4-pyridyl)-1H-1,4-benzodiazepin-2-one (Freidinger et al. Eur. Pat. No. 0 434 364 A2) (388 mg, 1 mmol) was alkylated as described in Example 14A to provide the product as a colourless solid after chromatography (eluant EtOAc) (460 mg, 93%).

R$_f$ (EtOAc) 0.22

NMR (CDCl$_3$) δ8.62 (2H, d, J=7.5 Hz), 7.55 (3H, m), 7.4–7.1 (8H, m), 6.80 (1H, d, J=8.5 Hz), 5.42 (1H, d, J=8.5 Hz), 5.12 (2H, s), 4.72 (2H, m), 2.85 (1H, m), 1.9–1.4 (8H, m).

15B N-((3RS)-1-Cyclopentylcarbonylmethyl-2,3-dihydro-2-oxo-5-(4-pyridyl)-1H-14-benzodiazepin-3-yl)-N'-(3-methylphenyl)urea. (Scheme 1, Step (ii))

The benzodiazepine of Example 15A (375 mg, 0.724 mmol) was converted to the urea as described in Example 14B. The product was chromatographed (eluant CHCl$_3$/MeOH/AcOH 200:2:1 v/v/v) to give a white solid (59 mg, 16%).

R$_f$ (EtOAc) 0.30

NMR (CDCl$_3$) δ8.62 (2H, d, J=7.5 Hz), 7.7–7.0 (11H, m), 6.8 (1H, m), 5.62 (1H, d, J=8.5 Hz), 4.85 (1H, d, J=16 Hz), 4.60 (1H, d, J=16 Hz), 2.80 (1H, m), 2.15 (3H, s), 1.8–1.4 (8H, m).

M.S. (FAB, +ve ion) m/e 496.2 (M+H)

EXAMPLE 16

N-((3RS)-1-Cyclopentylcarbonylmethyl-2,3-dihydro-2-oxo-5-phenyl-1H-1,4-benzodiazepin-3-yl)-N'-(3-carboxyphenyl)urea. urea. Compound 11

16A (3RS)-3-p-Nitrobenzyloxycarbonylamino-1-cyclopentylcarbonylmethyl-2,3-dihydro-2-oxo-5-phenyl-1H-1,4-benzodiazepin-2-one. (Scheme 3, Step (i))

The benzodiazepine of Example 4B (2.04 g, 4.13mmol) was hydrogenated over 5% palladium-on-carbon catalyst (1.2 g) as described in Example 1C. The amine was taken up in dry THF (15 ml) and triethylamine (0.626 ml, 4.5 mmol) and the solution cooled to 0° C. The stirred mixture was treated with p-nitrophenyl chloroformate (0.91 g, 4.5 mmol) and stirred at room temperature for 1 hr, then evaporated and flash chromatographed (eluant EtOAc/Hexane 40:60 v/v) to provide the product as a yellow solid (675 mg, 32%).

R$_f$ (EtOAc/Hexane, 60:40 v/v) 0.52

NMR (CDCl$_3$) δ8.2 (2H, d, J=8 Hz), 7.6–7.0 (12H, m), 5.42 (1H, d, 8.5 Hz), 4.82 (1H, d, J=16.5 Hz), 4.62 (1H, d, J=16.5 Hz), 2.97 (1H, m), 1.9–1.4 (8H, m).

16B N-((3RS)-1-cyclopentylcarbonylmethyl-2,3-dihydro-2-oxo-5-phenyl-1H-1,4-benzodiazepin-3-yl)-N'-(3-carboxyphenyl)urea. (Scheme 3, Step (ii))

To a stirred solution of the benzodiazepine of Example 16A (175 mg, 0.333 mmol) in DMF (5 ml) was added m-aminobenzoic acid (72 mg, 0.52 mmol) and triethylamine (125 μl). The mixture was stirred at 45° C. for 18 hrs, cooled and diluted with EtOAc. The mixture was washed with 0.3 M HCl and brine, then filtered (Whatman® 1 PS phase separator) and evaporated. The residue was flash chromatographed (eluant EtOAc/Hexane/acetic acid 60:40:2 v/v/v) to provide the title compound as a colourless solid (132 mg, 76%).

R$_f$ (EtOAc/Hexane/acetic acid 60:40:2 v/v/v) 0.25

NMR (CDCl$_3$) δ8.41 (1H, s), 8.37 (1H, d, J=7.5 Hz), 8.16 (1H, d, J=7.5 Hz), 7.82 (1H, s), 7.7–7.2 (12H, m), 5.65 (1H, d, J=8.5 Hz), 5.81 (1H, d, J=15 Hz), 4.66 (1H, d, J=15 Hz), 2.95 (1H, m), 1.95–1.5 (8H, m).

M.S. (FAB, +ve ion) m/e 419 (M+Na—H$_2$NC$_6$H$_4$CO$_2$H)

EXAMPLE 17

N-((3R)-1-Cyclopentylcarbonylmethyl-2,3-dihydro-2-oxo-5-phenyl-1H-1,4-benzodiazepin-3-yl)-N'-(3-methylphenyl)urea. Compound 12

The benzodiazepine of Example 4B (1.13 g, 2,3 mmol) was hydrogenated as described in Example 4C and the amine chromatographed (eluant CHCl$_3$/MeOH/AcOH 25:2:1) to provide a yellow oil. This was taken up in acetonitrile and (S)-mandelic acid (335 mg, 2.20 mmol) added to the stirred solution, followed 30 min later by 3,5-dichlorosalicylaldehyde (10 mg). After stirring overnight the resultant precipitate was collected by suction filtration and washed with cold acetonitrile, to give a white solid (680 mg, 59%).

The solid (460 mg, 0.897 mmol) was partitioned between CHCl$_3$ and 0.5 M NaOH. The organic portion was washed with brine, filtered (Whatman® 1 PS phase separator) and evaporated. The residue was taken up in CH$_2$Cl$_2$ (5 ml) and treated with m-tolyl isocyanate (110 μl, 0.852 mmol) at room temperature for 1 hr. The mixture was evaporated and chromatographed (eluant EtOAc/Hexane 40:60 v/v) to provide a colourless solid (320 mg, 76%).

R$_f$ (EtOAc/Hexane 40:60 v/v) 0.16

[α]$_D$=+100.4° (CHCl$_3$, C=0.96)

NMR and M.S. identical to Example 4C.

EXAMPLE 18

(N-((3S)-1-Cyclopentylcarbonylmethyl-2,3-dihydro-2-oxo-5-phenyl-1H-1,4-benzodiazepin-3-yl)-N'-(3-methylphenyl)urea. Compound 13

The benzodiazepine of Example 4B (1.98 g, 4 mmol) was hydrogenated as described in Example 4C and the amine chromatographed (Eluant CHCl$_3$/MeOH/AcOH 25:2:1) to provide a yellow oil (1.15 g, 79%). This was taken up in acetonitrile and (S)-mandelic acid (290 mg, 1.91 mmol) added and the mixture stirred at room temperature overnight. The resultant precipitate was collected by filtration (300 mg, 19%) and the filtrate evaporated and partitioned between CHCl$_3$ and 0.25 M NaOH. The organic portion was washed with brine, filtered (Whatman® 1 PS phase separator) and evaporated. The residue was taken up in acetonitrile and (R)-mandelic acid (420 mg, 2.77 mmol) added and the mixture stirred at 0° C. for 20 min, then 3,5-dichlorosalicylaldehyde (5 mg) added and stirring continued at room temperature overnight. The resulting white precipitate was collected by filtration and washed with cold acetonitrile (800 mg, 56%).

The solid (780 mg, 1.52 mmol) was partitioned between CHCl$_3$ and 0.25 M NaOH and the organic portion washed with brine, filtered (Whatman® 1 PS phase separator) and evaporated. The residue was taken up in CH$_2$Cl$_2$ (10 ml) and treated with m-tolyl isocyanate (220 μl, 1.70 mmol) at room temperature for 1 hr. The mixture was evaporated and chromatogaphed (eluant EtOAc/Hexane 40:60 v/v) to provide a colourless solid (650 mg, 87%).

R$_f$ (EtOAc/Hexane 40:60 v/v) 0.16

[α]$_D$=−96.0° (CHCl$_3$, c=1.58)

NMR and M.S. identical to Example 4C

EXAMPLE 19

N-((3R)-1-((2R)-2-Cyclopentyl-2-hydroxyethyl)-2,3-dihydro-2-oxo-5-phenyl-1H-1,4-benzodiazepin-3-yl)-N'-(3-methylphenyl)urea. Compound 20 and

EXAMPLE 20

N-((3R)-1-((2S)-2-Cyclopentyl-2-hydroxyethyl)-2,3-dihydro-2-oxo-5-phenyl-1H-1,4-benzodiazepin-3-yl)-N'-(3-methylphenyl)urea. Compound 21

The benzodiazepine of Example 17 (335 mg, 0.677 mmol) was treated with sodium borohydride in ethanol as described in Examples 12 and 13. The residue was chromatographed to afford the two title compounds (eluant EtOAc/Hexane 35:65 v/v).
Less polar product: 105 mg 31%
More polar product: 145 mg 43%
Identical to Examples 12 and 13 by T.L.C., NMR and M.S.

EXAMPLE 21

N-((3RS)-1-Cyclopentylcarbonylmethyl-2,3-dihydro-2-oxo-5-(3-pyridyl)-1H-1,4-benzodiazepin-3-yl)-N'-(3-methylphenyl)urea. Compound 9

21A 2-Nitro-α-(3-pyridyl)benzyl Alcohol 3-bromopyridine (7.90 g, 50 mmol) was taken up in dry THF (50 ml) and treated dropwise with n-butyl lithium (1.6 M solution, 32 ml, 51.2 mmol) at −100° C. (internal temp.) and the mixture stirred for 15 min at −100° C. 2-Nitrobenzaldehyde (8.25 g, 54.6 mmol) was added dropwise in a solution of THF (20 ml) and the mixture allowed to warm to 0° C. over 40 min. The mixture was quenched with water (5 ml) and then evaporated and partitioned between EtOAc and 5% $KHCO_3$. The organic portion was washed with brine, and filtered (Whatman® 1 PS phase separator) and evaporated. The residue was chromatographed (EtOAc/Hexane, 95:5 v/v) to provide a yellow solid (5.72 g, 50%)

$R_f$ (EtOAc) 0.30

NMR ($CDCl_3$) δ8.38 (1H, d, J=1.5 Hz); 8.26 (1H,m); 7.96 (2H, m); 7.70 (2H, m); 7.45 (1H, m); 7.22 (1H, m); 6.45 (1H, s).

$^{13}$C NMR ($CDCl_3$) δ148.0, 147.9, 147.6, 138.5, 138.3, 135.2, 133.6, 128.9, 128.5, 124.5, 123.5, 68.6.

21B 3-(2-Nitrobenzoyl)pyridine

Oxalyl chloride (2,3 ml, 25.8 mmol) was taken up in $CH_2Cl_2$ (40 ml) and treated dropwise with dimethyl sulphoxide (3.67 ml, 51.75 mmol) at −60° C. over 10 min. A solution of the alcohol of Example 21A (5.22 g, 22.7 mmol) was added in $CH_2Cl_2$ (5 ml), followed by triethylamine (15.8 113.3 mmol). The mixture was stirred at −60° C. for 5 min and then at room temperature for 12 hr. The mixture was diluted with EtOAc and washed with 5% $KHCO_3$ and brine, filtered (Whatman® 1 PS phase separator) and evaporated. The residue was chromatographed (EtOAc/Hexane, 90:10 v/v) to provide a yellow solid (3.25 g, 63%).

$R_f$ (EtOAc) 0.38

NMR ($CDCl_3$) δ8.90 (1H, d, J=1.5 Hz); 8.82 (1H, m). 8.31 (1H, d, J=8 Hz); 8.18 (1H, dd, $J_1$=8 Hz, $J_2$=1.5 Hz); 7.80 (2H, m); 7.50 (2H, m).

$^{13}$C NMR ($CDCl_3$) δ192.0, 153.9, 150.3, 146.3, 136.0, 134.9, 134.4, 131,4, 131.0, 128.5, 124.6, 123.6.

21C 3-(2-Aminobenzoyl)pyridine

The ketone of Example 21B (1.83 g, 8.06 mmol) was taken up in ethanol/water (1:1, v/v, 10 ml) and treated with iron powder (2.78 g, 48 mmol). The mixture was heated under reflux and then conc. HCl (0.17 ml) added in ethanol/water (1:1, v/v, 2 ml). Heating was maintained for a further 1 hr, then the mixture cooled and filtered and evaporated. The residue was partitioned between 0.5 M NaOH and $CHCl_3$ and the organic portion washed with brine, filtered (Whatman® 1 PS phase separator) and chromatographed (EtOAc/Hexane, 65:35 v/v) to provide a yellow solid (700 mg, 44%).

$R_f$ (EtOAc) 0.45

NMR ($CDCl_3$) δ8.72 (1H, d, J=1.5 Hz); 8.60 (1H, d, J=7 Hz); 7;80 (1H, m); 7.20 (3H, m); 6.60 (1H, d, J=8 Hz); 6.48 (1H, t, J=8 Hz); 6.12 (2H, br.s).

$^{13}$C NMR ($CDCl_3$) δ196.3, 151.3, 149.6, 149.5, 136.4, 135.7, 134.5, 133.5, 123.0, 117.2, 115.6, 115.4.

21D (3RS)-3-Benzyloxycarbonylamino-2,3-dihydro-5-(3-pyridyl)-1H-1,4-benzodiazepin-2-one The title compound was prepared from the amine of Example 21C (700 mg, 3.57 mmol), using the method of Freidinger et al. (Eur. Pat. No. 0 434 364 A2), as a white solid (142 mg, 10%).

$R_f$ (EtOAc) 0.2

NMR ($CDCl_3$) δ10.12 (1H, s); 8.6 (2H, m); 7.83 (1H, d, J=7 Hz); 7.4–7.0 (5H, m); 6.76 (1H, d, J=8 Hz); 5.25 (1H, d, J=8 Hz); 5.08 (2H, s).

21E (3RS)-3-Benzyloxycarbonylamino-1-cyclolentylcarbonylmethyl-2,3-dihydro-5-(3-pyridyl)-1H-1,4-benzodiazepin-2-one. (Scheme 1, Step (i))

The benzodiazepine of Example 21D (142 mg, 0.35 mmol) was alkylated with the bromomethyl ketone of Example 4A (90 mg, 0.49 mmol) using the method described in Example 1B. The title compound was obtained as a white solid after chromatography (EtOAc/Hexane, 95:5 v/v) (164 mg, 96%).

$R_f$ (EtOAc) 0.28

NMR ($CDCl_3$) δ8.68 (1H, s); 8.58 (1H, d, J=1.5 Hz); 7.98 (1H, d, J=8 Hz); 7.88 (1H, s); 7.45 (1H, m); 7.3–7.1 (3H, m); 6.62 (1H, d, J=8 Hz); 5.37 (1H, d, J=8 Hz); 5.06 (2H, s); 4.63 (2H, s); 2.80 (1H, m); 1.8–1.4 (8H, m).

21F N-((3RS)-1-Cyclopentylcarbonylmethyl-2,3-dihydro-2-oxo-5-(3-pyridyl)-1H-1,4-benzodiazepin-3-yl))-N'-(3-methylphenyl)urea. (Scheme 1, Step (ii)

The benzodiazepine of Example 21E (160 mg, 0.32 mmol) was taken up in $CH_2Cl_2$ (2 ml) at −70° C. and treated dropwise with stirring with boron tribromide (1.0 M in $CH_2Cl_2$, 2.0 ml). The mixture was allowed to warm to room temperature over 1 hour and stirring continued for a further 3 hrs. The solution was then quenched with water and then partitioned between EtOAc and 1M NaOH. The organic portion was washed with brine, filtered (Whatman® 1 PS phase separator) and evaporated. The residue was taken up in $CH_2Cl_2$ (3 ml) and treated with m-tolyl isocyanate (45 μl, 0.35 mmol) at room temperature for 1 hr. The mixture was evaporated and chromatographed (EtOAc/Hexane, 90:1 0, v/v) to provide the title compound as a white solid (70 mg, 44%).

$R_f$ (EtOAc) 0.28

NMR ($CDCl_3$) δ8.88 (1H, s); 8.80 (1H, d, J=1.5 Hz); 8.30 (1H, d, J=8 Hz); 7.70–7.20 (10H, m); 6.96 (1H, m); 5.80 (1H, d, J=8 Hz); 5.01 (1H, d, J=14 Hz); 4.80 (1H, d, J=14 Hz); 3.02 (1H, m); 2.41 (3H, s); 2.0–1.65 (8H, m).

M.S. (FAB) $[M+H]^+$=496.3

EXAMPLE 22

N-((3RS)-1-Cyclopentylcarbonylmethyl-2,3-dihydro-2-oxo-5-(2-pyridyl)-1H-1,4-benzodiazepin-3-yl)-N'-(3-carboxyphenyl)urea. Compound 34

22A N-((3RS)-1-Cyclopentylcarbonylmethyl-2,3-dihydro-2-oxo-5-(2-pyridyl)-1H-1,4-benzodiazepin-3-yl)-N'(3-methoxycarbonylphenyl)urea. (Scheme 1, Step (ii))

The benzodiazepine of Example 14A (180 mg, (0.363 mmol) was taken up in dichloromethane (3 ml) and cooled to −70° C. under nitrogen. Boron tribromide (2.2 ml of 1 M solution in $CH_2Cl_2$) was added dropwise and the mixture stirred over 1 hr during which the cold bath expired, and then for a further 2 hrs at room temperature. The mixture was quenched with iced water and then diluted with ethylacetate and washed with 1M NaOH. The organic portion was washed with brine, filtered (Whatman® 1 PS phase separator) and evaporated to leave a brown oil.

Methyl(3-amino)benzoate (151 mg, 1 mmol) in $CH_2Cl_2$ (2 ml) at −20° C. under $N_2$ was treated with triphosgene (110 mg, 0.37 mmol) and pyridine (81 µl mmol). The mixture was stirred at −20° C. for 30 min then a further portion of pyridine (81 µl, 1 mmol) added, followed by the amine from above. The mixture was stirred at room temperature 1 hr, then evaporated and partitioned between EtOAc and 5% KHCO$_3$. The organic portion was washed with 10% citric acid and brine, filtered (Whatman® 1 PS phase separator) and evaporated and the residue chromatographed (eluant EtOAc) to provide an off-white solid (95 mg, 49%).

R$_f$ EtOAc 0.28.

NMR (CDCl$_3$) δ8.60 (d, 1H, J=2 Hz); 7.10–8.10 (M, 13H); 5.65 (d, 1H, J=8 Hz); 4.62 (m, 2H); 3.8 (s, 3H); 2.95 (m, 1H); 1.4–1.95 (m, 8H)

22B N-((3RS)-1-Cyclopentylcarbonylmethyl-2,3-dihydro-2-oxo-5-(2-pyridyl)-1H-1,4-benzodiazepin-3-yl)-N'-(3-carboxyphenyl)urea The benzodiazepine of Example 22A (95 mg, 0.176 mmol) was taken up in dioxan water (1:1, v/v, 2 ml) and treated with LiOH-H$_2$O (12 mg, 1.5 eq) at room temperature for 16 hrs. The mixture was evaporated and partitioned between CHCl$_3$ and 10% citric acid. The organic portion was washed with brine, filtered (Whatman® 1 PS phase separator) and evaporated. The residue was chromatographed (eluant CHCl$_3$/MeOH/AcOH, 100:2:1 v/v/v) to provide a white solid which was freeze dried from dioxan/water to provide the title compound (34 mg, 37%)).

NMR (CDCl$_3$) δ8.62 (d, 1H, J=2 Hz); 7.1–8.2 (m, 13H); 5.70 (d, 1H, J=8 Hz); 4.58 (m, 2H); 3.0 (m, 1H); 1.4–2.0 (m, 8H)

M.S. (+ve FAB) (M+H)$^+$=526.2.

EXAMPLE 23

N-((3R)-1-Cyclopentylcarbonylmethyl-2,3-dihydro-2-oxo-5-phenyl-1H-1,4-benzodiazepin-3-yl)-N'-(3-carboxyphenyl)urea. Compound 33

The benzodiazepine of Example 4B was hydrogenated and resolved as described in Example 17. The resultant (S)-mandelate salt (430 mg, 0.838 mmol) was partitioned between CHCl$_3$ and 0.25M NaOH and the organic portion washed with brine filtered (Whatman® 1 PS phase separator) and evaporated to give the free amine as a colourless oil.

Methyl m-aminobenzoate (315 mg, 2.1 mmol) was taken up in CH$_2$Cl$_2$ (3 ml) and pyridine (170 µl, 2.1 mmol) and cooled to −60° C. under nitrogen. Triphosgene (207 mg, 0.7 mmol) was added and the mixture stirred over 15 min whilst the temperature rose to −20° C. Further pyridine (170 µl, 2.1 mmol) was added and stirring continued for 10 min at −20° C. and then the amine from above added in CH$_2$Cl$_2$ (1 ml) and stirring continued at room temperature for 2 hrs. The mixture was then diluted with EtOAc and washed with 1 M HCl and brine, filtered (Whatman® PS paper) and chromatographed (eluant EtOAc/Hexane, 40:60 v/v) to provide the intermediate ester as a colourless solid (375 mg, 83%).

The ester was taken up in dioxan/water (1:1, v/v, 5 ml) and treated with LiOH.H$_2$O (41 mg, 1.4 eq) at room temperature for 16 hrs. The mixture was evaporated and partitioned between EtOAc and 1M HCl. The organic portion was washed with brine, filtered (Whatman® 1 PS paper) and evaporated. The residue was chromatographed (eluant EtOAc/Hexane/AcOH, 60/40/2, v/v/v) to provide the title compound as a colourless solid (300 mg, 75%).

R$_f$ (EtOAc/Hexane/Acetic acid, 60:40:2 v/v/v) 0.24.

[α]$_D$=+68.4 (EtOAc, c=0.92).

$^1$H NMR and M.S. identical to Example 16.

EXAMPLES 24 AND 25

N-(3R)-1-((2RS)-2-Cyclopentyl-2-hydroxyethyl)-2,3-dihydro-2-oxo-5-phenyl-1H-1,4-benzodiazepin-3-yl)-N'-(3-carboxyphenyl)urea. Compound 35 and

N-((3R)-1-((2R)-2-Cyclopentyl-2-hydroxyethyl)-2,3-dihydro-2-oxo-5-phenyl-1H-1,4-benzodiazepin-3-yl)-N'-(3-carboxyphenyl)urea. Compound 36

The benzodiazepine of Example 23 (120 mg, 0.229 mmol) was taken up in ethanol at 0° C. and treated with sodium borohydride (16 mg, 0.4 mmol) for 15 min, then the mixture was allowed to stir at room temperature for a further 2 hrs, then evaporated and the residue chromatographed (eluant EtOAc/Hexane/Acetic acid, 60/40/2, v/v/v) to provide two products:

Ex. 24=a 1:1 mixture of faster and slower isomers (33 mg)

Ex. 25=the pure slower isomer (46 mg)

t.l.c. (EtOAc/Hexane/Acetic acid 60/40/2, v/v/v)
R$_f$ faster isomer=0.24
R$_f$ slower isomer=0.20
M.S. (M+H)$^+$=527 identical for both Examples.

EXAMPLE 26

N-((3R)-1-tert-Butylcarbonylmethyl-2,3-dihydro-2-oxo-5-phenyl-1H-1,4-benzodiazepin-3-yl)-N'-(3-methylphenyl)urea. Compound 38

The benzodiazepine of Example 2B was hydrogenated and the resultant amine resolved into its (R)-isomer (S)-mandelate salt as described in Example 17. A portion of the salt (150 mg, 0.299 mmol) was partitioned between CHCl$_3$ and 0.25 M NaOH. The organic portion was washed with brine, filtered (Whatman® 1 PS paper) and evaporated. The residue was taken up in CH$_2$Cl$_2$ and m-tolyl isocyanate (42 µl, 0.33 mmol) added. The mixture was stirred at room temperature for 1 hr, then evaporated and chromatographed (eluant EtOAc/hexane, 40/60, v/v) to provide a white solid which was freeze dried from acetonitrile/water (125 mg, 87%).

Data identical to Example 2C.

EXAMPLE 27

N-((3RS)-1-tert-Butylcarbonylmethyl-2,3-dihydro-2-oxo-5-(2-pyridyl)1-1H-1,4-benzodiazepin-3-yl)-N'-(3-methylphenyl)urea. Compound 39

27A (3RS)-3-Benzyloxycarbonylamino-1-tert-butylcarbonylmethyl-2,3-dihydro-2-oxo-5-(2-pyridyl)-1H-1,4-benzodiazepin-2-one (Scheme 1, Step (ii))

(3RS)-3-Benzyloxycarbonylamino-2,3-dihydro-5-(2-pyridyl)-1H-1,4-benzodiazepin-2-one (R. M. Freidinger et al. Eur. Pat. No. 0 434 364 A2) (2.02 g, 5 mmol) was alkylated with 1-bromopinacolone (1.08 g, 6 mmol) as described in Example 14A, to provide a white solid after chromatography (eluant EtOAc/hexane, 80:20 v/v) (2.16 g, 86%).

27B N-((3RS)-1-tert-Butylcarbonylmethyl-2,3-dihydro-2-oxo-5-(2-pyridyl)-1H-1,4-benzodiazepin-3-yl)-N'-(3-methylphenyl) urea (Scheme 1, Step (ii))

A portion of the benzodiazepine from Example 27A (502 mg, 1 mmol) was taken up in CH$_2$Cl$_2$ (2 ml) at −70° C. and treated dropwise with BBr$_3$ (6.5 ml, 1.0 M solution in $CH_2Cl_2$) and the mixture stirred for 3 hrs, during which time the cold bath expired. The mixture was quenched with water, then partitioned between EtOAc and 1M NaOH. The organic portion was washed with brine, filtered (Whatman® 1 PS paper) and evaporated. The residue was taken up in $CH_2Cl_2$ (3 ml) and treated with m-tolyl isoyanate (135 µl, 1.05 mmol) at room temperature for 1 hr. The mixture was evaporated and chromatographed (EtOAc/Hexane 75:25 v/v) and the resultant white solid recrystallised from acetonitrile (180 mg, 38%).

$R_f$ (EtOAc/Hexane, 60:40 v/v) 0.28.

$^1H$ NMR ($CDCl_3$) δ8.78 (d, 1H, J=2 Hz); 8.27 (d, 1H, J=7 Hz); 7.95 (m, 1H); 7.65–6.9 (m, 11H); 5.83(d, 1H, J=8 Hz); 5.10 (d, 1H, J=16 Hz); 4.70 (d, 1H, J 16 Hz); 2.42 (s, 3H); 1.40 (s, 9H).

M.S. (FAB) (M+H)$^+$ 484.4

EXAMPLE 28

N-((3RS)-1-tert-Butylcarbonylmethyl-2,3-dihydro-2-oxo-5-(phenyl-1H-1,4-benzodiazepin-3-yl)-N'-(3-carboxyphenyl)urea. Compound 40

The benzodiazepine of Example 2B was hydrogenated as described in Example 1C and the resultant amine (600 mg, 1.72 mmol taken up in dry THF (8 ml) and $Et_3N$ (260 µl, 1.9 mmol). A solution of p-nitrophenyl chloroformate (0.38 g, 1.9 mmol) in THF (3 ml) was added dropwise and the mixture stirred at room temperature for 1 hr, evaporated and chromatographed (eluant EtOAc/hexane, 40:60, v/v) to give a white solid (670 mg). This solid was taken up in DMF (10 ml) and treated with m-amino benzoic acid (245 mg, 1.75 mmol) at 45° C. for 18 hrs. The mixture was evaporated and chromatographed (eluant EtOAc/hexane/acetic acid, 60:40:2, v/v/v) and the product recrystallised from acetonitrile to provide the title compound (328 mg, 38%).

$^1H$ NMR ($CDCl_3$) δ7.8–7.0 (14H, m); 6.80 (1H, d, J=7 Hz); 5.6 (1H, d, J=8 Hz); 4.9 (1H, d, J=18 Hz); 4.8 (1H, d, J=18 Hz); 1.40 (9H, s).

M.S. (FAB) (M+H)$^+$=513.4

EXAMPLE 29

N-((3RS)-1-Cyclopentylcarbonylmethyl-2,3-dihydro-2-oxo-5-phenyl-1H-1,4-benzodiazepin-3-yl)-N'-(6-methyl-2-pyridyl)urea. Compound 27

This was prepared following the method of Example 1C using the benzodiazepine of Example 4B (165 mg, 0.33 mmol), 5% palladium-on-carbon (80 mg) and the isocyanate prepared below:

To a stirred solution of 2-amino-6-picoline (108 mg, 1 mmol) in $CH_2Cl_2$ (10 ml) at −20° C. was added triphosgene (110 mg, 0.37 mmol) and pyridine (79 mg, 1 mmol). The mixture was stirred for 30 min while warming to room temperature. Pyridine (79 mg, 1 mmol) was added and the reaction was heated to reflux for 30 min. The resulting solution of isocyanate was cooled to 0° C. and used directly.

The crude product was purified by flash chromatography on silica gel (Eluant EtOAc: 40–60 pet ether 80–20 v/v) to give the title compound as a white solid (45 mg, 28%, 96% pure by HPLC).

$R^f$ (EtOAc: 40–60 pet ether 20:80) 0.20.

NMR ($CDCl_3$) δ10.8 (1H, broads); 7.70–6.80 (13H, m); 5.70 (1H, d, J=8 Hz); 4.82 (1H, d, J=17 Hz); 4.75 (1H, d, J=17 Hz); 2.95 (1H, quintet, J=7 Hz); 2.60 (3H, s); 1.95–1.75 (4H, m); 1.70–1.45 (4H, m).

M.S. (FAB, +ve ion) m/e 496.0 (M+H).

EXAMPLE 30

N-((3RS)-1-Cyclopentylcarbonylmethyl-2,3-dihydro-2-oxo-5-phenyl-1H-1,4-benzodiazepin-3-yl)-N,-(3-pyridyl)urea. Compound 26

This was prepared following the method of Example 1C using the benzodiazepine of Example 4B (270 mg, 0.55 mmol), 5% palladium-on-carbon (100 mg) and the isocyanate prepared below:

To a stirred solution of nicotinic acid (172 mg, 1.4 mmol) and diisopropylethylamine (250 µl, 1.4 mmol) in THF (15 ml) at 0° C. was added isobutyl chloroformate (182 µl, 1.4 mmol). The mixture was stirred at 0° C. for 30 min, then a solution of sodium azide (97 mg, 1.5 mmol) in $H_2O$ (1 ml) was added and the mixture was stirred for 2 hours while warming to room temperature. The mixture was evaporated in vacuo and the residue taken up in cold EtOAc, washed with cold saturated $KHCO_3$ and cold brine, filtered (Whatman® 1 PS phase separator) and concentrated in vacuo. The residue was heated in THF (5 ml) at 60° C. for 5 min to give the isocyanate and used directly.

The crude product was purified by flash chromatography on silica gel (Eluant $CHCl_3$:MeOH:AcOH 100:2:1 v/v) to give the title compound as a crystalline solid (34 mg, 13% >99% pure by HPLC).

$R_f$ ($CHCl_3$:MeOH:AcOH, 100:2:1) 0.10.

NMR ($CDCl_3$) 8.70–7.20 (16H, m); 5.50 (1H, d, J=8 Hz); 4.75 (1H, d, J=18 Hz); 4.67 (1H, d, J=18 Hz); 3.70 (1H, m), 1.90–1.20 (8H, m).

MS (FAB, +ve ion) $^2/_m$ 482.0 (M+H)

EXAMPLE 31

N-((3RS)-1-Cyclopentylcarbonylmethyl-2,3-dihydro-2-oxo-5-phenyl-1H-1,4-benzodiazepin-3-yl)-N'-(3-carboxymethylphenyl)urea. Compound 24

31A Methyl 3-amino Phenyl Acetate

To a solution of 3-aminophenylacetic acid (3.02 g, 20 mmol) and methanol (60 ml) was added acetyl chloride (2 ml, 28 mmol). The reaction was heated to reflux for six hours. After allowing reaction to cool to room temperature the solvent was evaporated in vacuo. The resultant product was taken up in $CHCl_3$ and washed with saturated $KHCO_3$ and brine, filtered (Whatman® 1 PS phase separator), and concentrated in vacuo to afford the title acetate as a brown mobile oil (3.0 g, 91%).

NMR ($CDCl_3$) δ7.35–6.90 (4H, m); 4.75 (2H, s); 3.80 (3H, s); 3.65 (2H, s).

31B N-((3RS)-1-Cyclopentylcarbonylmethyl-2,3-dihydro-2-oxo-5-phenyl-1H-1,4-benzodiazepin-3-yl)-N'-(3-methoxycarbonylmethylphenyl)urea. (Scheme 1, Step (ii)

This was prepared following the method of Example 1C using the benzodiazepine of Example 4B (165 mg, 0.33 mmol), 5% palladium-on-carbon (80 mg) and the isocyanate prepared from the amine of Example 31A following the method of Example 29.

The crude product was purified by flash chromatography on silica gel (eluant EtOAc:hexane fr 60:40 v/v) to afford the methyl ester as a white solid (180 mg, 97%).

$R_f$ (EtOAc:hexane fr 60:40) 0.23.

31C N-((3RS)-1-cyclopentylcarbonylmethyl-2,3-dihydro-2-oxo-5-phenyl-1H-1,4-benzodiazepin-3-yl)-N'-(3-carboxymethylphenyl)urea To a solution of the benzodiazepine of Example 31B (180 mg, 0.32 mmol) in dioxan (10 ml) was added a solution of LiOH.H$_2$O (27 mg, 0.64 mmol) in H$_2$O (6 ml). The mixture was stirred for 18 hours, then dilute aq. HCl (10 ml) was added. The mixture was extracted with EtOAc twice, and the combined organic layers were washed with water and brine, filtered (Whatman® 1 PS phase separator) and concentrated in vacuo. The crude product was purified by flash chromatography on silica gel (eluant EtOAc:hexane fr:AcOH 70:30:2 v/v/v) to give the title compound as a white solid (105 mg, 61%, >98% pure by HPLC).

R$_f$ (EtOAc:hexane fr:AcOH, 70:30:2) 0.20

NMR (CDCl$_3$) δ8.00 (1H, s); 7.65–6.90 (15H, m); 5.65 (1H, d, J=8 Hz); 4.71 (2H, s); 3.50 (2H, s); 1.95–1.50 (9H, m).

M.S. (FAB, +ve ion) m/e 539.1 (M+H).

EXAMPLE 32

N-((3RS)-1-Cyclohexylmethylcarbonylmethyl-2,3-dihydro-2-oxo-5-phenyl-1H-1l4-benzodiazepin-3-yl)-N'-(3-methylphenyl)urea Compound 29

32A Bromomethyl Cyclohexylmethyl Ketone (Scheme 2, Steps (i)–(iii))

This was prepared following the method of Example 3A, The intermediate diazoketone was prepared from cyclohexylacetic acid (4.27 g, 30 mmol), thionyl chloride (8.7 mls, 120 mmol) and CH$_2$N$_2$ (generated from Diazald® 14.3, 66 mmol) and purified by flash chromatography on silica gel (eluant EtOAc:hexane fr 15:85 v/v). The diazoketone was subsequently treated with a saturated solution of HBr in EtOAc. Flash chromatography on silica gel (eluant EtOAc:hexane fr 5:95 v/v) afforded the title compound as a pale brown mobile oil (2.8 g, 43%).

NMR (CDCl$_3$)$_1$ δ3.99 (2H, s); 2.70 (2H, d, J=8 Hz); 2.00 (1H, m); 1.85–1.10 (10H, m).

32B (3RS)-3-Benzyloxycarbonylamino-1-cyclohexylmethylcarbonylmethyl-2,3-dihydro-5-phenyl-1H-1,4-benzodiazepin-2-one (Scheme 1, Step (i))

This was prepared following the method of Example 1B, using the Bock benzodiazepine (250 mg, 0.62 mmol), sodium hydride (26 mg of an 80% dispersion in oil, 0.87 mmol) and the bromomethylketone of Example 32A (219 mg, 1 mmol). The crude product was purified by flash chromatography on silica gel eluant (EtOAc:hexane fr 35:65 v/v) to afford the title compound as a colourless crystalline solid (315 mg, 97%).

R$_f$ (EtOAc:hexane fr, 40:60) 0:25.

NMR (CDCl$_3$) δ7.50–7.00 (14H, m); 6.60 (1H, d, J=8 Hz); 5.40 (1H, d, J=8 Hz); 5.10 (2H, s); 4.78 (1H, d, J=17 Hz); 4.67 (1H, d, J=17 Hz); 2.35 (2H, m); 1.85 (1H, m), 1.65–0.90 (10H, m).

32C N-((3RS)-1-Cyclohexylmethylcarbonylmethyl-2,3-dihydro-2-oxo-5-phenyl-1H-1,4-benzodiazepin-3-yl)-N'-(3-methylphenyl)urea. (Scheme 1 Step (ii))

This was prepared following the method of Example 1C using the benzodiazepine of Example 32B (315 mg, 0.60 mmol), 5% palladium-on-carbon (250 mg) and m-tolyl isocyanate (91 ml, 0.71 mmol). The crude product was purified by flash chromatography (eluant EtOAc:hexane fr 40:60 v/v) to give the title compound which was crystallised from acetonitrile to give a white solid (51 mg, 16%, >98% pure by HPLC).

R$_f$ (EtOAc:hexane fr, 40:60) 0.20.

NMR (CDCl$_3$) δ7.80–6.90 (15H, m); 5.70 (1H, d, J=8 Hz); 4.74 (1H, d, J=18 Hz); 4.67 (1H, d, J=18 Hz); 2.45–2.20 (5H, m); 1.95–0.90 (11H, m).

M.S. (FAB +ve ion) m/e 523.1 (M+H).

EXAMPLE 33

N-((3RS)-1-Cyclopentylmethylcarbonylmethyl-2,3-dihydro-2-oxo-5-phenyl-1H-1,4-benzodiazepin-3-yl)-N'-(3-methylphenyl)urea. Compound 30

33A Bromomethyl Cyclopentylmethyl Ketone (Scheme 2, Steps (i)–(iii))

This was prepared following the method of Example 3A. The intermediate diazoketone was prepared from cyclopentylacetic acid (3.85 g, 30 mmol), thionyl chloride (8.7 mls, 120 mmol) and CH$_2$N$_2$ (generated from Diazald®, 14.3 g, 66 mmol) and purified by flash chromatography on silica gel (eluant EtOAc: 40–60 pet ether 15:85 v/v). The diazoketone was subsequently treated with a saturated solution of HBr in EtOAc. Flash chromatogaphy on silica gel (eluant EtOAc: 40–60 pet ether 5:95 v/v) afforded the title ketone as a mobile oil (2.1 g, 34%).

NMR (CDCl$_3$) δ3.99 (2H, s); 2.80 (2H, d, J=8 Hz); 2.35 (1H, m); 1.95–1.30 (8H, m).

33B (3R5)-3-Benzyloxycarbonylamino-1-cyclopentylmethylcarbonylmethyl-2,3-dihydro-5-phenyl-1H-1,4-benzodiazepin-2-one-(Scheme 1, Step (i))

This was prepared following the method of Example 1B, using the Bock benzodiazepine (250 mg, 0.62 mmol), sodium hydride (26 mg of an 80%; dispersion in oil, 0.87 mmol) and the bromomethyl ketone of Example 33A (205 mg, 1 mmol). The crude product was purified by flash chromatogaphy on silica gel (eluant EtOAc:hexane fr 35:65 v/v) to afford the title compound as a colourless crystalline solid (300 mg, 95%).

R$_f$ (EtOAc:hexane Fr 40:60) 0.25.

NMR (CDCl$_3$) δ7.70–6.75 (15H, m); 5.50 (1H, d, J=8 Hz); 5.20 (2H, s); 4.74 (1H, d, J=18 Hz); 4.67 (1H, d, J=18 Hz); 2.50 (2H, m); 2.25 (1H, m); 1.85–1.15 (8H, m).

33C N-((3RS)-1-Cyclopentylmethylcarbonylmethyl-2,3-dihydro-2-oxo-5-phenyl-1H-1,4-benzodiazepin-3-yl)-N'-(3-methylphenyl) urea. (Scheme 1, step (ii))

This was prepared following the method of Example 1C using the benzodiazepine of Example 33B (300 mg, 0.59 mmol), 5% palladium-on-carbon (250 mg) and m-tolyl isocyanate (91 μl, 0.71 mmol). The crude product was purified by flash chromatography on silica gel (eluant- EtOAc:hexane fr 40:60 v/v) to give the title compound which was crystallised from acetonitrile to give a white solid (171 mg, 57%, >99% pure by HPLC).

R$_f$ (EtOAc:hexane fr 40:60) 0.20.

NMR (CDCl$_3$) δ7.85–6.98 (15H, m); 5.85 (1H, broad s); 4.80 (2H, S); 2.55 (2H,m); 2.45 (3H, s); 2.43–2.30 (1H, m); 1.90–1.20 (8H, m).

M.S. (FAB, +ve ion) m/e 509.1 (M+H).

EXAMPLE 34

N-((3RS)-1-(1-Methylcyclohexyl)carbonylmethyl)-2,3-dihydro-2-oxo-5-phenyl-1H-1,4-benzodiazepin-3-yl)-N'-(3-methylphenyl)urea. Compound 31

34A Bromomethyl (1-methylcyclohexyl) Ketone. (Scheme 2, Steps (i)–(iii))

This was prepared using the method of Example 3A. The intermediate diazoketone was prepared from 1-methyl-1-cyclohexanecarboxylic acid (4.27 g, 30 mmol), thionyl chloride (8.7 ml, 120 mmol) and CH$_2$N$_2$ (generated from Diazald® 14.3 g, 66 mmol). Without purification the diazoketone was subsequently treated with a saturated solution of HBr in EtOAc. Flash chromatography (eluant EtOAc:hexane fr 5:95 v/v) afforded the ketone as a mobile oil (1.90 g, 29%).

NMR (CDCl$_3$) δ4.25 (2H, s); 2.05 (2H, m); 1.70–1.40 (8H, m); 1.25 (3H, s).

34B (3RS)-3-Benzyloxycarbonylamino-1-((1-methylcyclohexyl)carbonylmethyl)-2,3-dihydro-5-phenyl-1,4-benzodiazepin-2-one (Scheme 1, Step (i))

This was prepared following the method of Example 1B, using the Bock benzodiazepine (250 mg, 0.62 mmol), sodium hydride (26 mg of an 80% dispersion in oil, 0.87 mmol) and the bromomethylketone of Example 34A (219 mg, 1 mmol). The crude product was purified by flash chromatography on silica gel (eluant EtOAc:hexane fr 35:65 v/v) to afford the title compound as a colourless crystalline solid (270 mg, 86%).

$R_f$ (EtOAc:hexane fr 40:60) 0.24.

NMR (CDCl$_3$) δ7.70–7.10 (14H, m); 6.80 (1H, d, J=8 Hz); 5.55 (1H, d, J=8 Hz); 5.30 (2H, s); 5.10 (1H, d, J=17 Hz); 4.75 (1H, d, J=17 Hz); 2.10 (2H, m); 1.70–1.40 (10H, m); 1.30 (3H, s).

34C N-((3RS)-1-((1-methylcyclohexyl)carbonylmethyl)-2,3-dihydro-2-oxo-5-phenyl-1H-1,4-benzodiazepin-3-yl)-N'-(3-methylphenyl)urea. (Scheme 1, Step (ii))

This was prepared using the method of Example 1C using the benzodiazepine of Example 34B (270 mg, 0.52 mmol), 5% palladium-on-carbon (150 mg) and m-tolyl isocyanate (84 μl, 0.66 mmol). The crude product was purified by flash chromatogaphy on silica gel (eluant EtOAc:hexane fr 40:60 v/v) to give the title compound which was crystallised from acetonitrile to give a crystalline solid (98 mg, 36% >99% pure, by HPLC).

$R_f$ (EtOAc:hexane fr 40:60) 0.20.

NMR (CDCl$_3$) δ7.70–6.90 (15H, m); 5.80 (1H, d, J=8 Hz); 4.90 (1H, d, J=17 Hz); 4.75 (1H, d, J=17 Hz); 2.30 (3H, s); 2.00 (2H, m); 1.60–1.35 (10H, m); 1.20 (3H, s).

M.S. (FAB +ve ion) m/e 523.3 (M+H).

EXAMPLE 35

N-((3RS)-1-Cyclopentylcarbonylmethyl-2,3-dihydro-2-oxo-5-phenyl-1H-1,4-benzodiazepin-3-yl)-N'-(3-carboxamidophenyl)urea. Compound 37

This was prepared following the method of Example 16B using the benzodiazepine of Example 16A (225 mg, 0.43 mmol) and 3-aminobenzamide (87 mg, 0.64 mmol). The crude product was purified by flash chromatography on silica gel (eluant EtOAc) to provide the title compound as a crystalline solid (30 mg, 13%, >99% by HPLC).

$R_f$ (EtOAc) 0.20

NMR (CDCl$_3$) δ8.95 (1H, s); 8.27 (1H, d, J=8 Hz); 8.21 (1H, d, J=8 Hz); 7.65–7.20 (15H, m); 5.55 (1H, d, J=8 Hz); 4.65 (2H, s); 2.90 (1H, quintet, J=8 Hz); 1.85–1.50 (8H, m).

M.S. (FAB +ve ion) m/e 524 (M+H).

EXAMPLE 36

N-((3RS)-1-tert-Amylcarbonylmethyl-2,3-dihydro-2-oxo-5-phenyl-1H-1,4-benzodiazepin-3-yl)-N'-(3-methylphenyl)urea. Compound 41

36A 1-Bromo-3,3-dimethypentan-2-one (Scheme 2, Steps (i)–(iii))

This was prepared following the method of Example 3A. The intermediate diazoketone was prepared from 2,2 dimethylbutyric acid (5.8 g, 50 mmol), thionyl chloride (14.6 ml, 200 mmol) and CH$_2$N$_2$ (generated from Diazald® 21.5 g, 100 mmol) and purified by flash chromatography on silica gel (eluant EtOAc:hexane fr 20:80 v/v). The diazoketone was subsequently treated with a saturated solution of HBr in EtOAc. Flash chromatography on silica gel (Eluant EtOAc:hexane fr 15:85 v/v) afforded the title ketone as a pale brown oil (1.50 g, 16%).

NMR (CDCl$_3$) δ4.25 (2H, s); 1.70 (1H, q, J=8 Hz); 1.30 (6H, s); 0.97 (3H, t, J=8 Hz).

36B N-((3RS)-1-tert-Amylcarbonylmethyl-3-benzyloxycarbonylamino-2,3-dihydro-5-phenyl-1H-1 4-benzodiazepin-2-one. (Scheme 1, Step (i))

This was prepared following the method of Example 1B, using the Bock benzodiazepine (500 mg, 1.25 mmol), sodium hydride (54 mg of an 80% dispersion in oil, 1.75 mmol) and the bromomethyl ketone of Example 36A (300 mg, 5 mmol). The crude product was purified by flash chromatography on silica gel (eluant EtOAc:hexane fr 35:65 v/v) to afford the title compound as a colourless crystalline solid (565 mg, 91%).

$R_f$ (EtOAc:hexane fr 40:60) 0.20

NMR (CDCl$_3$) δ7.90–7.30 (14H, m)); 6.90 (1H, d, J=8 Hz); 5.80 (1H, d, J=8 Hz); 5.40 (2H, s); 5.10 (1H, d, J=18 Hz); 4.75 (1H, d, J=18 Hz); 1.90 (2H, m); 1.40 (6H, s); 1.00 (3H, t, J=8 Hz).

36C N-((3RS)-1-tert-Amylcarbonylmethyl-2,3-dihydro-2-oxo-5-phenyl-1H-1,4-benzodiazepin-3-yl)-N'-(3-methylphenyl)urea. (Scheme 1, Step (ii))

This was prepared following the method of Example 1C using the benzodiazepine of Example 36B (240 mg, 0.46 mmol), 5% palladium-on-carbon (250 mg) and m-tolyl isocyanate (76 μl, 0.6 mmol). The crude product was purified by flash chromatography on silica gel (eluant EtOAc:hexane fr 40:60 v/v) to give the title compound which was crystallised from acetonitrile to give a white solid (98 mg, 43%, >99% by HPLC).

$R_f$ (EtOAc:hexane fr 40:60) 0.20.

NMR (CDCl$_3$) δ7.50–6.80 (15H, m); 5.65 (1H, d, J=8 Hz); 4.70 (1H, d, J=18 Hz); 4.65 (1H, d, J=18 Hz); 2.20 (3H, s); 1.50 (2H, q, J=8 Hz); 1.00 (6H, s); 0.70 (3H, t, J=8 Hz).

M.S. (FAB +ve ion) m/e 497.2 (M+H).

EXAMPLE 37

N-((3RS)-1-tert-Amylcarbonylmethyl-2,3-dihydro-2-oxo-5-phenyl-1H-1,4-benzodiazepin-3-yl)-N'-(3-carboxyphenyl)urea. Compound 42

37A (3RS)-3-p-Nitrobenzyloxycarbonylamino-1-tert-amylcarbonylmethyl-2,3-dihydro-2-oxo-5-phenyl-1H-1,4-benzodiazepin-2-one (Scheme, Step(i))

This was prepared following the method of Example 16A using the benzodiazepine of Example 36B (325 mg, 0.68 mmol), 5% palladium-on-carbon (250 mg) and p-nitrophenyl chloroformate (150 mg, 0.75 mmol). The crude product was purified by flash chromatography on silica gel (eluant EtOAc:hexane fr 35:65 v/v) to provide the product as a yellow solid (135 mg, 38%).

$R_f$ (EtOAc:hexane fr 40:60) 0.28.

NMR (CDCl$_3$) δ8.10 (2H, d, J=8 Hz); 7.50–7.00 (12H, m); 5.40 (1H, d, J=8 Hz); 4.85 (1H, d, J=17 Hz); 4.60 (1H, d, J=17 Hz); 1.55 (2H, q, J=8 Hz); 1.10 (6H, s); 0.75 (3H, t, J=8 Hz).

37B N-((3RS)-1-tert-Amylcarbonylmethyl-2,3-dihydro-2-oxo-5-phenyl-1H-1,4-benzodiazepin-3-yl)-N'-3-(carboxyphenyl)urea (Scheme 3, Step (ii))

This was prepared following the method of Example 16B using the benzodiazepine of Example 37A, (135 mg, 0.26 mmol) and m-aminobenzoic acid (54 mg, 0.39 mmol). The crude product was purified by flash chromatography on silica gel (eluant EtOAc:hexane fr:AcOH 60:40:2) to give the title compound which was crystallised from acetonitrile to give a colourless solid (30 mg, 22%, >97% pure by HPLC).

$R_f$ (EtOAc:hexane fr:AcOH 60:40:2) 0.20.

NMR (CDCl$_3$) δ8.10–6.80 (16H, m); 5.50 (1H, d, J=8 Hz); 4.80 (1H, d, J=18 Hz); 4.65 (1H, d, J=18 Hz); 1.40 (2H, q, J=8 Hz); 1.00 (6H, s); 0.70 (3H, t, J=8 Hz).

M.S. (FAB +ve ion) m/e 527.1 (M+H).

EXAMPLE 38

N-((3RS)-1-tert-Butylcarbonylmethyl-2,3-dihydro-2-oxo-5-(2-pyridyl)-1H-1,4-benzodiazepin-3-yl)-N'-(3-dimethylaminophenyl)urea. Compound 43

This was prepared following the method of Example 27B using the benzodiazepine of Example 27A (185 mg, 0.38 mmol), BBr₃ (2.5 ml, 1.0 M sol. in CH₂Cl₂), and the isocyanate prepared as below:

To a solution of 3-dimethylaminobenzoic acid (165 mg, 1 mmol) in toluene (5 ml) was added diphenylphosphoryl azide (275 mg, 1 mmol) and Et₃N (101 mg, 1 mmol). The mixture was stirred at room temperature for 2 hrs, then heated at reflux for 3 hrs. The solution of the above free amine in toluene (5 ml) was added to the cooled mixture and stirred at room temperature overnight, then evaporated, taken up in EtOAc, washed with 5% KHCO₃, H₂O and brine, filtered (Whatman® 1 PS phase separator) and evaporated, and chromatographed (eluant EtOAc) to provide a colourless solid (38 mg, 20%, 9% pure by HPLC).

R$_f$ (EtOAc) 0.15.

NMR (CDCl₃) δ8.78 (d, 1H, J=2 Hz); 8.27 (d, 1H, J=8 Hz); 7.95 (m, 1H); 7.65–6.6 (m, 11H); 5.83 (d, 1H, J=8 Hz); 5.05 (d, 1H, J=16 Hz); 4.60 (d, 1H, J=16 Hz); 3.00 (s, 6H); 1.40 (s, 9H).

M.S. (FAB) (M+H)⁺

EXAMPLE 39

N-((3RS)-1-tert-Butylcarbonylmethyl-2,3-dihydro-2-oxo-5-(2-pyridyl)-1H-1,4-benzodiazepin-3-yl)-N'-(3-carboxyphenyl)urea. Compound 44

39A Mono-Methyl Isophthalate

Dimethyl isophthalate (2.28 g, 11.7 mmol) was taken up in dioxan (25 ml) and treated with a solution of LiOH.H₂O (510 mg, 12.1 mmol) in water (15 ml) as described in Example 31B. The product was purified by chromatography (eluant EtOAc:hexane fr:AcOH 50:50:2 v/v/v) to provide the title compound (1.1 g, 48%).

NMR (CDCl₃) δ8.45 (s, 1H); 8.10 (2H, m); 7.45 (1H, m); 3.80 (3H, s).

39B N-((3RS)-1-tert-Butylcarbonylmethyl-2,3-dihydro-2-oxo-5-(2-pyridyl)-1H-1,4-benzodiazepin-3-yl)-N'-(3-methoxycarbonylphenyl)urea. (Scheme 1, Step (ii))

This was prepared following the method of Example 27B using the benzodiazepine of Example 27A (185 mg, 0.38 mmol), BBr₃ (2.5 ml, 1.0 M sol. in CH₂Cl₂) and the isocyanate prepared using the acid of Example 39A (250 mg, 1.4 mmol) with following the method of Example 38. The product was purified by chromatography (eluant EtOAc) to provide the title compound (110 mg, 56%).

NMR (CDCl₃) δ8.30 (1H, d, J=2 Hz); 7.95–7.00 (13H, m); 5.60 (1H, d, J=8 Hz); 4.80 (1H, d, J=16 Hz); 4.50 (1H, d, J=16 Hz); 3.70 (3H, s); 1.20 (9H, S).

39C ((3RS)-1-tert-Butylcarbonylmethyl-2,3-dihydro-2-oxo-5-(2-pyridyl)-1H-1,4-benzodiazepin-3-yl)-N'-(3-carboxphenyl)urea This was prepared following the method of Example 31B, using the benzodiazepine of Example 39B (110 mg, 0.21 mmol) and LiOH.H₂O (17 mg, 0.42 mmol). The crude product was purified by flash chromatography (eluant CHCl₃:MeOH:AcOH 75:2:1 v/v/v) to provide the title compound which was freeze-dried from MeCN/H₂O to give the product as a white solid (20 mg, 19%, >98% pure by HPLC).

R$_f$ (EtOAc:AcOH 100:2) 0.12.

NMR (CDCL₃) δ8.50 (1H, d, J=2 Hz); 8.10–7.35 (13H, m); 5.65 (1H, s); 5.15 (1H, d, J=18 Hz); 4.90 (1H, d, J=18 Hz); 1.35 (9H, s).

M.S. (FAB) (M+H)+

EXAMPLE 40

N-((3RS)-1-Cyclopentylcarbonylmethyl-2,3-dihydro-2-oxo-5-phenyl-1H-1,4-benzodiazepin-3-yl)-N'-(dimethylaminophenyl)urea. Compound 45

This was prepared following the method of Example 1C using the benzodiazepine of Example 4B (400 mg, (0.8 mmol), 5% palladium-on-carbon (400 mg) and the isocyanate (3 mmol) prepared as in Example 38. The crude product was purified by flash chromatography on silica gel (eluant EtOAc:hexane fr 60:40 v/v) to give the title compound which was crystallised from acetonitrile to afford a white solid (84 mg, 25% >99% pure by HPLC).

R$_f$ (EtOAc:hexane fr 60:40 v/v) 0.20.

NMR (CDCl₃) δ7.60–6.50 (15H, m); 5.65 (1H, d, J=8 Hz), 4.65 (s, 2H), 2.8 (s, 6H); 1.90–1.40 (9H, m).

M.S. (FAB, +ve ion) m/e 524.5 (M+H)

EXAMPLE 41

N-((3RS)-1-tert-Butylcarbonylmethyl-2,3-dihydro-2-oxo-5-phenyl-1H-1,4-benzodiazepin-3-yl)-N'-(3-dimethyl-aminophenyl)urea. Compound 46

This was prepared following the method of Example 1C using the benzodiazepine of Example 2B (380 mg, 0.8 mmol), 5% palladium-on-carbon (300 mg) and the isocyanate (3 mmol) prepared as in Example 38.

The crude product was purified by flash chromatography on silica gel (eluant EtOAc:hexane fr 55:45 v/v) and crystallised from acetonitrile to give the title compound as a white powder (127 mg, 31%, >99% pure by HPLC).

R$_f$ (EtOAc:hexane fr 60:40) 0.23.

NMR (CDCl₃) δ7.60–6.9 (15H, m); 5.60 (1H, d, J=8 Hz); 4.78 (1H, d, J=18 Hz); 4.68 (1H, d, J=18 Hz); 2.80 (6H, s); 1.20 (9H, s).

M.S. (FAB, +ve ion) m/e 512.5 (M+H).

EXAMPLE 42

N-((3RS)-1-Cyclopentylcarbonylmethyl-2,3-dihydro-2-oxo-5-phenyl-1H-14-benzodiazepin-3-yl)-N'-(3-methoxyphenyl)urea. Compound 47

This was prepared following the method of Example 1C using the benzodiazepine of Example 4B (400 mg, 0.8 mmol), 5% palladium-on-carbon (300 mg) and 3-methoxyphenyl isocyanate (136 μl, 1.04 mmol). The crude product was purified by flash chromatography on silica gel (eluant EtOAc:hexane fr 50:50 v/v) to give the title compound which was crystallised from acetonitrile to give a white powder (265 mg, 65%, >99% pure by HPLC).

R$_f$ (EtOAc:hexane fr 50:50) 0.20.

NMR (CDCl₃) δ7.66–6.80 (15H, m); 5.75 (1H, d, J=8 Hz); 4.85 (2H, d, J=8 Hz); 3.90 (3H, s); 3.00 (1H, m); 1.95–1.40 (8H, m).

M.S. (FAB, +ve ion) m/e

EXAMPLE 43

N-((3RS)-1-tert-Butylcarbonylmethyl-2,3-dihydro-2-oxo-5-phenyl-1H-1,4-benzodiazepin-3-yl)-N'-(3-methoxyphenyl)urea. Compound 48

This was prepared following the method of Example 1C using the benzodiazepine of Example 2B (385 mg, 0.8 mmol), 5% palladium-on-carbon (300 mg) and 3-methoxyphenyl isocyanate (136 μl, 1.04 mmol). The crude product was purified by flash chromatography on silica gel (eluant EtOAc:hexane fr 45:55 v/v) and crystallised from acetonitrile to provide the title compound as a white powder (249 mg, 63%, >99% pure by HPLC).

R$_f$ (EtOAc:hexane fr 50:50) 0.23.

NMR (CDCl₃) δ7.60–6.50 (15H, m); 5.85 (1H, d, J=8 Hz); 4.92 (1H, d, J=18 Hz); 4.82 (1H, d, J=18 Hz); 3.90 (3H, s); 1.30 (9H, s).

M.S. (FAB, +ve ion) m/e

EXAMPLE 44

N-((3RS)-1-Cyclopentylcarbonylmethyl-2,3-dihydro-2-oxo-5-phenyl-1H-1,4-benzodiazepin-3-yl)-N'-(3-nitrophenyl)urea. Compound 49

This was prepared following the method of Example 1C using the benzodiazepine of Example 4B (400 mg, 0.8 mmol), 5% palladium-on-carbon (300 mg) and 3-nitrophenyl isocyanate (171 mg, 1.04 mmol). The crude product was purified by flash chromatography on silica gel (eluant EtOAc:hexane fr 45:55 v/v) and crystallised from acetonitrile to give the title compound as a pale yellow solid (291 mg, 69%, >99% pure by HPLC).

$R_f$ (EtOAc:hexane fr 50:50) 0.22.

NMR (CDCl$_3$) δ8.00–7.10 (15H, m); 5.65 (1H, d, J=8 Hz); 4.74 (1H, d, J=17 Hz); 4.67 (1H, d, J=17 Hz); 2.95 (1H, m); 1.90–1.30 (8H, m).

M.S.

EXAMPLE 45

N-((3RS)-1-tert-Butylcarbonylmethyl-2,3-dihydro-2-oxo-5-phenyl-1H-1,4-benzodiazepin-3-yl)-N'-(3-nitrophenyl)urea. Compound 50

This was prepared following the method of Example 1C using the benzodiazepine of Example 2B (385 mg, 0.8 mmol), 5% palladium-on-carbon (300 mg) and 3-nitrophenyl isocyanate (171 mg, 1.04mmol). The crude product was purified by flash chromatography on silica gel (EtOAc:hexane Fr 45:55 v/v) and crystallised from acetonitrile to provide the title compound as a pale yellow solid (283 mg, 69% >99% pure by HPLC).

$R_f$ (EtOAc:hexane fr 50:50) 0.24.

NMR (CDCl$_3$) δ8.10–6.90 (15H, m); 5.65 (1H, d, J=8 Hz); 4.85 (2H, s); 1.25 (9H, S).

M.S.

EXAMPLE 46

N-((3RS)-1-((1-methylcyclopentyl)carbonylmethyl)-2,3-dihydro-2-oxo-5-phenyl-1H-1,4-benzodiazepin-3-yl)-N'-(3-methylphenyl)urea. Compound 32

46A 1-Methylcyclopentane Carboxylic Acid

Cyclohexene (25 ml, 0.246 mol) was treated with conc. sulphuric acid (100 ml) and formic acid (18.9 ml, 0.5 mol) at 5° C. for two hours. The mixture was poured onto ice and extracted twice with EtOAc. The organic extracts were washed with brine, then extracted with 2M KOH. The basic extract was acidified with 2M HCl and extracted with CHCl$_3$, filtered (Whatman® 1 PS phase separator) and evaporated. The resultant brown oil was purified by bulb-to-bulb distillation (125° C./oil pump) to give the title compound as a colourless oil (860 mg, 2%).

46B Bromomethyl 1-methylcyclopentyl ketone (Scheme 2, steps (i)–(iii))

This was prepared following the method of Example 3A. The intermediate diazoketone was prepared from the acid of Example 46A (860 mg, 6.7 mmol), thionyl chloride (2 ml, 30 mmol) and CH$_2$N$_2$ (generated from Diazald® 4.3 g, 20 mmol). The diazoketone was subsequently treated with a saturated solution of HBr in EtOAc. Flash chromatography on silica gel (eluant EtOAc:hexane fr 7:93 v/v) afforded the title compound (270 mg, 20;).

NMR (CDCl$_3$) δ4.20 (2H, s); 2.15–1.45 (8H, m); 1.35 (3H, s).

46C (3RS)-3-Benzyloxycarbonylamino-1-(1-methylcyclopentyl)carbonylmethyl-2,3-dihydro-5-phenyl-1H-1,4-benzodiazepin-2-one (Scheme 1, Step (i))

This was prepared following the method of Example 1B, using the Bock benzodiazepine (202 mg, 0.5 mmol), sodium hydride (21 mg, of an 80% dispersion in oil, 0.70 mmol) and the bromomethyl ketone of Example 46B (133 mg, 0.65 mmol). The crude product was purified by flash chromatogaphy on silica gel (eluant EtOAc:hexane fr 40:60 v/v) to afford the title compound as a colourless crystalline solid (190 mg, 74%).

$R_f$ (EtOAc:hexane fr 40:60) 0.24.

NMR (CDCl$_3$) δ7.55–7.05 (14H, m); 6.55 (1H, d, J=8 Hz); 5.35 (1H, d, J=8 Hz); 5.05(2H, s); 4.77 (1H, d, J=17 Hz); 4.66 (1H, d, J=17 Hz); 2.10–1.40 (8H, m); 1.20 (3H, s).

46D N-((3RS)-1-((1-Methylcyclopentyl)carbonylmethyl)-2,3-dihydro-2-oxo-5-phenyl-1H-1,4-benzodiazepin-3-yl)-N'-(3-methylphenyl)urea (Scheme 1, Step (ii))

This was prepared following the method of Example 1C using the benzodiazepine of Example 46C (190 mg, 0.37 mmol), 5% palladium-on-carbon (150 mg) and m-tolyl isocyanate (65 μl, 0.50 mmol). The crude product was purified by flash chromatography (eluant EtOAc:hexane fr 40:60 v/v) to give the title compound which was lyophilised from MeCN/H$_2$O to give the product as a white solid (102 mg, 54%, >97% pure by HPLC).

$R_f$ (EtOAc:hexane fr 40:60) 0.20.

NMR (CDCl$_3$) δ7.70–6.90 (15H, m); 5.70 (1H, d, J=8 Hz); 4.88 (1H, d, J=17 Hz); 4.82 (1H, d, J=17 Hz); 2.30 (3H, s); 2.10–1.40 (8H, m); 1.25 (3H, s).

M.S. (FAB +ve ion) m/e 509.3 [M+H]

EXAMPLE 47

N-((3RS)-1-tert-Butylcarbonylmethyl-2,3-dihydro-2-oxo-5-phenyl-1H-1,4-benzodiazepin-3-yl)-N'-(3N-formylaminophenyl)urea. Compound 51

47A 3-Formylaminobenzoic Acid

Acetic anhydride (50 ml) was added to 98% formic acid (85 ml). The mixture was stirred at room temperature for 30 mins, then 3-aminobenzoic acid (10 g, 73 mmol) was added and the mixture was stirred for one hour at room temperature. Water (850 ml) was added and the mixture was stirred overnight at room temperature. The resultant white precipitate was collected (10.66 g, 88%).

NMR (CDCl$_3$) δ8.90–7.50 (7H, m)

47B N-((3RS)-1-tert-Butylcarbonylmethyl-2,3-dihydro-2-oxo-5-phenyl-1H-1,4-benzodiazapin-3-yl)-N'-(3-formylaminophenyl)urea (Scheme I Step (ii))

The benzodiazepine of Example 2B was hydrogenated as described in Example 1C and the resultant amine (250 mg, 0.71 mmol) in toluene (2 ml) was treated with the isocyanate prepared using the acid of Example 47A (410 mg, 2.5 mmol) following the method of Example 38. The product was purified by chromatography twice (eluant EtOAc and CHCl$_3$:MeOH:AcOH 80:20:1 v/v/v) and crystallised from acetonitrile to give a colourless solid (75 mg, 21%, >97% pure by HPLC).

$^1$H NMR (CDCl$_3$) δ8.90–8.10 (3H, m); 7.75–7.10 (14½H, m); 6.70 (½H, d, J=18 Hz); 5.75 (1H, m); 4.90 (1H, m); 1.30 (9H, 3s).

M.S. [M+H]$^+$=512.2.

EXAMPLE 48

N-((3R)-1-((2R)-2-Hydroxy-3,3-dimethylbutyl)-2,3-dihydro-2-oxo-5-phenyl-1H-1,4-benzodiazepin-3-yl)-N'-(3-methylphenyl) urea. Compound 52

The benzodiazepine urea of Example 26 (180 mg, 0.373 mmol) was taken up in a mixture of methanol and dichloromethane (5 ml, 1/1, v/v) and CeCl$_3$.7H$_2$O (155 mg, 0.416 mmol) was added and the mixture stirred to dissolve all solids and then cooled to −78ζ C. Sodium borohydride (20 mg, 0.529 mmol) was added and the mixture stirred at −78° C. for 10 min then at −10° C. for 1 h, warming to room temp over 2 hours. The mixture was partitioned between CHCl$_3$ and brine and the organic portion dried and evaporated. The residue was purified by flash chromatography on silica gel (eluant EtOAc:hexane fr 40:60 v/v) to provide a colourless solid (105 mg, 58%, >98% pure by HPLC).

R$_f$ (EtOAc: 60–80 pet. ether 40:60) 0.31

$^1$H NMR (CDCl$_3$) δ7.8–6.9 (15H, m), 5.6 (1H, d, J=8 Hz); 4.35 (1H, m); 3.6 (2H, m); 2.2 (3H, s); 0.85 (9H, s).

M.S. (FAB, +ve ion) m/e=485.3 [M+H]

EXAMPLE 49

N-((3RS)-1-Cyclopentylcarbonylmethyl-2,3-dihydro-2-oxo-5-phenyl-1H-1,4-benzodiazepin-3-yl)-N'-(3-cyanophenyl)urea. Compound 22

This was prepared following the method of Example 1C using the benzodiazepine of Example 4B (300 mg, 0.6 mmol), 5% palladium-on-carbon (150 mg) and the isocyanate prepared from 3-cyanobenzoic acid (295 mg, 2 mmol) following the method of Example 30. The crude product was purified by flash chromatography on silica gel (eluant CHCl$_3$:AcOH 100:2 v/v) to give the title compound which was lyophilised from MeCN/H$_2$O to afford a white crystalline solid (30 mg, 10%, >97% pure by HPLC).

NMR (CDCl$_3$) δ8.20–8.05 (4H m); 7.70–7.10 (11H,m) ;5.50(1H,d,J=8 Hz);4.75 (1H, d, J=17 Hz); 4.66 (1H, d, J=17 Hz); 1.75–1.35 (9H, m).

M.S. (FAB): [M+H]$^+$=506.1

EXAMPLE 50

N-((3RS)-1-tert-Butylcarbonylmethyl-2,3-dihydro-2-oxo-5-phenyl-1H-1,4-benzodiazepin-3-yl)-N'-(3-cyanophenyl)urea. Compound 23

This was prepared following the method of Example 1C using the benzodiazepine of Example 2B (290 mg, 0.6 mmol), 5% palladium-on-carbon (150 mg) and the isocyanate prepared from 3-cyanobenzoic acid (295 mg, 2 mmol) following the method of Example 30. The crude product was purified by flash chromatography on silica gel (eluant CHCl$_3$:AcOH, 100:2 v/v) to afford the title compound which was lyophilised from MeCN/H$_2$O (36 mg, 12%, >96% pure by HPLC).

NMR (CDCl$_3$) δ8.20–8.05 (4H, m); 7.70–7.10 (11H, m); 5.50 (1H, d, J=.8 Hz); 4.90 (1H, d, J=17 Hz); 4.70 (1H, d, J=17 Hz); 1.15 (9H, s).

M.S. (FAB): [M+H]$^+$=494.2

EXAMPLE 51

N-((3RS)-1-(1-Adamantyl)carbonylmethyl-2,3-dihydro-2-oxo-5-phenyl-1H-1,4-benzodiazepin-3-yl)-N'-(3-methylphenyl)urea. Compound 25

51A 1-Adamantyl bromomethyl ketone (Scheme 2, Steps (ii)–(iii))

This was prepared following the method of Example 3A. The intermediate diazoketone was prepared from 1-adamantane carboxylic acid chloride (2.98 g, 15 mmol) and CH$_2$N$_2$ (generated from Diazald® 8.7 g, 40 mmol) and subsequently treated with a saturated solution of HBr in EtOAc. Flash chromatography on silica gel (eluant EtOAc:hexane fr 8:92) afforded the title compound as a pale brown mobile oil (2.30 g, 60%).

NMR (CDCl$_3$) δ4.20 (2H, s); 2.15–1.75 (15H, m).

51B (3RS)-1-(1-Adamantyl)carbonylmethyl-3-benzyloxycarbonylamino-2,3-dihydro-5-phenyl-1H-1,4-benzodiazepin-2-one (Scheme 1, Step (i))

This was prepared following the method of Example 1B, using the Bock benzodiazepine (202 mg, 0.5 mmol), sodium hydride (21 mg of an 80% dispersion in oil, 0.70 mmol) and the bromomethylketone of Example 51A (167 mg, 0.65 mmol). The crude product was purified by flash chromatography (eluant EtOAc:hexane fr 40:60 v/v) to afford the title compound as a colourless crystalline solid (130 mg, 46%).

NMR (CDCl$_3$) δ7.75–7.15 (14H,m); 6.80 (1H, d, J=8 Hz); 5.55 (1H, d, J=8 Hz); 5.25 (2H, s); 5.07 (1H, d, J=17 Hz); 4.76 (1H, d, J=17 Hz); 2.15–1.80 (15H, m)

51C N-((3RS)-1-(1-Adamantyl)carbonylmethyl-2,3-dihydro-2-oxo-5-phenyl-1H-1,4-benzodiazepin-3-yl)-N'-(3-methylphenyl)urea (Scheme 1, Step (ii))

This was prepared following the method of Example 1C using the benzodiazepine of Example 51B (130 mg, 0.23 mmol), 5% palladium-on-carbon (100 mg) and m-tolylisocyanate (45 μl, 0.35 mmol). The crude product was purified by flash chromatography (eluant EtOAc:hexane fr 35:65 v/v) to give the title compound which was lyophilised from MeCN/H$_2$O to give a white solid (57 mg. 44%, >96% pure by HPLC).

NMR (CDCl$_3$) δ7.75–7.10 (14H, m); 6.82 (1H,d,J=8 Hz); 5.75 (1H,d,J=8 Hz); 4.90 (1H,d,J=17 Hz); 4.80 (1H,d,J=17 Hz); 2.30 (3H, s); 2.10–1.60 (15H, m).

M.S. (FAB +ve ion) m/e 561.3 [M+H]

EXAMPLE 52

N-((3RS)-1-(3-Cyclohexyl-3-methyl-2-oxobutyl)-2,3-dihydro-2-oxo-5-phenyl-1H-1,4-benzodiazepin-3-yl)-N'-(3-methylphenyl)urea. Compound 28

52A Methyl-2-methyl-2-phenylpropanoate

To a solution of methyl phenylacetate (10.5 g, 70 mmol) in THF (125 ml) at 0° C. was added sodium hydride (2.25 g, 80% dispersion in oil, 75 mmol). The mixture was stirred for 30 mins at 0° C., then iodomethane (4.4 mls, 70 mmol) was added and the mixture was stirred for a further 30 mins at 0° C. Further sodium hydride (2.25 g, 80% dispersion in oil 75 mmol) was added and the mixture was stirred for 30 mins at 0° C., then iodomethane (8.8 mls, 140, mmol) was added and the mixture was left for 48 hours at room temp. The reaction was quenched with H$_2$O and the mixture was concentrated to remove the THF. The residue was taken up in EtOAc and washed with 5% KHCO$_3$, 0.3 M KHSO$_4$ and brine, filtered (Whatman® 1 PS phase separator) and evaporated to give the title compound as an oil (3.20 g, 26%).

NMR (CDCl$_3$) δ7.50–7.25 (5H, m); 3.60 (3H, s); 1.55 (6H, s).

52B 2-Methyl-2-phenylpropanoic Acid

A solution of the methyl ester of Example 52A (3.20 g, 18 mmol) in dioxan (25 ml) was treated with LiOH.H$_2$O (1.50 g, 36 mmol) in water (15 ml) as described in Example 31B, to give the title compound as a colourless oil (1.85 g, 63?%)

NMR (CDCl$_3$) δ7.50–7.25 (6H, m); 1.55 (6H, s).

52C 2-Cyclohexyl-2-methylpropanoic Acid

A solution of the acid of Example 52B (1.85 g, 11.3 mmol) in MeOH (100 mL) was degassed for 10 mins using nitrogen. 5% Rhodium-on-carbon (2 g) was added and the mixture was degassed for a further 10 mins, then hydrogenated at room temperature/60 p.s.i. (Parr) for 4 days. The mixture was filtered through celite and the filtrate was evaporated to give the title compound as a colourless oil (1.70 g, 88%)

NMR (CDCl₃) δ1-90–1.00 (11H, m); 1.20 (6H, s).

52D 1-Bromo-3-cyclohexyl-3-methylbutan-2-one [Scheme 2, Step (i)–(iii)]

This was prepared following the method of Example 3A. The intermediate diazoketone was prepared using the acid of Example 52C (170 g, 10 mmol), thionyl chloride (2 ml, 30 mmol), and $CH_2N_2$ (generated from Diazald® 8.7 g, 40 mmol) and subsequently treated with a saturated solution of HBr in EtOAc. Flash chromatography on silica gel (eluant EtOAc:hexane fr 5:95 v/v) gave title the compound as a pale brown mobile oil (280 mg, 11%).

NMR (CDCl₃) δ4.30 (2H, s); 2.90–1.10 (11H, m); 1.20 (6H, s).

52E (3RS)-3-Benzyloxycarbonylamino-1-(3-cyclohexyl-3-methyl-2-oxobutyl)-2,3-dihydro-5-phenyl-1H-1,4-benzodiazepin-2-one (Scheme 1, Step (i))

This was prepared following the method of Example 1B using the Bock benzodiazepine (202 mg, 0.5 mmol), sodium hydride (21 mg of an 80 dispersion in oil, 0.70 mmol) and the bromomethylketone of Example 52D (160 mg, 0.65 mmol). The crude product was purified by flash chromatography (eluant EtOAc:hexane A 35:65 v/v) to afford the title compound as a colourless crystalline solid (70 mg, 25%)

NMR (CDCl₃) δ7.55–7.05 (14H,m); 655 (1H, d, J=8 Hz); 5.30 (1H, d, J=8 Hz); 5.02(2H, s); 4.78 (1H, d, J=17 Hz); 4.58 (1H, d, J=17 Hz); 1.70–0.90 (11H, m); 1.00 (6H, s).

52F N-((3RS)-1-(3-Cyclohexyl-3-methyl-2-oxobutyl)-2,3-dihydro-2-oxo-5-phenyl-1H-1,4-benzodiazepin-3-yl)-N'-(3-methylphenyl)urea (Scheme 1, Step (ii))

This was prepared following the method of Example 1C using the benzodiazepine of Example 52E (70 mg, 0.13 mmol), 5% palladium-on-carbon (50 mg) and m-tolylisocyanate (20 μl, 0.16 mmol). The crude product was purified by flash chromatography (eluant EtOAc:hexane fr 40:60 v/v) to give the title compound which was lyophilised from $MeCN/H_2O$ to give the product as a white solid (35 mg, 50%, >95% pure by HPLC).

NMR (CDCl₃) δ7.70–6.95 (14H, m); 6.60 (1H, m); 5.75 (1H, d, J=8 Hz); 4.90 (1H, d, J=17 Hz); 4.83 (1H, d, J=17 Hz); 2.35 (3H, s); 1.90–0.95 (11H, m); 1.10 (6H, s).

M.S. [M+H]⁺=551.3.

EXAMPLE 53

N-((3RS)-1-(1-Methylcyclopropyl)carbonylmethyl-2,3-dihydro-2-oxo-5-phenyl-1H-1,4-benzodiazepin-3-yl)-N'-(3-methylphenyl)urea. Compound 54

53A Bromomethyl 1-methylcyclopropyl ketone

To a stirred solution of methyl 1-methylcyclopropyl ketone (5 g, 50.9 mmol) in MeOH (30 ml) at 0° C. was added bromine (2.6 ml, 51 mmol) dropwise. The mixture was stirred at 0° C. for 2 hours. Water (15 ml) was added and the mixture was stirred at room temp overnight. Further water (45 ml) was added and the product was extracted into $Et_2O$. The organic extract was washed with 10% $K_2CO_3$, $H_2O$ and brine, dried over $CaCl_2$ for 30 mins, filtered (Whatman® 1 PS phase separator) and concentrated in vacuo to afford the title compound as a clear mobile oil (8.2 g, 91%).

NMR (CDCl₃) δ3.95 (2H, s); 1.40 (3H, s); 1.30 (2H, t, J=7 Hz); 0.80 (2H, t, J=7 Hz).

53B (3RS)-3-Benzyloxycarbonylamino-1-(1-methylcyclopropyl)carbonylmethyl-2,3-dihydro-1H-1,4-benzodiazepin-2-one (Scheme 1, Step (i))

This was prepared following the method of Example 1B, using the Bock benzodiazepine (202 mg, 0.5 mmol), sodium hydride (21 mg of an 80% dispersion in oil, 0.70 mmol) and the bromomethyl ketone of Example 53A (133 mg, 0.75 mmol). The crude product was purified by flash chromatography on silica gel (eluant EtOAc:hexane fr 40:60 v/v) to afford the title compound as a colourless crystalline solid (190 mg, 79%).

NMR (CDCl₃) δ7.55–7.10 (14H, m); 6.65 (1H, d, J=8 Hz); 5.40 (1H, d, J=8 Hz); 5.10(2H, s); 4.77 (1H, d, J=17 Hz); 4.55 (1H, d, J=17 Hz); 1.40 (3H, s,); 1.25(2H, t, J=7 Hz); 0.75 (2H, t, J=7 Hz).

53C N-((3RS)-1-(1-Methylcyclopropyl)carbonylmethyl-2,3-dihydro-2-oxo-5-phenyl-1H-1,4-benzodiazepin-3-yl)-N'-3-methylphenyl)urea (Scheme 1, Step (ii))

This was prepared following the method of Example 1C using the benzodiazepine of Example 53B (190 mg, 0.4 mmol), 5 palladium-on-carbon (200 mg) and m-tolylisocyanate (65 μl, 0.5 mmol). The crude product was purified by flash chromatography on silica gel (eluant EtOAc:hexane fr 45:55 v/v) to give the title compound which was lyophilised from $MeCN/H_2O$ to give a white solid (150 mg, 78%, >98% pure by HPLC).

$R_f$ (EtOAc:hexane fr 40:60) 0.16.

NMR (CDCl₃) δ7.70–7.10 (14H,m); 6.85 (1H, d, J=8 Hz); 5.75 (1H, d, J=8 Hz); 4.82(1H, d, J=17 Hz); 4.75 (1H, d, J=17 Hz); 2.35 (3H, s); 1.45 (3H, s); 1.30(2H, t, J=7 Hz); 0.90 (2H, t, J=7 Hz).

M.S. (FAB, +ve ion) m/e 481.2 [M+H].

EXAMPLE 54

N-((3RS)-1-tert-Butylcarbonylmethyl-2,3-dihydro-2-oxo-5-(2-chlorophenyl)-1H-1,4-benzodiazepin-3-yl)-N'-(3-methylphenyl)urea. Compound 55

54A (3RS)-3-Benzyloxycarbonylamino-1-tert-butylcarbonylmethyl-7-chloro-5-(2-chlorophenyl)-1-IH-1,4benzodiazepin-2-one (Scheme 1, Step (1))

This was prepared following the method of Example 1B, using (3RS)-3-benzyloxy-carbonylamino-7-chloro-5-(2-chlorophenyl)-1H-1,4-benzodiazepin-2-one (241 mg, 0.51 mmol, prepared in analogy to the Bock benzodiazepine), sodium hydride, (22 mg of an 80% dispersion in oil, 0.72 mmol), and 1-bromopinacolone (179 mg, 1 mmol). The crude product was purified by flash chromatography on silica gel (eluant EtOAc:hexane fr 30:70 v/v) to afford the title compound (145 mg, 52%).

NMR (CDCl₃) δ7.80–7.30 (12H, m); 6.80 (1H, d, J=8 Hz); 5.60 (1H, d, J=8 Hz); 5.30(2H, s); 5.25 (1H, d, J=17 Hz); 4.60 (1H, d, J=17 Hz); 1.35 (9H, s).

54B N-((3RS)-1-tert-Butylcarbonylmethyl-2,3-dihydro-2-oxo-5-(2-chlorophenyl)-1H-1,4-benzodiazepin-3-yl-N'-(3-methylphenyl)urea (Scheme 1, Step (ii))

This was prepared following the method of Example 1C using the benzodiazepine of Example 54A (145 mg, 0.26 mmol), 5% palladium-on-carbon (120 mg) and m-tolyl isocyanate (40 μl, 0.32 mmol). The crude product was purified by chromatography (eluant EtOAc:hexane fr 40:60 v/v) to provide the title compound which was lyophilised from $MeCN/H_2O$ to give the product as a white solid (45 mg, 31%).

NMR (CDCl₃) δ7.70–6.95 (14H, m); 5.80 (1H, d, J=8 Hz); 5.30 (1H, d, J=17 Hz); 4.60 (1H, d, J=17 Hz); 2.40 (3H, s), 1.30 (9H, s).

M.S. (FAB, +ve ion) m/e 517.2 [M+H]

Note: The 7-chloro substituent is lost during the hydrogenolysis.

EXAMPLE 55

N-((3RS)-1-IsorroDylcarbonylmethyl-2,3-dihydro-2-oxo-5-phenyl-1H-1,4-benzodiazepin-3-yl-N'-(3-methylphenyl1)urea. Compound 56

55A 1-Bromo-3-methylbutan-2-one (Scheme 2, Steps (i)–(iii))

This was prepared following the method of Example 3A. The intermediate diazoketone was prepared from isobutyric acid 8.82 g (100 mmol), thionyl chloride (30 ml, 400 mmol) and $CH_2N_2$ (generated from Diazald®, 43 g, 200 mmol) and subsequently treated with a saturated solution of HBr in EtOAc. Flash chromatography on silica gel (eluant EtOAc:hexane fr 6:94 v/v) afforded the title compound as a mobile oil (300 mg, 1.8%).

NMR ($CDCl_3$) δ4.25 (2H, s; 3.00 (1H, heptet, J=8 Hz); 1.25 (6H, d, J=8 Hz).

55B (3RS)-3-Benzyloxycarbonylamino-1-isopropylcarbonylmethyl-2,3-dihydro-5-phenyl-1H-1,4-benzodiazepin-2-one (Scheme 1, Step (i))

This was prepared following the method of Example 1B, using the Bock benzodiazepine (606 mg, 1.5 mmol), sodium hydride (63 mg of an 80% dispersion in oil, 2.1 mmol) and the bromomethylketone of Example 55A (300 mg, 1.8 mmol)

The crude product was purified by flash chromatography on silica gel (eluant EtOAc:hexane fr 40:60 v/v) to afford the title compound as a colourless crystalline solid (250 mg, 36%).

NMR ($CDCl_3$) δ7.70–7.20 (14H, m); 6.75 (1H, d, J=8 Hz); 5.50 (1H, d, J=8 Hz); 5.20 (2H, s); 4.85 (1H, d, J=17 Hz); 4.75 (1H, d, J=17 Hz); 2.80 (1H, heptet, J=8 Hz); 1.25 (6H, d, J=8 Hz).

55C N-((3RS)-1-Isopropylcarbonylmethyl-2,3-dihydro-2-oxo-5-phenyl-1H-1,4-benzodiazepin-3-yl)-N'(3-methylphenyl)urea (Scheme 1, Step (ii))

This was prepared following the method of Example 27B using the benzodiazepine of Example 55B (250 mg, 0.53 mmol), $BBr_3$ (3.2 ml, 1.0 M sol in $CH_2Cl_2$) and m-tolyl isocyanate (40 μl, 0.31 mmol). The product was purified by flash chromatography on silica gel (eluant EtOAc:hexane fr 55:45 v/v) to provide the title compound which was lyophilised from $MeCN/H_2O$ to give the product as a white solid (51 mg, 21%, >98% pure by HPLC).

$R_f$ (EtOAc:hexane fr 50:50) 0.16.

NMR ($CDCl_3$) δ7.70–7.15 (14H, m); 6.85 (1H, d, J=8 Hz); 5.70 (1H, d, J=8 Hz); 4.75 (2H, s); 2.70 (1H, heptet, J=8 Hz); 2.30 (3H, s); 1.18 (6H, d, J=8 Hz).

M.S. (FAB, +ve ion) m/e 469.3 [M+H]

EXAMPLE 56

N-((3R)-1-tert-Butylcarbonylmethyl-2,3-dihydro-2-oxo-5-phenyl1H-1,4-benzodiazepin-3-yl)-N'-(3-methylaminophenyl)urea. Compound 57.

56A N-Methyl-3-methoxycarbonylformanilide

This was prepared following the method of Example 1B, using 3-carboxyformanilide (2.28 g, 13.8mmol), sodium hydride (1.05 g of an 80% dispersion in oil, 34.5 mmol) and iodomethane (2.85 mls, 45 mmol). The crude product was purified by flash chromatography on silica gel (eluant EtOAc:hexane fr 60:40 v/v) to afford the title compound as a colourless crystalline solid (2.30 g, 86%).

NMR ($CDCl_3$) δ8.50 (1H, s; 7.90–7.40 (4H, m); 3.95 (3H, s); 3.40 (3H, s).

56B N-Methyl-3-carboxyformanilide

This was prepared following the method of Example 31B, using the ester of Example 56A (1.90 g, 9.8 mmol) and $LiOH.H_2O$ (840 mg, 20 mmol). The title compound was obtained as a colourless crystalline solid after work up (985 mg, 56!k).

56C N-((3R)-1-tert-Butylcarbonylmethyl-2,3-dihydro-2-oxo-5-phenyl-1H-1,4-benzodiazepin-3-yl)-N'-(3-(N-formyl-N-methylamino)phenyl)urea (Scheme 1, Step (ii))

The resolved aminobenzodiazepine of Example 26 (980 mg, 2.8 mmol) in toluene (10 ml) was treated with the isocyanate prepared from the acid of Example 56B (985 mg, 5.5 mmol) following the method of Example 38. The product was purified by flash chromatography on silica gel (eluant EtOAc:hexane fr 75;25 v/v) to provide the title compound (960 mg, 65%).

NMR ($CDCl_3$) δ8.45 (1H, s); 7.65–7.05 (14H, m); 6.70 (1H, d, J=8 Hz); 5.70 (1H, d, J=8 Hz) 4.98 (1H, d, J=17 Hz); 4.75 (1H, d, J=17 Hz); 3.20 (3H, s); 1.30 (9H, s).

56D N-((3R)-1-tert-Butylcarbonylmethyl-2,3-dihydro-2-oxo-5-phenyl-1H-1,4-benzodiazepin-3-yl)-N'-(3-methylaminophenyl)urea The benzodiazepine of Example 56C (960 mg, 1.8 mmol) was taken up in acetone (15 ml) and treated with 4N HCl (9 ml). The mixture was stirred at room temp for 3 days, then evaporated, taken up in $CH_2Cl_2$, washed with 5% $KHCO_3$, filtered (Whatman® 1 PS phase separator) and evaporated. The residue was purified by flash chromatography on silica gel (eluant $CHCl_3$:MeOH:AcOH 120:2:1 v/v/v) to give the title compound which was crystallised from $MeCN/Et_2O$ to give a white solid (400 mg, 45%, >99% pure by HPLC).

NMR (CDCl3) δ7.70–7.20 (13H, m); 6.75 (1H, s); 6.65 (1H, d, J=8 Hz); 6.30 (1H, d, J=8 Hz); 5.75 (1H, d, J=8 Hz); 4.85 (2H, 5); 2.80 (3H, s); 1.20 (9H, s).

M.S. (FAB +ve ion) m/e 498.3 [M+H]

EXAMPLE 57

N-((3RS)-1-tert-Butylcarbonylmethyl-2,3-dihydro-2-oxo-5-(2-pyridyl)-1H-1,4-benzodiazepin-3-yl)-N'-(3-methylaminophenyl)urea. Compound 58

57A N-((3RS)-1-tert-Butylcarbonylmethyl-2,3-dihydro-2-oxo-5-(2-pyridyl)-1H-1,4-benzodiazepin-3-yl)-N'-(3-(N-formyl-N-methylamino)phenyl)urea (Scheme 1, Step (ii))

This was prepared following the method of Example 27B using the benzodiazepine of Example 27A (340 mg, 0.7 mmol), $BBr_3$ (4.4 ml, 1.0 M sol in $CH_2Cl_2$) and the isocyanate prepared using the acid of Example 56B (420 mg, 2.3 mmol) following the method of Example 38. The product was purified by flash chromatography on silica gel (eluant EtOAc) to provide the title compound (185 mg, 50%).

NMR ($CDCl_3$) δ8.25 (1H, d, J=8 Hz); 8.00 (1H, s); 7.60–6.80 (12H, m); 6.40 (1H, d, J=8 Hz); 5.35 (1H, d, J=8 Hz); 4.62 (1H, d, J=17 Hz); 4.30 (1H, d, J=17 Hz); 2.90 (3H, s); 0.90 (9H, s).

57B N-((3RS)-1-tert-Butylcarbonylmethyl-2,3-dihydro-2-oxo-5-(2-pyridyl)-1H-1,4-benzodiazepin-N'-3-yl)-3-methylaminophenyl)urea This was prepared following the method of Example 56D, using the benzodiazepine of Example 57A (185 mg, 0.35 mmol), acetone (5 ml) and 4N HCl (3 ml). The crude product was purified by flash chromatogaphy on silica gel (eluant $CHCl_3$:MeOH:AcOH 120:2:1 v/v/v) to provide the title compound which was lyophilised from $MeCN/H_2O$ to give the product as a white solid (67 mg, 38%, >95% pure by HPLC).

NMR ($CDCl_3$) δ8.30 (1H, d, J=8 Hz); 7.95 (1H, d, J=8 Hz); 7.60 (1H, t, J=7 Hz); 7.35 (1H, t, J=7 Hz); 7.20–6.85 (8H, m); 6.50 (1H, d, J=8 Hz); 6.30 (1H, d, J.=8 Hz); 6.10 (1H, d, J=8 Hz); 5.40 (1H, d, J=8 Hz); 4.75 (1H, d, J=17 Hz); 4.40 (1H, d, J=17 Hz); 2.60 (3H, s); 0.95 (9H, s).

M.S. (FAB +ve ion) m/e 499.3 [M+H]

EXAMPLE 58

N-((3R)-1-tert-Butylcarbonylmethyl-2,3-dihydro-2-oxo-5-phenyl-1H-1,4-benzodiazepin-3-yl)-N'-(3-(N-ethyl-N-methylamino) phenyl)urea. Compound 59

58A Methyl-3-(N-ethyl-N-methylamino)benzoate

This was prepared following the method of Example 56D using the methyl ester of Example 56A (2.35 g, 12.2 mmol), acetone (100 ml) and 4N HCl (60 ml). The resultant amine was taken up in MeOH:AcOH (99:1, 70 ml) at 0° C. Acetaldehyde (1.0 ml, 18 mmol) and NaBH$_3$CN (1.13 g, 18 mmol) were added. The mixture was stirred at 0° C. for 2 hours, then evaporated, taken up in EtOAc, washed with 5% KHCO$_3$, brine, filtered (Whatman® 1 PS phase separator) and evaporated. The residue was purified by flash chromatography on silica gel (eluant EtOAc:hexane fr 15:85 v/v) to give the title compound (2.15 g, 91%).

NMR (CDCl$_3$) δ7.40–7.25 (3H, m); 6.90 (1H, m); 3.90 (3H, s); 3.45 (2H, quartet, J=7 Hz); 2.95 (3H, s); 1.15 (3H, t, J=7 Hz).

58B 3-(N-Ethyl-N-methylamino)benzoic Acid

This was prepared following the method of Example 31B, using the ester of Example 58A (2.15 g, 11.1 mmol) and LiOH.H$_2$O (920 mg, 22 mmol). The crude product was purified by flash chromatography on silica gel (eluant EtOAc:hexane fr:AcOH 35:65:2) to give the title compound (1.90 g, 95%).

58C N-((3R)-1-tert-Butylcarbonylmethyl-2,3-dihydro-2-oxo-5-phenyl-1H-1,4-benzodiazepin-3-yl)-N'-(3-(N-ethyl-N-methylaminophenyl)urea (Scheme 1, Step) (ii))

The resolved aminobenzodiazepine of Example 26 (245 mg, 0.7 mmol) in toluene (5 ml) was treated with the isocyanate prepared using the acid of Example 58B (250 mg, 1.4 mmol) following the method of Example 38. The product was purified by flash chromatography on silica gel (eluant EtOAc:hexane fr 45:55 v/v) to give the title compound which was crystallised from acetonitrile to give the product as a white solid (237 mg, 64%, >99% by HPLC).

NMR (CDCl$_3$) δ7.70–7.05 (13H, m); 6.58 (1H, d, J=8 Hz); 6.50 (1H, d, J=8 Hz); 5.80 (1H, d, J=8 Hz); 4.90 (1H, d, J=17 Hz); 4.83 (1H, d, J=17 Hz); 3.40 (2H, quartet, J=7 Hz); 2.95 (3H, s); 1.25 (9H, s); 1.15 (3H, t, J=7 Hz).

M.S. (FAB, +ve ion) m/e 526.3 [M+H]

EXAMPLE 59

N-((3R)-1-tert-Butylcarbonylmethyl-2,3-dihydro-2-oxo-5-phenyl-1H-1,4-benzodiazepin-3-yl)-N'-(3-diethylaminophenyl)urea. Compound 60

59A 3-Ethoxycarbonyl-N-ethylformanilide

This was prepared following the method of Example 1B, using 3-carboxyformanilide (5.0 g, 30 mmol), sodium hydride (2.26 g, of an 80% dispersion in oil, 75 mmol) and iodoethane (5.2 ml, 64 mmol). The product was purified by flash chromatography on silica gel (eluant EtOAc:hexane fr 50:50 v/v) to provide the title compound (6.00 g, 27.1 mmol).

NMR (CDCl$_3$) δ8.50 (1H, s); 8.00–7.50 (4H, m); 4.50 (2H, q, J=7 Hz); 4.00 (2H, q, J=7 Hz); 1.50 (3H, t, J=7 Hz); 1.30 (3H, t, J=7 Hz).

59B Ethyl 3-diethylaminobenzoate

This was prepared using the method of Example 56D using the ethyl ester of Example 59A (3.50 g, 15.8 mmol), acetone (130 ml) and 4 N HCl (80 ml). The resultant amine was alkylated following the method of Example 58A using acetaldehyde (1.3 ml, 23.3 mmol) and NaBH$_3$CN (1.46 g, 23.3 mmol). The crude product was purified by flash chromatography on silica gel (eluant EtOAc:hexane fr 10:90 v/v) to give the title compound (1.90 g, 54%).

NMR (CDCl$_3$) δ7.95–7.80 (3H, m); 7.40 (1H, m); 4.90 (2H, q, J=7 Hz); 3.90 (4H, q, J=7 Hz); 1.95 (3H, t, J=7 Hz); 1.75 (6H, t, J=7 Hz).

59C 3-Diethylaminobenzoic Acid

This was prepared following the method of Example 31B, using ester of Example 59B (1.90 g, 8.6 mmol) and LiOH.H$_2$O (720 mg, 17.2 mmol). The crude product was purified by flash chromatography on silica gel (eluant EtOAc:hexane fr:AcOH 30:70:2 v/v/v) to give the title compound (1.0 g, 60%).

59D N-((3R)-1-tert-Butylcarbonylmethyl-2,3-dihydro-2-oxo-5-phenyl-1H-1,4-benzodiazepin-3-yl)-N'-(3-diethylaminophenyl)urea (Scheme 1, Step (ii))

The resolved aminobenzodiazepine of Example 26 (175 mg, 0.5 mmol) in toluene (5 ml) was treated with the isocyanate prepared using the acid of Example 59C (240 mg, 1.2 mmol) following the method of Example 38. The product was purified by flash chromatography on silica gel (eluant EtOAc:hexane fr 45:55 v/v) to give the title compound which was crystallised from MeCN to give the product as a white solid (147 mg, 55%, >99% pure by HPLC).

NMR (CDCl$_3$) δ7.70–7.05 (13H, m); 6.60 (1H, d, J=8 Hz); 6.50 (1H, d, J=8 Hz); 5.80 (1H, d, J=8 Hz); 4.90 (1H, d, J=17 Hz); 4.76 (1H, d, J=17 Hz); 3.45 (4H, q, J=7 Hz); 1.30 (9H, s); 1.20 (6H, t, J=7 Hz).

M.S. (FAB, +ve ion) m/e 540.3 [M+H]

EXAMPLE 60

N-((3RS)-1-tert-Butylcarbonylmethyl-2,3-dihydro-2-oxo-5-phenyl-1H-1,4-benzodiazepin-3-yl-N'-(3-dimethylaminomethylphenyl)urea. Compound 61

60A 3-Dimethylaminomethyl Benzonitrile

To a solution of 3-cyanobenzaldehyde (2.50 g, 19 mmol) in MeOH:AcOH (25 ml, 99:1) was added dimethyl amine (2.5 ml, 50 mmol) at 0° C., followed by NaBH$_3$CN (1.80 g, 29 mmol). The mixture was stirred at 0° C. for 18 hours, then evaporated, taken up in EtOAc, washed with 5 KHCO$_3$, brine filtered (Whatman® 1 PS phase separator) and evaporated. The residue was purified by flash chromatography on silica gel (eluant EtOAc:MeOH 98:2 v/v) to give the title compound (1.15 g, 38%).

NMR (CDCl$_3$) δ7.75–7.60 (4H, m); 3.50 (2H, s); 2.35 (6H, s).

60B Methyl 3-dimethylaminomethylbenzoate

A solution of the nitrile of Example 60A, (1.15 g, 7.2 mmol) in 4M HCl/MeOH (200 ml) was added at 0° C. for 2 hours and at room temperature for 18 hours. H$_2$O (25 ml) was added and the mixture was stirred for one hour at room temp, then evaporated and azeotroped with toluene, taken up in CHCl$_3$, washed with 5% KHCO$_3$, filtered (Whatman® 1 PS phase separator) and evaporated to give the title compound (1.20 g, 86%).

NMR (CDCl$_3$) δ8.00–7.50 (4H, m); 4.00 (3H, s); 3.60 (2H, s); 2.30 (6H, s).

60C 3-Dimethylaminomethylbenzoic Acid

This was prepared following the method of Example 31B, using the ester of Example 60B (1.20 g, 6.2 mmol) and LiOH.H$_2$O (540 mg, 13 mmol). The crude product was purified by flash chromatography on silica gel (eluant:CHCl$_3$:MeOH:AcOH 25:10:1 v/v/v) to give the title compound (750 mg, 68%).

60D N-((3RS)-1-tert-Butylcarbonylmethyl-2,3-dihydro-2-oxo-5-phenyl-1H-1,4-benzodiazepin-3-yl)-N'-(3-dimethylaminomethylphenyl)urea (Scheme 1, Step (iii))

The benzodiazepine of Example 2B was hydrogenated as described in Example 1C and the resultant amine (192 mg, 0.55 mmol) in toluene (5 ml) was treated with the isocyanate prepared using the acid of Example 60C (250 mg, 1.4 mmol) following the method of Example 38. The product was purified by flash chromatogaphy on silica gel (eluant $CHCl_3$:MeOH:AcOH 20:2:1 v/v/v) and crystallised from acetonitrile to give a white solid (50 mg, 17%, >99% pure by HPLC).

NMR ($CDCl_3$) δ7.55–6.90 (15H, m); 5.57 (1H, d, J=8 Hz); 4.80 (1H, d, J=17 Hz); 4.70 (1H, d, J=17 Hz); 3.40 (2H, s); 2.25 (6H, s); 1.15 (9H, s).

M.S. (FAB, +ve ion) m/e 526.3 [M+H]

EXAMPLE 61

N-((3RS)-2-tert-Butylcarbonylmethyl-2,3-dihydro-2-oxo-5-(2-pyridyl)-1H-1,4-benzodiazepin-3-yl)-N'-(3-(N-ethyl-N-methylamino)phenyl)urea. Compound 62

The benzodiazepine of Example 27A was deprotected as described in Example 27B and the resultant amine (200 mg, 0.57 mmol) in toluene (5 mls) was treated with the isocyanate prepared using the acid of Example 58B (250 mg, 1.4 mmol) following the method of Example 38. The product was purified by flash chromatography on silica gel (eluant EtOAc:hexane fr 90:10 v/v) to give the title compound which was lyophilised from $MeCN/H_2O$ to give a white solid (125 mg, 42%, >95% pure by HPLC).

$R_f$ (EtOAc:hexane fr 90:10) 0.23.

M.S. (FAB, +ve ion) m/e 527.3 [M+H]

EXAMPLE 62

N-((3RS)-1-tert-3-Butylcarbonylmethyl-2,3-dihydro-2-oxo-5-(2-pyridyl)-1H-1,4-benzodiazepin-3-yl)-N'-(3-dimethylaminomethylphenyl)urea. Compound 63

The benzodiazepine of Example 27A was deprotected as described in Example 27B and the resultant amine (200 mg, 0.57 mmol) in toluene (5 ml) was treated with the isocyanate prepared using the acid of Example 60C (250 mg, 1.4 mmol) following the method of Example 38. The product was purified by flash chromatogaphy on silica gel (eluant $CHCl_3$:MeOH:AcOH 18:4:1 v/v/v) to give the title compound which was crystallised from EtOAc-hexane fr to give a white solid (76 mg, 25%, >99% pure by HPLC).

NMR ($CDCl_3$) δ8.50 (1H, d, J=8 Hz); 8 .00–7.20 (12H, m); 6.80 (1H, d, J=8 Hz); 5.60 (1H, d, J=8 Hz); 4.80 (1H, d, J=17 Hz); 4.50 (1H, d, J=17 Hz); 3.40 (2H, s); 2.20 (6H, S); 1.20 (9H, s).

M.S. (FAB, +ve ion) m/e 527.3 [M+H]

EXAMPLE 63

N-((3RS)-1-tert-Butylcarbonylmethyl-2,3-dihydro-2-oxo-5-(2-pyridyl)-1H-1,4-benzodiazepin-3-yl)-N'-(3-diethylaminophenyl)urea. Compound 63

The benzodiazepine of Example 27A was deprotected as described in Example 27B and the resultant amine (200 mg, 0.57 mmol) in toluene (5 ml) was treated with the isocyanate prepared using the acid of Example 59C (212 mg, 1.1 mmol) following the method of Example 38. The product was purified by flash chromatogaphy on silica gel (eluant EtOAc:hexane fr 75:25 v/v) to give the title compound which was crystallised from acetonitrile to give a white solid (200 mg, 65%, >99% pure by HPLC).

NMR ($CDCl_3$) δ8.60 (1H, d, J=8 Hz); 8.17 (1H, d, J=8 Hz); 7.70–6.90 (10H, m); 6.40 (2H, m); 5.75 (H, d, J=8 Hz); 4.90 (1H, d, J=17 Hz); 4.40 (1H, d, J=17 Hz); 3.30 (4H, q, J=7 Hz); 1.20 (9H, s); 1.15 (6H, t, J=8 Hz).

M.S. (FAB, +ve ion) m/e 541.4 [M+H]

EXAMPLE 64

N-((3R)-1-tert-Butylcarbonylmethyl-2,3-dihydro-2-oxo-5-phenyl-1H-1,4-benzodiazepin-3-yl)N'-(3-dimethylaminophenyl)urea. Compound 65

This was prepared from the resolved aminobenzodiazepine of Example 26 (1.88 g, 5.4 mmol) following the method of Example 38. The product was purified by flash chromatography on silica gel (eluant EtOAc:hexane fr 55:45 v/v) and then lyophilised from dioxan-$H_2O$ to give the title compound as a white solid (1.72 g, 62%, >98% pure by HPLC).

$R_f$ (EtOAc:Hexane fr 60:40 v/v) 0.21.

M.S. (FAB, +ve ion) m/e 512.3 [M+H]

$[\alpha]_D$=+97.3° (c=0.776, $CHCl_3$)

EXAMPLE 65

N-((3RS)-1-tert-Butylcarbonylmethyl-2,3-dihydro-2-oxo-5-(4-methylphenyl)-1H-1,4-benzodiazepin-3-yl)-N'-(3-methylphenyl)urea. Compound 66

65A (3RS)-3-Benzyloxycarbonylamino-1-tert-butylcarbonylmethyl-2,3-dihydro-5-(4-methylphenyl)-1H-1,4-benzodiazepin-2-one (Scheme 1, Step (i))

This was prepared from (3RS)-3-benzyloxycarbonylamino-2,3-dihydro-5-(4-methylphenyl)-1H-1,4-benzodiazepine-2-one (200 mg, 0.53 mmol, prepared by analogy to the Bock benzodiazepine) following the method of Example 2B. The product was purified by flash chromatography on silica gel (eluant EtOAc:hexane fr 35:65 v/v) to give the title compound as a colourless oil (252 mg, 96%).

NMR ($CDCl_3$) δ7.53 (3H, m); 7.41–7.13 (9H, m); 6.68 (1H, d, J=8 Hz); 5.44 (1H, d, J=8 Hz); 5.18 (2H, s); 5.00 (1H, d, J=17 Hz); 4.67 (1H, d, J=17 Hz); 2.42 (3H s); 1.28 (9H, s).

65B N-((3RS)-1-tert-Butylcarbonylmethyl-2,3-dihydro-2-oxo-5-(4-methylphenyl)-1H-1,4-benzodiazepin-3-yl)-N'-(3-methylphenyl)urea (Scheme 1, Step (ii))

This was prepared from the benzodiazepine of Example 65A following the method of Example 14B. The product was purified by flash chromatography on silica gel (eluant EtOAc:hexane fr 37:63 v/v) and lyophilised from dioxan-$H_2O$ to give the title compound as a white solid (118 mg, 47%, >98% pure by HPLC).

$R_f$ (ETOAc/Hexane 40:60 v/v) 0.18

NMR ($CDCl_3$) δ9.02–8.92 (3H, m); 8.82–8.20 (11H, m); 7.10 (1H, d, J=5 Hz); 6.32 (1H, d, J=8 Hz); 6.17 (1, d, J=8 Hz); 3.82 (3H, s); 3.72 (3H, s); 2.66 (9H, s).

M.S. (FAB, +ve ion) m/e=497.3 [M+H]

EXAMPLE 66

N-((3R)-1-tert-Butylcarbonylmethyl-2,3-dihydro-2-oxo-5-phenyl-1H-1,4-benzodiazepin-3-yl)-N'-(3-aminophenyl)urea. Compound 67

66A N-((3R)-1-tert-Butylcarbonylmethyl-2,3-dihydro-2-oxo-5-phenyl-1H-1,4-benzodiazepin3-yl)-N'-(3-nitrophenyl)urea (Scheme 1, Step (ii))

The resolved aminobenzodiazepine of Example 26 was treated with m-nitrophenyl isocyanate as described in Example 45 to provide a colourless oil (490 mg, 94%).

Data identical to Example 45.

66B N-((3R)-1-tert-Butylcarbonylmethyl-3-dihydro-2-oxo-5-phenyl-1H-1,4-benzodiazepin-3-yl)-N'-(3-aminophenyl)urea The benzodiazepine of Example 66A (245 mg, 0.468 mmol) was taken up in 1M ammonium chloride (8 ml) and treated with zinc dust (620 mg) and the mixture stirred vigorously as ethanol (8 ml) was added slowly to the mixture. After ½ hour the mixture was filtered and evaporated. The residue was purified by flash chromatogaphy on silica gel (eluant EtOAc:hexane fr 80.20 v/v) and lyophilised from MeCN—$H_2O$ to give the title compound as a white solid (115 mg, 67%, >980% pure by HPLC).

$R_f$ (EtOAc=0.64.
$^1$H NMR (CDCl$_3$) δ7.8–7.0 (11H, m); 6.9 (1H, t, J=8.5 Hz); 6.75 (m, 2H); 6.35 (1H, d, J=8.5 Hz); 5.7 (1H, d, J=8.5 Hz); 4.95 (2H, s); 3.75 (2H, br.s.); 1.21 (9H, s).
$[α]_D$=+25° (c=0.993, MeOH)
M.S. (FAB, +ve ion) $^m/_e$=484.3 [M+H]

EXAMPLE 67

N-((3RS)-1-tert-Butylcarbonylmethyl-7-chloro-2,3-dihydro-2-oxo-phenyl-1H-1,4-benzodiazepin-3-yl)-N'-(3-methylphenyl)urea. Compound 74

67A (3RS)-3-Benzyloxycarbonylamino-1-tert-butylcarbonylmethyl-7-chloro-2,3-dihydro-5-phenyl-1H-1,4-benzodiazepin-2-one (Scheme 1, Step (i))

This was prepared from (3RS)-3-benzyloxycarbonylamino-7-chloro-2,3-dihydro-5-phenyl-1H-1,4-benzodiazepin-2-one (640 mg, 1.46 mmol, prepared by analogy with the Bock benzodiazepine), sodium hydride (62 mg of an 80% dispersion in oil, 2.04 mmol) and 1-bromopinacolone (537 mg, 3 mmol) following the method of Example 1B. The crude product was purified by flash chromatography on silica gel (eluant EtOAc:hexane fr 30:70 v/v) to afford the title compound (700 mg, 93%).

NMR (CDCl$_3$) δ7.70–7.30 (13H, m); 6.8 (1H, d, J=8 Hz); 5.60 (1H, d, J=8 Hz); 5.30(2H, s); 5.05 (1H,d, J=17 Hz); 4.80 (1H, d, J=17 Hz); 1.35 (9H, s).

67B N-((3RS)-1-tert-Butylcarbonylmethyl-7-chloro-2,3-dihydro-2-oxo-5-phenyl-1H-1,4-benzodiazepin-3-yl)-N'-(3-methylphenyl)urea (Scheme 1, Step (ii))

This was prepared following the method of Example 27B using the benzodiazepine of Example 67A (270 mg, 0.52 mmol), BBr$_3$ (3.4 ml, 1.0 M sol in CH$_2$Cl$_2$) and m-tolyl isocyanate (90 μl, 0.66 mmol). The product was purified by chromatography (eluant EtOAc:hexane fr 40:60 v/v) to provide the title compound which was freeze dried from MeCN/H$_2$O to give the product as a white solid (83 mg, 31%, >99% by HPLC).

NMR (CDCl$_3$) δ7.70–6.95 (14H, m); 5.80 (1H, d, J=8 Hz); 4.90 (2H, s); 2.40 (3H, s); 1.25 (9H, s).
M.S. (FAB, +ve ion) m/e 517.2 [M+H]

EXAMPLE 68

N-((3RS)-1-tert-Butylcarbonylmethyl-7-chloro-2,3-dihydro-2-oxo-5-phenyl-1H-1,4-benzodiazepin-3-yl)-N'-(3-dimethylaminophenyl)urea. Compound 75

This was prepared following the method of Example 27B using the benzodiazepine of Example 67A (430 mg, 0.83 mmol), BBr$_3$ (5.0 ml, 1.0 M sol in CH$_2$Cl$_2$) and the isocyanate prepared using 3-dimethylaminobenzoic acid (400 mg, 2.4 mmol) following the method of Example 38. The product was purified by flash chromatography on silica gel (eluant EtOAc:hexane fr 45:55 v/v) to provide the title compound which was lyophilised from MeCN/H$_2$O to give a white solid (100 mg, 22%, >98% pure by HPLC).

NMR (CDCl$_3$) δ7.60–6.90 (12H, m); 6.50 (1H, d, J=8 Hz); 6.40 (1H, d, J=8 Hz); 5.60 (1H, d, J=8 Hz); 4.75 (2H, s); 2.90 (6H, s); 2.10 (3H, s); 1.15 (9H, s).
M.S. (FAB, +ve ion) m/e 546.3 [M+H]

EXAMPLE 69

N-((3RS)-1-tert-Butylcarbonylmethyl)-7-chloro-2,3-dihydro-2-oxo-5-(2-chlorophenyl)-1H-1,4-benzodiazepin-3-yl)-N'-(3-methylphenyl)urea. Compound 76

This was prepared following the method of Example 27B using the benzodiazepine of Example 54A (170 mg, 0.31 mmol), BBr$_3$ (2 ml, 1.0 M sol in CH$_2$Cl$_2$) and m-tolyl isocyanate (60 μl, 0.4 mmol). The product was purified by flash chromatography on silica gel (eluant EtOAc:hexane fr 35:65 v/v) to provide the title compound which was lyophilised from MeCN/H$_2$O to give a white solid (39 mg, 51%, >99% pure by HPLC).

$R_f$ (EtOAc:hexane fr 40:60) 0.25.
M.S. (FAB, +ve ion) m/e 551.2 [M+H]

EXAMPLE 70

N-((3RS)-1-tert-Butylcarbonylmethyl-2,3-dihydro-8-methyl-2-oxo-5-phenyl-1H-1,4-benzodiazepin-3-yl)-N'-(3-methylphenyl)urea. Compound 77

70A (3RS)-3-Benzyloxycarbonylamino-tert-1-butylcarbonylamino-2,3-dihydro-8-methyl-5-phenyl-11–14-benzodiazepin-2-one (Scheme 1, Step (i))

This was prepared from (3RS)-3-benzyloxycarbonylamino-2,3-dihydro-8-methyl-5-phenyl-1H-1,4-benzodiazepin-2-one (240 mg, 0.64 mmol, prepared by analogy to the Bock benzodiazepine) following the method of Example 2B. The product was purified by flash chromatography on silica gel (eluant EtOAc:hexane fr 30:70 v/v) to give the title compound as a colourless oil (289 mg, 91%).

$R_f$ (EtOAc:hexane fr 30:70 v/v) 0.17.
NMR (CDCl$_3$) δ7.67 (2H, m); 7.4 (9H, m); 7.25 (1H, d, J=8 Hz); 6.96 (1H, s); 6.70 (1H, d, J=9 Hz); 5.47 (1H, d, J=9 Hz); 5.19 (2H, s); 4.98 (1H, d, J=18 Hz); 4.70 (1H, d, J=18 Hz); 2.46 (3H, s); 1.30 (9H, s).

70B N-((3RS)-1-tert-Butylcarbonylmethyl-2,3-dihydro-8-methyl-2-oxo-5-phenyl-1H-1,4-benzodiazepin-3-yl)-N'-(3-methylphenyl)urea (Scheme 1, Step (ii))

This was prepared from the benzodiazepine of Example 70A (289 mg, 0.58 mmol) following the method of Example 14B. The product was purified by flash chromatography on silica gel (eluant EtOAc:hexane fr 37:63 v/v) and lyophilised from dioxan-H$_2$O to give the title compound as a white solid (106 mg, 37%, >98% pure by HPLC).

$R_f$ (EtOAc:hexane fr 40:60 V/V) 0.18.
NMR (CDCl$_3$) δ7.67 (2H, m); 7.46 (2H, m); 7.26–6.79 (9H, m); 5.68 (1H, d, J=7 Hz); 4.93 (1H, d, J=11 Hz); 4.75 (1H, d, J=11 Hz); 2.45 (3H, s); 2.33 (3H, s); 1.27 (9H, s).
M.S. (FAB, +ve ion) m/e=497.2 [M+H]

Compounds 53, 68–73, 78 and 79 are obtainable by methods analogous to those described in the above Examples.

The compounds of the present invention are potent and selective antagonists at the CCK-B receptor and inhibit gastric acid secretion stimulated by pentagastrin. The methods of measuring these activities are described below:

Measurement of Binding Affinity for CCK-B Receptors

About 100 SD rats were decapitated without anaesthesia, the whole brain was immediately excised from each of the rats and homogenized in 10-fold volume of 0.32 M aqueous solution of sucrose by the use of a Teflon-coated homogenizer, the homogenate thus obtained was centrifuged for ten minutes at 900 g by the use of a cooled centrifuge, and the supernatant was further centrifuged for 15 minutes at 11500 g. The precipitate thus obtained was dispersed in 50 mM Tris-HCl buffer (pH 7.4) containing 0.08% Triton X-100, this suspension was allowed to stand for 30 minutes and again centrifuged for 15 minutes at 11500 g, the precipitate thus obtained was washed twice with 5 mM Tris-HCl buffer and twice with 50 mM Tris-HCl buffer in that order with centrifugal separation, the washed precipitate was suspended in 50 mM Tris-HCl buffer, and the suspension thus obtained was stored at −80° C. until the membrane preparation was required.

The membrane preparations were warmed to room temperature, diluted with 10 mM HEPES buffer (containing 130 mM NaCl, 5 mM $MgCl_2$, 1 mM EGTA and 0.25 mg/ml bacitracin; pH 6.5) and incubated at 25° C. for 120 minutes in the presence of [$^{125}$I]BH-CCK-8 and the test compound, then separated by suction filtration. Non-specific binding was determined in the presence of 1 μM CCK-8. The amount of labelled ligand bound to the receptor was measured by the use of a γ-counter; $IC_{50}$ values were determined, being that concentration of test compound required to inhibit specific binding by 50%.

Measurement of Binding Affinity for CCK-A Receptors

The pancreas of an SD rat was homogenized in a 20-fold volume of 50 mM Tris-HCl buffer (pH 7.7) by the use of a Polytrone-type homogenizer, the homogenate was twice centrifuged for 10 minutes at 50000 g by the use of an ultra-centrifuge, the precipitate thus obtained was suspended in a 40-fold volume of 50 mM Tris-HCl buffer (containing 0.2% BSA, 5 mM $MgCl_2$, 0.1 mg/ml bacitracin and 5 mM DTT; pH 7.7), and the suspension was stored at −80° C. until the membrane preparations were required.

The membrane preparations were then warmed to room temperature, diluted 1:10 with the buffer and incubated at 37° C. for 30 minutes in the presence of [$^3$H]L-364,718 and the test compound then separated by suction filtration. Non-specific binding was determined in the presence of 1 μM L-364,718. The amount of labelled ligand bound to the receptor was measured by the use of a liquid scintillation counter; $IC_{50}$ values were determined, being that concentration of test compound required to inhibit specific binding by 50%.

A high affinity for the CCK-A receptor in a gastrin/CCK-B antagonist is thought to be undesirable as it may lead to side-effects such as cholestasis and gall stone formation during therapy. Therefore it is preferable for the therapeutic agent to be selective for the CCK-B receptor. This selectivity is expressed by the ratio $IC_{50}$. (CCK-A)/$IC_{50}$ (CCK-B); the higher the value of this ratio the better is the selectivity.

The table below summarises CCK-B and CCK-A binding data for examples of preferred compounds, as well as the A/B ratio. Many compounds display a marked increase in CCK-B receptor binding affinity when compared to the compound of Example 281 of U.S. Pat. No. 4,820,834 (also known as L-365,260). Several compounds also show much greater selectivity for the CCK-B receptor over the CCK-A receptor than that reported for the compound of Example 281 of U.S. Pat. No. 4,820,834.

| | Receptor binding affinity $IC_{50}$ (nM) | | |
|---|---|---|---|
| COMPOUND | CCK-B | CCK-A | A/B Ratio |
| Compound of Example 281 of U.S. Pat. No. 4,820,834 | 29 | 12,000 | 410 |
| Example 4 | 0.23 | 449 | 1,900 |
| Example 9 | 7.3 | >10,000 | >1,400 |
| Example 12 | 1.4 | >10,000 | >7,100 |
| Example 13 | 0.11 | >10,000 | >91,000 |
| Example 14 | 0.12 | 2,600 | 22,000 |
| Example 17 | 0.07 | 2,500 | 36,000 |
| Example 19 | 0.92 | 1,00 | 1,200 |
| Example 22 | 3.5 | >10,000 | >2,900 |
| Example 23 | 0.08 | 870 | 11,000 |
| Example 24 | 0.97 | >10,000 | >10,000 |
| Example 25 | 0.65 | >10,000 | >15,000 |
| Example 31 | 0.53 | 3,400 | 6,400 |
| Example 32 | 0.28 | 480 | 1,700 |
| Example 34 | 0.38 | >10,000 | >26,000 |
| Example 35 | 1.1 | 1,900 | 1,700 |
| Example 36 | 0.57 | 720 | 1,300 |
| Example 37 | 1.1 | 5,600 | 5,100 |
| Example 39 | 0.10 | 240 | 2,400 |
| Example 41 | 6.2 | 6,700 | 1,100 |
| Example 42 | 0.07 | 360 | 5,100 |
| Example 44 | 0.17 | 1,600 | 9,400 |
| Example 45 | 0.16 | 590 | 3,700 |
| Example 56 | 0.11 | 120 | 1,100 |
| Example 66 | 0.5 | 950 | 1,900 |

Measurement of Inhibition of Pentagastrin-stimulated Gastric Acid Secretion in Rat A cannula was inserted into the trachea of a rat anaesthetised with urethane (intraperitoneally administered, 1.25 g/Kg), its abdominal wall was incised to expose the gastric and duodenal portions, and a polyethylene cannula was set in the anterior stomach after ligation of the cardia. The duodenum was then subjected to slight section, a polyethylene cannula was inserted from the incised portion toward the stomach, and the pylorus was ligated to fix the cannula.

Physiological saline (with pH adjusted to 7.0) was perfused from the anterior stomach toward the pylorus at a rate of 3 ml/min, and the gastric-acid secretion was measured by continuous titration of the perfusate by the use of a pH-stat (AUT-201; product of Toa Electronics, Ltd.). The continuous titration was carried out by using 25 mM NaOH solution until the pH reached 7.0, and the result was expressed as the amount of gastric acid secreted for every 10 minutes ($\mu E_q$/10 min.). Pentagastrin was intravenously administered at a rate of 15 μg/Kg/hr.

The secretion of gastric acid increased upon administration of pentagastrin, reaching the maximum level after 60 minutes and stably maintaining this level after that. A test drug was then intravenously administered, and the secretion of gastric acid was measured; $ED_{50}$ values were determined, being the amount of the drug required to reduce the amount of secreted gastric acid down to 50% of the maximum level.

Representative $ED_{50}$ values are shown below.

| ED50 (μmo/kg) | |
|---|---|
| | $ED_{50}$ (μmol/kg) |
| Compound of Example 281 of U.S. Pat. No. 4,820,834 | 4.2 |
| Compound of Example 4 | 0.016 |
| Compound of Example 5 | 0.018 |
| Compound of Example 7 | 0.047 |

Measurement of Inhibition of Pentagastrin-stimulated Gastric Acid Secretion in doc Assays were performed using male beagle dogs (7–12 kg) two months after surgical preparation of Heidenhain pouches following the conventional procedure. Each dog was used only once per week.

The animals were deprived of food with free access to water for 18 hr prior to the experiment. The gastric juice was collected from the gastric cannula by gravity drainage every 15 min, and acid output was determined by automatic titration with 0.05 N NaOH to pH 7.0 (Comtite-7, Hiranuma, Tokyo, Japan). Drugs were administered orally 3 hr after the start of the pentagastrin (8 μg/kg/hr) infusion. The effect of each drug was calculated as the percentage inhibition of stimulated acid output. The table below shows the maximum inhibition observed for representative Examples. Each result is a mean for 3–5 animals.

|  | Inhibition (dose) |
| --- | --- |
| Compound of Example 281 of U.S. Pat. No. 4,820,834 | 0% (100 μmol/kg) |
| Compound of Example 26 | 53% (3 μmol/kg) |
| Compound of Example 27 | 66% (3 μmol/kg) |
| Compound of Example 38 | 100% (3 μmol/kg) |
| Compound of Example 64 | 100% (3 μmol/kg) |

The experiments described above demonstrate that the compounds of the present invention are potent selective gastrin/CCK-B antagonists and inhibit the stimulation of gastric acid release due to pentagastrin. They are therefore useful in the treatment of disease states in which gastrin or CCK-B receptor is implicated as a mediating factor. Such disease states would include disorders of the gastro-intestinal system, for example gastric and duodenal ulcers, gastritis, reflux esophagitis, Zollinger-Ellison syndrome, gastrin-sensitive pancreas, and gastrin-sensitive tumors. Disorders of the central nervous system such as anxiety and psychoses would also be amenable to treatment with the compounds of this invention. The compounds can also be used in the control of appetite and pain.

The compounds of this invention and salts thereof can be administered orally (including sublingual administration) or parenterally in the form of tablets, powders, capsules, pills, liquids, injections, suppositories, ointments and adhesive plasters.

The carrier and excipient for pharmaceutical manufacturing can be a solid or liquid, non-toxic medicinal substance, such as lactose, magnesium stearate, starch, talc, gelatin, agar, pectin, gum arabic, olive oil, sesame oil, cocoa butter, ethylene glycol and other commonly employed materials.

Examples of formulations using the compounds of this invention are described below.

| Examples of tablet preparation | | |
| --- | --- | --- |
| Composition | 20 mg-Tablet | 40 mg-Tablet |
| Compound of Example 4 | 20 mg | 40 mg |
| Lactose | 73.4 | 80 |
| Corn Starch | 18 | 20 |
| Hydroxypropylcellulose | 4 | 5 |
| Carboxymethylcellulose Ca | 4 | 4.2 |
| Mg Stearate | 0.6 | 0.8 |
| Total | 120 mg | 150 mg |

Preparation of 20 mg-tablets

Compound of Example 4 (100 g), lactose (367 g) and corn starch (90 g) were homogeneously mixed together by the use of a flow granulating coater (product of (Ohgawara Seisakusho), 10% aqueous solution of hydroxypropylcellulose (200 g) was sprayed into the mixture, and granulation was then performed. After drying, the granules were filtered through a 20-mesh sieve, 20 g of carboxymethylcellulose Ca and 3 g of magnesium stearate were then added, and the mixture, was treated in a rotary tablet machine equipped with a pestle of 7 mm×8.4 R (product of Hata Tekkosho), thus producing tablets each weighing 120 mg.

Preparation of 40 mg-tablets

Compound of Example 4 (140 g), lactose (280 g) and corn starch (70 g) were homogeneously mixed together by the use of a flow granulating coater (product of Ohgawara Seisakusho), 10% aqueous solution of hydroxypropylcellulose (175 g) was sprayed into the mixture, and granulation was then performed. After drying, the granules were filtered through a 20-mesh sieve, 14.7 g of carboxymethylcellulose Ca and 2.8 g of magnesium stearate were then added, and the mixture was treated in a rotary tablet machine equipped with a pestle of 7.5 mm×9R (product of Hata Tekkosho), thus producing tablets each weighing 150 mg.

The clinical dosage of the compounds of this invention will be determined by the physician taking into account the precise illness, and the body weight, age, sex, medical history and other factors of the patient to be treated. In general the dosage when administered orally will be between 1 and 1000 mg/day in either a single dose or sub-divided into smaller multiple doses.

We claim:

1. A method of treating a disease induced by failure of a physiological function controlled by gastrin or central CCK-B receptor, comprising the step of administering to a subject in need of such treatment a therapeutically effective amount of a benzodiazepine compound of formula I, or a pharmaceutically acceptable salt thereof:

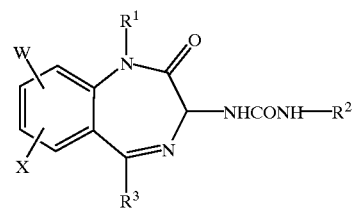

I wherein (a) $R^1$ is —$CH_2CHOH(CH_2)_aR^4$ or a ketone group —$CH_2CO(CH_2)_aR^5$ in which a is 0 or 1, and $R^4$ and $R^5$ are selected from ($C_1$–$C_8$)alkyl groups, ($C_3$–$C_8$) cycloalkyl and adamantyl groups, which may be unsubstituted or substituted by one or two ($C_1$–$C_8$)alkyl groups, and groups of formulae II and III;

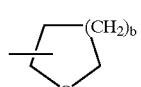

II

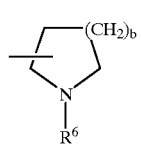

III in which $R^6$ is H or ($C_1$–$C_8$)alkyl or —CO—($C_1$–$C_6$) alkyl and b is 1 or 2;

(b) $R^2$ and $R^3$ are independently selected from 5- and 6-membered aromatic carbocyclic and 5- and 6-membered heterocyclic groups with one heteroatom selected from the groups consisting of N, O and S, where $R^2$ and $R^3$ each may have 1 or 2 substituents selected from the group consisting of a halogen atom, an amino group, a hydroxyl group, a nitro group, a cyano group, an alkyl group, an alkoxy group, a hydroxyamino group, an alkylamino group and a dialkylamino group, a carbamoyl group, a formylamino group, an alkylaminoalkyl group, a dialkylaminoalkyl group, a —$(CH_2)_c$—$CO_2H$ group in which c is 0–2 and a —$(CH_2)_c$—$SO_3H$ in which c is 0–2, wherein alkyl portions of the recited groups consist of 1 to 6 carbon atoms; and (c) W and X are selected independently from halogen and hydrogen atoms and $(C_1-C_8)$alkyl and $(C_1-C_8)$alkoxy groups, comprising the step of administering to a subject in need of such treatment a therapeutically effective amount of said compound.

2. A method according to claim 1, wherein $R^4$ is linear or branched $(C_4-C_7)$ alkyl or is of formula II or III:

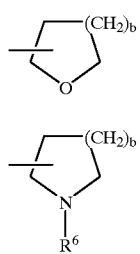

in which $R^6$ is H or $(C_1-C_3)$ alkyl or —CO—$(C^1-C_3)$alkyl and b is 1 or 2.

3. A method according to claim 1, wherein at least one of $R^2$ and $R^3$ is unsubstituted phenyl or unsubstituted 2-, 3- or 4-pyridyl.

4. A method according to claim 1, wherein $R^1$ is —$CH_2CO(CH_2)_aR^5$;

$R^2$ is unsubstituted phenyl; phenyl having a meta substituent chosen from F, Cl, Br, OH, $OCH_3$, $NH_2$, $NMe_2$, $NO_2$, Me, $(CH_2)_c$—$CO_2H$, CN, NHMe, NMeEt, $NEt_2$, $CH_2NMe_2$, NHCHO and $(CH_2)_c$—$SO_3H$ where c is 0–2; or 2-, 3- or 4-pyridyl optionally with a substituent selected from F, Cl, $CH_3$ and $CO_2H$; and $R^3$ is phenyl or 2-, 3- or 4-pyridyl.

5. A method according to claim 1, where $R^1$ is —$CH_2CHOH(CH_2)_aR^4$ and $R^2$ and $R^3$ are $R^2$ is unsubstituted phenyl; phenyl having a meta substituent chosen from F, Cl, Br, OH, $OCH_3$, $NH_2$, $NMe_2$, $NO_2$, Me, $(CH_2)_c$—$CO_2H$, CN, NHMe, NMeEt, $NEt_2$, $CH_2NMe_2$, NHCHO and $(CH_2)_c$—$SO_3H$ where c is 0–2; or 2-, 3- or 4-pyridyl optionally with a substituent selected from the F, Cl, $CH_3$ and $CO_2H$; and $R^3$ is phenyl or 2-, 3- or 4-pyridyl.

6. A method according to claim 1, wherein the absolute configuration at the 3-position of the benzodiazepine ring is R (as shown in IV)

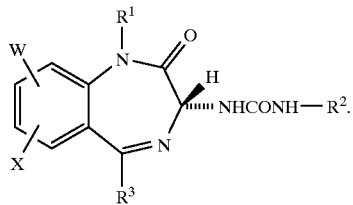

7. A method according to claim 1 wherein W and X are H.

8. A method according to claim 1, comprising administration of:

1. N-((3RS)-1-tert-Butylcarbonylmethyl-2,3-dihydro-2-oxo-5-phenyl-1H-1,4-benzodiazepin-3-yl)-N'-(3-methylphenyl)urea;
2. N-((3RS)-1-Diethylmethylcarbonylmethyl-2,3-dihydro-2-oxo-5-phenyl-1H-1,4-benzodiazepin-3-yl)-N'-(3-methylphenyl)urea;
3. N-((3RS)-1-Cyclobutylcarbonylmethyl-2,3-dihydro-2-oxo-5-phenyl-1H-1,4-benzodiazepin-3-yl)-N'-(3-methylphenyl)urea;
4. N-((3RS)-1-Cyclopentylcarbonylmethyl-2,3-dihydro-2-oxo-5-phenyl-1H-1,4-benzodiazepin-3-yl)-N'-(3-methylphenyl)urea;
5. N-((3RS)-1-Cyclohexylcarbonylmethyl-2,3-dihydro-2-oxo-5-phenyl-1H-1,4-benzodiazepin-3-yl)-N'-(3-methylphenyl)urea;
6. N-((3RS)-1-Cycloheptylcarbonylmethyl-2,3-dihydro-2-oxo-5-phenyl-1H-1,4-benzodiazepin-3-yl)-N'-(3-methylphenyl)urea;
7. N-((3RS)-Cycloheptylcarbonylmethyl-2,3-dihydro-2-oxo-5-phenyl-1H-1,4-benzodiazepin-3-yl)-N'-(3-chlorophenyl)urea;
8. N-((3RS)-1-Cyclopentylcarbonylmethyl-2,3-dihydro-2-oxo-5-(2-pyridyl)-1H-1,4-benzodiazepin-3-yl-N'-(3-methylphenyl)urea;
9. N-((3RS)-1-Cyclopentylcarbonylmethyl-2,3-dihydro-2-oxo-5-(3-pyridyl)-1H-1,4-benzodiazepin-3-yl)-N'-(3-methylphenyl)urea;
10. N-((3RS)-1-Cyclopentylcarbonylmnethyl-2,3-dihydro-2-oxo-5-(4-pyridyl)-1H-1,4-benzodiazepin-3-yl)-N'-(3-methylphenyl)urea;
11. N-((3RS)-1-Cyclopentylcarbonylmethyl-2,3-dihydro-2-oxo-5-phenyl-1H-1,4-benzodiazepin-3-yl)-N'-(3-carboxyphenyl)urea;
12. N-((3R)-1-Cyclopentylcarbonylmethyl-2, 3-dihydro-2-oxo-5-phenyl-1H-1,4-benzodiazepin-3-yl)-N'-(3-methylphenyl)urea;
13. N-((3S)-1-Cyclopentylcarbonylmethyl-2,3-dihydro-2-oxo-5-phenyl-1H-1,4-benzodiazepin-3-yl)-N'-(3-methylphenyl)urea;
14. N-((3RS)-2,3-Dihydro-2-oxo-5-phenyl-1-((2R)-2-pyrrolidylcarbonylmethyl)-1H-1,4-benzodiazepin-3-yl)-N'-(3-methylphenyl)urea;
15. N-((3RS)-2,3-Dihydro-2-oxo-5-phenyl-1-((2S)-2-pyrrolidylcarbonylmethyl)-1H-1,4-benzodiazepin-3-yl)-N'-(3-methylphenyl)urea;
16. N-((3RS)-1-((2R)-1-Acetyl-2-pyrrolidylcarbonylmethyl)-2,3-dihydro-2-oxo-5-phenyl-1H-1,4-benzodiazepin-3-yl)-N'-(3-methylphenyl)urea;
17. N-((3RS)-1-((2S)-1-Acetyl-2-pyrrolidylcarbonylmethyl)-2,3-dihydro-2-oxo-5-phenyl-1H-1,4-benzodiazepin-3-yl)-N'-(3-methylphenyl)urea;
18. N-((3RS)-1-((2RS)-2-Cyclopentyl-2-hydroxyethyl)-2,3-dihydro-2-oxo-5-phenyl-1H-1,4-benzodiazepin-3-yl)-N'-(3-methylphenyl)urea;

19. N-((3RS)-1-((2SR)-2-Cyclopentyl-2-hydroxyethyl)-2,3-dihydro-2-oxo-5-phenyl-1H-1,4-benzodiazepin-3-yl)-N'-(3-methylphenyl)urea;
20. N-((3R)-1-((2R)-2-Cyclopentyl-2-hydroxyethyl)-2,3-dihydro-2-oxo-5-phenyl-1H-1,4-benzodiazepin-3-yl)-N'-(3-methylphenyl)urea;
21. N-((3R)-1-((2S)-2-Cyclopentyl-2-hydroxyethyl)-2,3-dihydro-2-oxo-5-phenyl-1H-1,4-benzodiazepin-3-yl)-N'-(3-methylphenyl)urea;
22. N-((3RS)-1-Cyclopentylcarbonylmethyl-2,3-dihydro-2-oxo-5-phenyl-1H-1,4-benzodiazepin-3-yl)-N'-(3-cyanophenyl)urea;
23. N-((3RS)-1-tert-Butylcarbonylmethyl-2,3-dihydro-2-oxo-5-phenyl-1H-1,4-benzodiazepin-3-yl)-N'-(3-cyanophenyl)urea;
24. N-((3RS)-1-Cyclopentylcarbonylmethyl-2,3-dihydro-2-oxo-5-phenyl-1H-1,4-benzodiazepin-3yl)-N'-(3-carboxymethylphenyl)urea;
25. N-((3RS)-1-(1-Adamantyl)carbonylmethyl-2,3-dihydro-2-oxo-5-phenyl-1H-1,4-benzodiazepin-3-yl)-N'-(3-methylphenyl)urea;
26. N-((3RS)-1-Cyclopentylcarbonylmethyl-2,3-dihydro-2-oxo-5-phenyl-1H-1,4-benzodiazepin-3-yl)-N'-(3-pyridyl)urea;
27. N-((3RS)-1-cyclopentylcarbonylmethyl-2,3-dihydro-2-oxo-5-phenyl-1H-1,4-benzodiazepin-3-yl)-N'-(6-methyl-2-pyridyl)urea;
28. N-((3RS)-1-(3-Cyclohexyl-3-methyl-2-oxo-butyl)-2,3-dihydro-2-oxo-5-phenyl-1H-1,4-benzodiazepin-3-yl)-N'-(3-methylphenyl)urea;
29. N-((3RS)-1-Cyclohexylmethylcarbonylmethyl-2,3-dihydro-2-oxo-5-phenyl-1H-1,4-benzodiazepin-3-yl)-N'-(3-methylphenyl)urea;
30. N-((3RS)-1-Cyclopentylmethylcarbonylmethyl-2,3-dihydro-2-oxo-5-phenyl-1H-1,4-benzodiazepin-3-yl)-N'-(3-methylphenyl)urea;
31. N-((3RS)-1-((1-Methylcyclohexyl)carbonylmethyl)-2,3-dihydro-2-oxo-5-phenyl-1H-1,4-benzodiazepin-3-yl)-N'-(3-methylphenyl)urea;
32. N-((3RS)-1-((1-Methylcyclopentyl)carbonylmethyl)-2,3-dihydro-2-oxo-5-phenyl-1H-1,4-benzodiazepin-3-yl)-N'-(3-methylphenyl)urea;
33. N-((3R)-1-Cyclopentylcarbonylmethyl-2,3-dihydro-2-oxo-5-phenyl-1H-1,4-benzodiazepin-3-yl)-N'-(3-carboxyphenyl)urea;
34. N-((3RS)-1-Cyclopentylcarbonylmethyl-2,3-dihydro-2-oxo-5-(2-pyridyl)-1H-1,4-benzodiazepin-3-yl)-N'-(3-carboxyphenyl)urea;
35. N-((3R)-1-((2RS)-2-Cyclopentyl-2-hydroxyethyl)-2,3-dihydro-2-oxo-5-phenyl-1H-1,4-benzodiazepin-3-yl)-N'-(3-carboxyphenyl)urea;
36. N-((3R)-1-((2R)-2-Cyclopentyl-2-hydroxyethyl)-2,3-dihydro-2-oxo-5-phenyl-1H-1,4-benzodiazepin-3-yl)-N'-(3-carboxyphenyl)urea;
37. N-((3RS)-1-Cyclopentylcarbonylmethyl-2,3-dihydro-2-oxo-5-phenyl-1H-1,4-benzodiazepin-3-yl)-N'-(3-carboxamidophenyl)urea;
38. N-((3R)-1-tert-Butylcarbonylmethyl-2,3-dihydro-2-oxo-5-phenyl-1H-1,4-benzodiazepin-3-yl)-N'-(3-methylphenyl)urea;
39. N-((3RS)-1-tert-Butylcarbonylmethyl-2,3-dihydro-2-oxo-5-(2-pyridyl)-1H-1,4-benzodiazepin-3-yl)-N'-(3-methylphenyl)urea;
40. N-((3RS)-1-tert-Butylcarbonylmethyl-2,3-dihydro-2-oxo-5-phenyl-1H-1,4-benzodiazepin-3-yl)-N'-(3-carboxyphenyl)urea;
41. N-((3RS)-1-tert-Amylcarbonylmethyl-2,3-dihydro-2-oxo-5-phenyl-1H-1,4-benzodiazepin-3-yl)-N'-(3-methylphenyl)urea;
42. N-((3RS)-1-tert-Amylcarbonylmethyl-2,3-dihydro-2-oxo-5-phenyl-1H-1,4-benzodiazepin-3-yl)-N'-(3-carboxyphenyl)urea;
43. N-((3RS)-1-tert-Butylcarbonylmethyl-2,3-dihydro-2-oxo-5-(2-pyridyl)-1H-1,4-benzodiazepin-3-yl)-N'-(3-dimethylaminophenyl)urea;
44. N-((3RS)-1-tert-Butylcarbonylmethyl-2,3-dihydro-2-oxo-5-(2-pyridyl)-1H-1,4-benzodiazepin-3-yl)-N'-(3-carboxyphenyl)urea;
45. N-((3RS)-1-Cyclopentylcarbonylmethyl-2,3-dihydro-2-oxo-5-phenyl-1H-1,4-benzodiazepin-3-yl)-N'-(3-dimethylaminophenyl)urea;
46. N-((3RS)-1-tert-Butylcarbonylmethyl-2,3-dihydro-2-oxo-5-phenyl-1H-1,4-benzodiazepin-3-yl)-N'-(3-dimethylaminophenyl)urea;
47. N-((3RS)-1-Cyclopentylcarbonylmethyl-2,3-dihydro-2-oxo-5-phenyl-1H-1,4-benzodiazepin-3-yl)-N'-(3-methoxyphenyl)urea;
48. N-((3RS)-1-tert-Butylcarbonylmethyl-2,3-dihydro-2-oxo-5-phenyl-1H-1,4-benzodiazepin-3-yl)-N'-(3-methoxyphenyl)urea;
49. N-((3RS)-1-Cyclopentylcarbonylmethyl-2,3-dihydro-2-oxo-5-phenyl-1H-1,4-benzodiazepin-3-yl)-N'-(3-nitrophenyl)urea;
50. N-((3RS)-1-tert-Butylcarbonylmethyl-2,3-dihydro-2-oxo-5-phenyl-1H-1,4-benzodiazepin-3-yl)-N'-(3-nitrophenyl)urea;
51. N-((3RS)-1-tert-Butylcarbonylmethyl-2,3-dihydro-2-oxo-5-phenyl-1H-1,4-benzodiazepin-3-yl)-N'-(3-formylaminophenyl)urea;
52. N-((3R)-1-((2R)-2-Hydroxy-3,3-dimethylbutyl)-2,3-dihydro-2-oxo-5-phenyl-1H-1,4-benzodiazepin-3-yl)-N'-(3-methylphenyl)urea;
53. N-((3R)-1-((2S)-2-Hydroxy-3,3-dimethylbutyl)-2,3-dihydro-2-oxo-5-phenyl-1H-1,4-benzodiazepin-3-yl)-N'-(3-methylphenyl)urea;
54. N-((3RS)-1-(1-Methylcyclopropyl)carbonylmethyl-2,3-dihydro-2-oxo-5-phenyl-1H-1,4-benzodiazepin-3-yl)-N'-(3-methylphenyl)urea;
55. N-((3RS)-1-tert-Butylcarbonylmethyl-2,3-dihydro-2-oxo-5-(2-chlorophenyl)-1H-1,4-benzodiazepin-3-yl)-N'-(3-methylphenyl)urea;
56. N-((3RS)-1-Isopropylcarbonylmethyl-2,3-dihydro-2-oxo-5-phenyl-1H-1,4-benzodiazepin-3-yl)-N'-(3-methylphenyl)urea;
57. N-((3R)-1-tert-Butylcarbonylmethyl-2,3-dihydr0-2-oxo-5-phenyl-1H-1,4-benzodiazepin-3-yl)-N'-(3-methylaminophenyl)urea;
58. N-((3RS)-1-tert-Butylcarbonylmethyl-2,3-dihydro-2-oxo-5-(2-pyridyl)-1H-1,4-benzodiazepin-3-yl)-N'-(3-methylaminophenyl)urea;
59. N-((3R)-1-tert-Butylcarbonylmethyl-2,3-dihydro-2-oxo-5-phenyl-1H-1,4-benzodiazepin-3-yl)-N'-(3-(N-ethyl-N-methylamino)phenyl)urea;
60. N-((3R)-1-tert-Butylcarbonylmethyl-2,3-dihydro-2-oxo-5-phenyl-1H-1,4-benzodiazepin-3-yl)-N'-(3-diethylaminophenyl)urea;
61. N-((3RS)-1-tert-Butylcarbonylmethyl-2,3-dihydro-2-oxo-5-phenyl-1H-1,4-benzodiazepin-3-yl)-N'-(3-dimethylaminomethylphenyl)urea;
62. N-((3RS)-1-tert-Butylcarbonylmethyl-2,3-dihydro-2-oxo-5-(2-pyridyl)-1H-1,4-benzodiazepin-3-yl)-N'-(3-(N-ethyl-N-methylamino)phenyl)urea;
63. N-((3RS)-1-tert-Butylcarbonylmethyl-2,3-dihydro-2-oxo-5-(2-pyridyl)-1H-1,4-benzodiazepin-3-yl)-N'-(3-dimethylaminomethylphenyl)urea;
64. N-((3RS)-1-tert-Butylcarbonylmethyl-2,3-dihydro-2-oxo-5-(2-pyridyl)-1H-1,4-benzodiazepin-3-yl-N'-(3-diethylaminophenyl)urea;

65. N-((3R)-1-tert-Butylcarbonylmethyl-2,3-dihydro-2-oxo-5-phenyl-1H-1,4-benzodiazepin-3-yl)-N'-(3-dimethylaminophenyl)urea;
66. N-((3RS)-1-tert-Butylcarbonylmethyl-2,3-dihydro-2-oxo-5-(4-methylphenyl)-1H-1,4-benzodiazepin-3-yl)-N'-(3-methylphenyl)urea;
67. N-((3R)-1-tert-Butylcarbonylmethyl-2,3-dihydro-2-oxo-5-phenyl-1H-1,4-benzodiazepin-3-yl)-N'-(3-aminophenyl)urea;
68. N-((3R)-1-tert-Butylcarbonylmethyl-2,3-dihydro-2-oxo-5-(2-pyridyl)-1H-1,4-benzodiazepin-3-yl)-N'-(3-methylphenyl)urea;
69. N-((3R)-1-tert-Butylcarbonylmethyl-2,3-dihydro-2-oxo-5-(2-pyridyl)-1H-1,4-benzodiazepin-3-yl)-N'-(3-aminophenyl)urea;
70. N-((3R)-1-tert-Butylcarbonylmethyl-2,3-dihydro-2-oxo-5-(2-pyridyl)-1H-1,4-benzodiazepin-3-yl)-N'-(3-methylaminophenyl)urea;
71. N-((3R)-1-tert-Butylcarbonylmethyl-2,3-dihydro-2-oxo-5-(2-pyridyl)-1H-1,4-benzodiazepin-3-yl)-N'-(3-dimethylaminophenyl)urea;
72. N-((3RS)-1-tert-Butylcarbonylmethyl-2,3-dihydro-2-oxo-5-phenyl-1H-1,4-benzodiazepin-3-yl)-N'-(3-aminophenyl)urea;
73. N-((3RS)-1-tert-Butylcarbonylmethyl-2,3-dihydro-2-oxo-5-phenyl-1H-1,4-benzodiazepin-3-yl)-N'-(3-methylaminophenyl)urea;
74. N-((3RS)-1-tert-Butylcarbonylmethyl-7-chloro-2,3-dihydro-2-oxo-5-phenyl-1H-1,4-benzodiazepin-3-yl)-N'-(3-methylphenyl)urea;
75. N-((3RS)-1-tert-Butylcarbonylmethyl-7-chloro-2,3-dihydro-2-oxo-5-phenyl-1H-1,4-benzodiazepin-3-yl)-N'-(3-dimethylaminophenyl)urea;
76. N-((3RS)-1-tert-Butylcarbonylmethyl)-7-chloro-2,3-dihydro-2-oxo-5-(2-chlorophenyl)-1H-1,4-benzodiazepin-3-yl)-N'-(3-methylphenyl)urea;
77. N-((3RS)-1-tert-Butylcarbonylmethyl-2,3-dihydro-8-methyl-2-oxo-5-phenyl-1H-1,4-benzodiazepin-3-yl)-N'-(3-methylphenyl)urea;
78. N-((3RS)-1-tert-Butylcarbonylmethyl-2,3-dihydro-2-oxo-5-phenyl-1H-1,4-benzodiazepin-3-yl)-N'-(3-(N-ethyl-N-methylaminophenyl)urea;
79. N-((3RS)-1-tert-Butylcarbonylmethyl-2,3-dihydro-2-oxo-5-phenyl-1H-1,4-benzodiazepin-3-yl)-N'-(3-diethylaminophenyl)urea.

9. A method according to claim 1, wherein $R^5$ is $(C_1-C_3)$ alkyl.

10. A method according to claim 2, wherein $R^5$ is $(C_1-C_3)$ alkyl.

11. A method according to claim 2, wherein at least one of $R^2$ and $R^3$ is unsubstituted phenyl or unsubstituted 2-, 3- or 4-pyridyl.

12. A method according to claim 1, wherein $R^4$ is linear or branched $(C_4-C_7)$ alkyl and $R^5$ is $(C_1-C_3)$ alkyl.

13. A method compound according to claim 1, wherein at least one of $R^2$ and $R^3$ is substituted with a substituent selected from the group consisting of a halogen atom, a hydroxy amino group, a nitro group, a carboxylic acid group, a cyano group, an alkyl group, an alkoxy group, an alkylamino group and a dialkylamino group, wherein alkyl portions of the recited groups consist of 1 to 6 carbon atoms.

14. A method according to claim 1, wherein at least one of W and X is hydrogen.

15. A method according to claim 3, wherein at least one of W and X is selected from $(C_1-C_3)$ alkyl and $(C_1-C_3)$ alkoxy groups.

16. A process for preparing a benzodiazepine compound of formula I, or a pharmaceutically acceptable salt thereof:

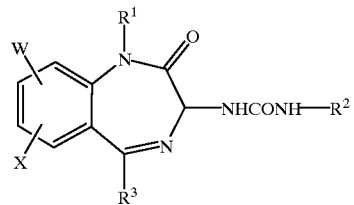

wherein (a) $R^1$ is —$CH_2CO(CH_2)_aR^5$ in which a is 0 or 1 and $R^5$ is selected from $(C_1-C_8)$alkyl groups, $(C_3-C_8)$ cycloalkyl and adamantyl groups, which may be unsubstituted or substituted by one or two $(C_1-C_8)$alkyl groups, and groups of formulae II and III;

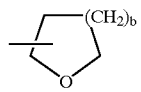

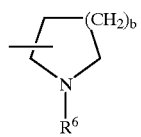

in which $R^6$ is H or $(C_1-C_8)$alkyl or —CO—$(C_1-C_6)$alkyl and b is 1 or 2;

(b) $R^2$ and $R^3$ are independently selected from 5- and 6-membered aromatic carbocyclic and 5- and 6-membered heterocyclic groups with one heteroatom selected from the groups consisting of N, O and S, where $R^2$ and $R^3$ each may have 1 or 2 substituents selected from the group consisting of a halogen atom, an amino group, a hydroxyl group, a nitro group, a cyano group, an alkyl group, an alkoxy group, a hydroxyamino group, an alkylamino group and a dialkylamino group, a carbamoyl group, a formylamino group, an alkylaminoalkyl group, a dialkylaminoalkyl group, a —$(CH_2)_c$—$CO_2H$ group in which c is 0–2 and a —$(CH_2)_c$—$SO_3H$ in which c is 0–2, wherein alkyl portions of the recited groups consist of 1 to 6 carbon atoms; and (c) W and X are selected independently from halogen and hydrogen atoms and $(C_1-C_8)$alkyl and $(C_1-C_8)$alkoxy groups, comprising the step of reacting 3-aminobenzodiazepine V with organic isocyanate $R^2$—NCO according to the following reaction scheme:

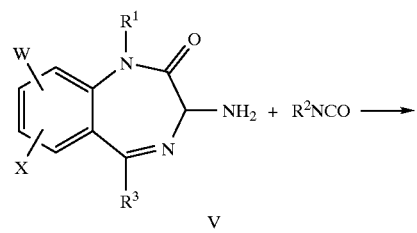

-continued

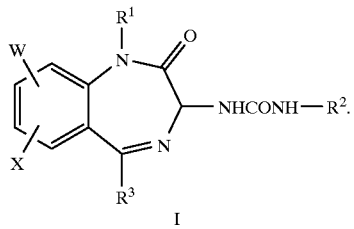

I

17. A process for preparing a benzodiazepine compound of formula I, or a pharmaceutically acceptable salt thereof:

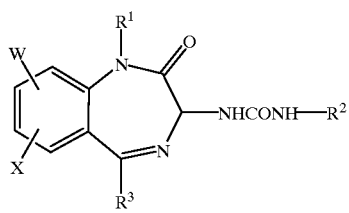

I wherein
(a) $R^1$ is —$CH_2CO(CH_2)_aR^5$ in which a is 0 or 1 and $R^5$ is selected from ($C_1$–$C_8$)alkyl groups, ($C_3$–$C_8$) cycloalkyl and adamantyl groups, which may be unsubstituted or substituted by one or two ($C_1$–$C_8$)alkyl groups, and groups of formulae II and III;

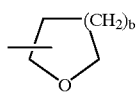

II

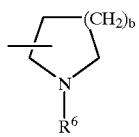

III in which $R^6$ is H or ($C_1$–$C_8$)alkyl or —CO—($C_1$–$C_6$)alkyl and b is 1 or 2;
(b) $R^2$ and $R^3$ are independently selected from 5- and 6-membered aromatic carbocyclic and 5- and 6-membered heterocyclic groups with one heteroatom selected from the groups consisting of N, O and S, where $R^2$ and $R^3$ each may have 1 or 2 substituents selected from the group consisting of a halogen atom, an amino group, a hydroxyl group, a nitro group, a cyano group, an alkyl group, an alkoxy group, a hydroxyamino group, an alkylamino group and a dialkylamino group, a carbamoyl group, a formylamino group, an alkylaminoalkyl group, a dialkylaminoalkyl group, a —$(CH_2)_c$—$CO_2H$ group in which c is 0–2 and a —$(CH_2)_c$—$SO_3H$ in which c is 0–2, wherein alkyl portions of the recited groups consist of 1 to 6 carbon atoms; and
(c) W and X are selected independently from halogen and hydrogen atoms and ($C_1$–$C_8$)alkyl and ($C_1$–$C_8$)alkoxy groups,
comprising the step of reacting 3-p-nitrophenyloxycarbonylaminobenzodiazepine VI with amine $R^2$—$NH_2$, according to the following reaction scheme

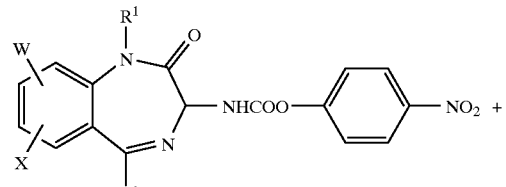

VI

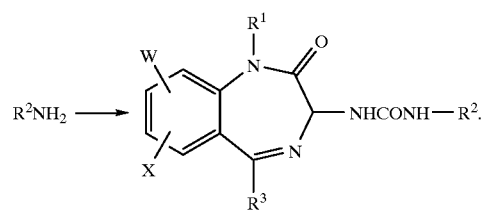

I

18. A process for preparing a benzodiazepine compound of formula I, or a pharmaceutically acceptable salt thereof:

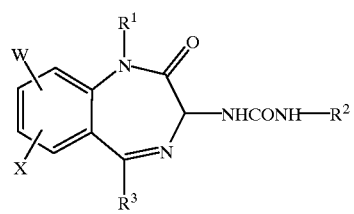

I wherein
(a) $R^1$ is —$CH_2CHOH(CH_2)_aR^4$, in which a is 0 or 1 and $R^4$ is selected from ($C_1$–$C_8$)alkyl groups, ($C_3$–$C_8$) cycloalkyl and adamantyl groups, which may be unsubstituted or substituted by one or two ($C_1$–$C_8$)alkyl groups, and groups of formulae II and III;

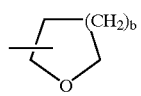

II

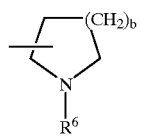

III in which $R^6$ is H or ($C_1$–$C_8$)alkyl or —CO—($C^1$–$C_6$)alkyl and b is 1 or 2;
(b) $R^2$ and $R^3$ are independently selected from 5- and 6-membered aromatic carbocyclic and 5- and 6-membered heterocyclic groups with one heteroatom selected from the groups consisting of N, O and S, where $R^2$ and $R^3$ each may have 1 or 2 substituents selected from the group consisting of a halogen atom, an amino group, a hydroxyl group, a nitro group, a cyano group, an alkyl group, an alkoxy group, a hydroxyamino group, an alkylamino group and a dialkylamino group, a carbamoyl group, a formylamino group, an alkylaminoalkyl group, a dialkylaminoalkyl group, a —$(CH_2)_c$—$CO_2H$ group in which c is 0–2 and a —$(CH_2)_c$—$SO_3H$ in which c is 0–2, wherein alkyl portions of the recited groups consist of 1 to 6 carbon atoms; and (c) W and X are selected independently from halogen and hydrogen atoms and ($C_1$–$C_8$)alkyl and ($C_1$–$C_8$)alkoxy groups, comprising the step of reacting a compound of general formula I with a reducing agent.

19. A method according to claim 1, wherein $R^1$ is —$CH_2CHOH(CH_2)_aR^4$ in which a is 0 or 1.

20. A method according to claim 1, wherein $R^1$ is a ketone group —$CH_2CO(CH_2)_aR^5$ in which a is 0 or 1.

* * * * *